(12) United States Patent
Annabi et al.

(10) Patent No.: US 9,688,741 B2
(45) Date of Patent: Jun. 27, 2017

(54) ELASTIC HYDROGEL

(71) Applicants: Elastagen Pty Ltd, Eveleigh, New South Wales (AU); President and Fellows of Harvard College, Cambridge, MA (US)

(72) Inventors: Nasim Annabi, New South Wales (AU); Anthony Steven Weiss, New South Wales (AU); Ali Khademhosseini, Cambridge, MA (US)

(73) Assignees: Elastagen Pty Ltd, Eveleigh, New South Wales (AU); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/438,187

(22) PCT Filed: Oct. 23, 2013

(86) PCT No.: PCT/AU2013/001230
§ 371 (c)(1),
(2) Date: Apr. 23, 2015

(87) PCT Pub. No.: WO2014/063194
PCT Pub. Date: May 1, 2014

(65) Prior Publication Data
US 2015/0274805 A1 Oct. 1, 2015

Related U.S. Application Data

(60) Provisional application No. 61/717,503, filed on Oct. 23, 2012.

(51) Int. Cl.
C07K 14/78 (2006.01)
A61L 27/52 (2006.01)
A61L 27/22 (2006.01)
A61L 27/38 (2006.01)
A61L 27/50 (2006.01)

(52) U.S. Cl.
CPC ............ *C07K 14/78* (2013.01); *A61L 27/227* (2013.01); *A61L 27/3804* (2013.01); *A61L 27/3826* (2013.01); *A61L 27/50* (2013.01); *A61L 27/52* (2013.01); *A61L 2300/64* (2013.01); *A61L 2430/20* (2013.01); *C12N 2533/50* (2013.01)

(58) Field of Classification Search
CPC . C07K 14/78; A61L 27/3804; A61L 27/3826; A61L 27/227; A61L 27/50; A61L 27/52; A61L 2300/64; A61L 2430/20
See application file for complete search history.

(56) References Cited

U.S. PATENT DOCUMENTS

| 4,947,840 A | 8/1990 | Yannas et al. |
|---|---|---|
| 5,260,203 A | 11/1993 | Ladner et al. |
| 6,248,516 B1 | 6/2001 | Winter et al. |
| 7,001,328 B1 | 2/2006 | Barofsky |
| 7,125,960 B2 | 10/2006 | Keiichi |
| 7,618,935 B2 | 11/2009 | Hill et al. |
| 7,700,126 B2 | 4/2010 | Ng et al. |
| 8,038,991 B1 | 10/2011 | Stankus et al. |
| 8,101,717 B2 | 1/2012 | Weiss et al. |
| 8,383,158 B2 | 2/2013 | Michal et al. |
| 8,518,105 B2 | 8/2013 | Hossainy et al. |
| 2003/0166846 A1 | 9/2003 | Rothstein |
| 2004/0110439 A1 | 6/2004 | Chaikof et al. |
| 2004/0253220 A1 | 12/2004 | Perrier et al. |
| 2004/0258676 A1 | 12/2004 | Perrier et al. |
| 2004/0267362 A1 | 12/2004 | Hwang et al. |
| 2005/0175600 A1 | 8/2005 | Ensley |
| 2005/0244393 A1 | 11/2005 | Phillipapart et al. |
| 2006/0115457 A1 | 6/2006 | Hnojewyj |
| 2007/0237735 A1 | 10/2007 | Denommee et al. |
| 2007/0287741 A1 | 12/2007 | Herzberg et al. |
| 2009/0035251 A1 | 2/2009 | Wortzman et al. |
| 2009/0169593 A1 | 7/2009 | Gregory et al. |
| 2009/0226519 A1 | 9/2009 | Claude et al. |
| 2010/0004699 A1 | 1/2010 | Alleyne et al. |
| 2010/0040710 A1 | 2/2010 | Perrier |
| 2010/0159008 A1 | 6/2010 | Barron et al. |
| 2011/0223230 A1 | 9/2011 | Hersel et al. |
| 2011/0229574 A1 | 9/2011 | Guillen |
| 2012/0220691 A1 | 8/2012 | Shreiber et al. |
| 2013/0071500 A1 | 3/2013 | Kizoulis et al. |
| 2013/0164340 A1* | 6/2013 | Ensley ................... A61K 38/39 424/400 |

(Continued)

FOREIGN PATENT DOCUMENTS

| EP | 0210846 | 2/1987 |
|---|---|---|
| EP | 0480048 | 4/1992 |
| WO | WO 9407921 | 4/1994 |

(Continued)

OTHER PUBLICATIONS

Mithieux, S.M., et al.; Biomaterials, 2004, vol. 25, p. 4921-4927.*
Annabi et al. (2013) "Elastomeric Recombinant Protein-Based Biomaterials" Biochemical Engineering Journal 77:110-118.
Annabi et al. (2013) "Engineered cell-laden human protein-based elastomer" Biomaterials 34:5496-5505.
Ayres et al. (2003) "Elastin-Based Side Chain Polymers Synthesized by ATRP" Macromolecules 36:5967-5973.
Ayres et al. (2005) "Stimulus Responsive Behavior of Elastin-Based Side Chain Polymers" Macromolecules 38:1699-1704.
Nagapudi et al. (2002) "Photomediated Solid-State Cross-Linking of an Elastin-Mimetic Recombinant Protein Polymer" Macromolecules 35:1730-1737.

(Continued)

Primary Examiner — Robert Jones, Jr.
(74) Attorney, Agent, or Firm — Edward J. Baba; Bozicevic, Field & Francis LLP

(57) ABSTRACT

The present invention relates to hydrogels and to the use of hydrogels for repair or restoration of tissue. In particular, the hydrogels of the present invention can be used for the repair or restoration of cardiac tissue.

12 Claims, 11 Drawing Sheets

(56) References Cited

U.S. PATENT DOCUMENTS

2013/0296528 A1   11/2013   Sommer-Knudsen

FOREIGN PATENT DOCUMENTS

| WO | WO 9414958 | 7/1994 |
|---|---|---|
| WO | WO 9834563 | 8/1998 |
| WO | WO 9844001 | 10/1998 |
| WO | WO 9903886 | 1/1999 |
| WO | WO 9911196 | 3/1999 |
| WO | WO 0004043 | 1/2000 |
| WO | WO 0073399 | 12/2000 |
| WO | WO 0136000 | 5/2001 |
| WO | WO 0156595 | 8/2001 |
| WO | WO 2004091592 | 10/2004 |
| WO | WO 2006101441 | 9/2006 |
| WO | WO 2007029913 | 3/2007 |
| WO | WO 2008033847 | 3/2008 |
| WO | WO 2008058323 | 5/2008 |
| WO | WO 2009015372 | 1/2009 |
| WO | WO 2009034559 | 3/2009 |
| WO | WO 2009099570 | 8/2009 |
| WO | WO 2010102337 | 9/2010 |
| WO | WO 2011127478 | 10/2011 |
| WO | WO 2012068619 | 5/2012 |
| WO | WO 2012080706 | 6/2012 |
| WO | WO 2013044314 | 4/2013 |
| WO | WO 2014089610 | 6/2014 |
| WO | WO 2015021508 | 2/2015 |
| WO | WO 2015042639 | 4/2015 |

OTHER PUBLICATIONS

Ozturk et al. (2009) "Dynamic cell culturing and its application to micropatterned, elastin-like protein-modified poly(N-isopropylacrylamide) scaffolds" Biomaterials 30:5417-5426.
Al-Obeidi et al. (1998) "Peptide and Peptidomimetic Libraries" Mol Biotechnol. 205-223.
Akhtar et al. (2010) "Oxidative and Nitrosative Modifications of Tropoelastin Prevent Elastic Fiber Assembly in Vitro" J Biol Chem, 285(48):37396-37404.
Albertine et al. (2010) "Chronic lung disease in preterm lambs: effect of daily vitamin A treatment on alveolarization" Am J Physiol Lung Cell Mol Physiol., 299:L59-72.
Almine et al. (2012) "Elastin Signaling in Wound Repair" Birth Defects Research, 96:248-257.
Altschul et al. (1990) "Basic Local Alignment Search Tool" J Mol Biol, 215:403-410.
Altschul et al. (1997) "Gapped BLAST and PSI-BLAST: a new generation of protein database search programs" Nucleic Acids Res, 25(17):3389-3402.
Amann and Brosius (1985) "'ATG vectors' for regulated high-level expression of cloned genes in Escherichia coli" Gene, 40:183-190.
Anderson et al. (2004) "Nanoliter-scale synthesis of arrayed biomaterials and application to human embryonic stem cells" Nature Biotechnology, 22(7):863-866.
Anderson et al. (2005) "Biomaterial microarrays: rapid, microscale screening of polymer-cell interaction" Biomaterials, 26:4892-4897.
Annabi et al. (2009) "The fabrication of elastin-based hydrogels using high pressure CO2" Biomaterials, 30:1-7.
Annabi et al. (2009) "Synthesis of highly porous crosslinked elastin hydrogels and their interaction with fibroblasts in vitro" Biomaterials, 30:4550-4557.
Annabi et al. (2010) "Cross-linked open-pore elastic hydrogels based on tropoelastin, elastin and high pressure CO2" Biomaterials, 31:1655-1665.
Aubin et al. (2010) "Directed 3D cell alignment and elongation in microengineered hydrogels" Biomaterials, 31:6941-6951.
Baar et al. (2005) "Self-organization of rat cardiac cells into contractile 3-D cardiac tissue" The FASEB Journal, 19:275-277.
Bae et al. (2011) "Cell-laden microengineered pullulan methacrylate hydrogels promote cell proliferation and 3D cluster formation" Soft Matter, 7:1903-1911.
Bax et al. (2009) "Cell Adhesion to Tropoelastin Is Mediated via the C-terminal GRKRK Motif and Integrin" Journal of Biological Chemistry, 284(42):28616-28623.
Bellingham et al. (2003) "Recombinant Human Elastin Polypeptides Self-Assemble into Biomaterials with Elastin-Like Properties" Biopolymers, 70:445-455.
Bjellqvist et al. (1993) "A nonlinear wide-range immobilized pH gradient for two-dimensional electrophoresis and its definition in a relevant pH scale" Electrophoresis, 14:1357-1365.
Boateng et al. (2005) "RGD and YIGSR synthetic peptides facilitate cellular adhesion identical to that of laminin and fibronectin but alter the physiology of neonatal cardiac myocytes" American Journal of Physiology—Cell Physiology, 288:C30-C38.
Brammer et al. (2009) "Improved bone-forming functionality on diameter-controlled TiO2 nanotube surface" Acta Biomaterialia, 5:3215-3223.
Cenizo et al. (2006) "LOXL as a target to increase the elastin content in adult skin: a dill extract induces the LOXL gene expression." Exp Dermatol. 8:574-581.
Charest et al. (2007) "Myoblast alignment and differentiation on cell culture substrates with microscale topography and model chemistries" Biomaterials, 28:2202-2210.
Chen et al. (2009) "Fibulin-4 regulates expression of the tropoelastin gene and consequent elastic-fibre formation by human fibroblasts" J. Biochem. 423:79-89.
Chung and Miller (1988) "A rapid and convenient method for the preparation and storage of competent bacterial cells" Nucleic Acids Res., 16(8):3580.
Cleary and Gibson (1996) "Elastic Tissue, Elastin and Elastin Associated Microfibrils" Extracellular Matrix, vol. 2 p. 95.
Dijke et al. (1989) "Growth Factors for Wound Healing" Bio/Technology, 7:793-798.
Eastoe (1955) "The Amino Acid Composition of Mammalian Collagen and Gelatin" Biochemical Journal, 61:589-600.
Falsey et al. (2001) "Peptide and Small Molecule Microarray for High Throughput Cell Adhesion and Functional Assays" Bioconjugate Chemistry, 12:346-353.
Feinberg et al. (2007) "Muscular Thin Films for Building Actuators and Powering Devices" Science, 317:1366-1370.
Fornieri et al. (1987) "Lysyl Oxidase Activity and Elastin/Glycosaminoglycan Interactions in Growing Chick and Rat Aortas" The Journal of Cell Biology, 105:1463-1469.
Giraud et al. (2007) "Current State of the Art in Myocardial Tissue Engineering" Tissue Engineering, 13(8):1825-1836.
Haedersdal et al. (2010) "Fractional CO2 Laser-Assisted Drug Delivery" Lasers Surg Med, 42:113-122.
Hashimoto et al. (2004) "Development of alginate wound dressings linked with hybrid peptides derived from laminin and elastin" Biomaterials, 25:1407-1414.
Hill et al. (2004) "CpnDB: A Chaperonin Sequence Database" Genome Res. 14:1669-1675.
Hruby et al. (1997) "Synthesis of oligopeptide and peptidomimetic libraries" Curr Opin Chem Biol, 1:114-119.
Huang et al. (2006) "Inhibition of Versican Synthesis by Antisense Alters Smooth Muscle Cell Phenotype and Induces Elastic Fiber Formation In Vitro and in Neointima After Vessel Injury" Circ Res., 98:370-377.
Hwang et al. (2008) "Retrovirally Mediated Overexpression of Glycosaminoglycan-Deficient Biglycan in Arterial Smooth Muscle Cells Induces Tropoelastin Synthesis and Elastic Fiber Formation in Vitro and in Neointimae after Vascular Injury" Am J Pathology, 173(6):1919-1928.
Jin et al. (2010) "Synthesis and characterization of hyaluronic acid—poly(ethylene glycol) hydrogels via Michael addition: An injectable biomaterial for cartilage repair" Acta Biomaterialia, 6:1968-1977.
Kalluri et al. (2011) "Characterization of Microchannels Created by Metal Microneedles: Formation and Closure" AAPS Journal, 13(3):473-481.
Kanematsu et al. (2004) "Collagenous matrices as release carriers of exogenous growth factors" Biomaterials, 25:4513-20.

(56) References Cited

OTHER PUBLICATIONS

Karlin & Altschul (1990) "Methods for assessing the statistical significance of molecular sequence features by using general scoring schemes" Proc Natl Acad Sci USA, 87:2264-2268.
Karlin & Altschul (1993) "Applications and statistics for multiple high-scoring segments in molecular sequences" Proc Natl Acad Sci USA, 90:5873-5877.
Kellouche et al. (2007) "Tissue engineering for full-thickness burns: A dermal substitute from bench to bedside" Biochemical and Biophysical Research Communications, 363:472-478.
Kozel et al. (2006) "Elastic Fiber Formation: A Dynamic View of Extracellular Matrix Assembly Using Timer Reporters" J Cell Physiol. 207:87-96.
Lanasa et al. (2009) "Influence of ECM proteins and their analogs on cells cultured on 2-D hydrogels for cardiac muscle tissue engineering" Acta Biomaterialia, 5:2929-2938.
Li et al. (2005) "Electrospun protein fibers as matrices for tissue engineering" Biomaterials, 26:5999-6008.
Li et al. (2006) "Electrospinning polyaniline-contained gelatin nanofibers for tissue engineering applications" Biomaterials, 27:2705-2715.
Liu et al. (2001) "Nanostructured Materials Designed for Cell Binding and Transduction" Biomacromolecules, 2:362-368.
Mahoney et al. (2008) "Extracellular matrix in cutaneous ageing: the effects of 0.1% copper-zinc malonate-containing cream on elastin Biosynthesis" Exp Dermatol, 18:205-211.
McDevitt et al. (2003) "Spatially organized layers of cardiomyocytes on biodegradable polyurethane films for myocardial repair" Journal of Biomedical Materials Research A, 66:586-595.
Mithieux et al. (2004) "Synthetic elastin hydrogels derived from massive elastic assemblies of self-organized human protein monomers" Biomaterials, 25:4921-4927.
Mithieux et al. (2009) "In situ polymerization of tropoelastin in the absence of chemical cross-linking" Biomaterials, 30:431-435.
Mitts et al. (2010) "Aldosterone and Mineralocorticoid Receptor Antagonists Modulate Elastin and Collagen Deposition in Human Skin" J Invest Dermatol., 130:2396-406.
Miyagawa et al. (2011) "Tissue-Engineered Cardiac Constructs for Cardiac Repair" Annals Thoracic Surgery, 91:320-329.
Miyamoto et al. (2009) "Creation of cross-linked electrospun isotypic-elastin fibers controlled cell-differentiation with new cross-linker" Int J Biol Macromolecules, 45:33-41.
Moon et al. (2006) "Preparation of Biodegradable Thermo-responsive Polyaspartamides with N-Isopropylamine Pendent Groups (I)" Bulletin of the Korean Chemical Society, 27(12):1981-1984.
Nichol et al. (2010) "Cell-laden microengineered gelatin methacrylate hydrogels" Biomaterials, 31:5536-5544.
Okamoto (1989) "Characteristics of Elastin Peptides in Coacervate States: Ph Effect and Possible Ion Transport Mechanism" Peptide Chemistry, 27th ed, 369-374.
Orner et al. (2004) "Arrays for the Combinatorial Exploration of Cell Adhesion" Journal of the American Chemical Society, 126:10808-10809.
Ostegaard & Holm (1997) "Peptomers:A versatile approach for the preparation of diverse combinatorial peptidomimetic bead libraries" Mol Divers, 3:17-27.
Ostresh et al. (1996) "Generation and Use of Nonsupport-Bound Peptide and Peptidomimetic Combinatorial Libraries" Methods in Enzymology, 267:220-234.
Peppas et al. (2006) "Hydrogels in Biology and Medicine: From Molecular Principles to Bionanotechnology" Advanced Materials, 18:1345-1360.
Raphel et al. (2012) "Photoreactive elastin-like proteins for use as versatile bioactive materials and surface coatings†" Journal of Materials Chemistry, 22:19429-19437.
Rnjak et al. (2011) "Severe Burn Injuries and the Role of Elastin in the Design of Dermal Substitutes" Tissue Engineering: Part B, 17(2):81-91.
Rnjak-Kovacina et al. (2012) "Electrospun synthetic human elastin:collagen composite scaffolds for dermal tissue engineering" Acta Biomater. 8:3714-3722.
Sato et al. (2007) "Distinct Steps of Cross-linking, Self-association, and Maturation of Tropoelastin Are Necessary for Elastic Fiber Formation" J Mol Biol. 369:841-851.
Shifren and Mecham (2006) "The Stumbling Block in Lung Repair of Emphysema: Elastic Fiber Assembly" Proc Am Thorac Soc. 3:428-433.
Shimatake and Rosenberg (1981) "Purified a regulatory protein cll positively activates promoters for lysogenic development" Nature, 292:128-132.
Smith et al. (2010) "Duration of wrinkle correction following repeat treatment with Juvederm hyaluronic acid fillers" Arch Dermatol Res, 302:757-762.
Sohm et al. (2011) Evaluation of the efficacy of a dill extract in vitro and in vivo Int J Cosmet Sci. 33:157-163.
Sreerama et al. (2000) "Estimation of Protein Secondary Structure from Circular Dichroism Spectra: Comparison of CONTIN, SELCON, and CDSSTR Methods with an Expanded Reference Set" Analytical Biochemistry, 287:252-260.
Studier and Moffat (1986) "Use of Bacteriophage T7 RNA Polymerase to Direct Selective High-level Expression of Cloned Genes" J Mol. Biol. 189:113-130.
Sykes and Partridge (1974) "Salt-Soluble Elastin from Lathyritic Chicks" Biochem J, 141:567-572.
Tandon et al. (2009) "Electrical stimulation systems for cardiac tissue Engineering" Nature Protocols, 4(2):155-173.
Thompson et al. (1994) "CLUSTAL W: improving the sensitivity of progressive multiple sequence alignment through sequence weighting, position-specific gap penalties and weight matrix choice" Nucleic Acid Research, 22(22):4673-4680.
Tourniare et al. (2006) "Polymer microarrays for cellular adhesion" Chem Comm, 2118-2120.
Vrhovski et al. (1997) "Coacervation characteristics of recombinant human tropoelastin" Eur J Biochem, 250:92-98.
Wagenseil and Mecham (2007) "New Insights into Elastic Fiber Assembly" Birth Defects Res C Embro Today, 81:229-240.
Ward et al. (2011) "Thermoresponsive Polymers for Biomedical Applications" Polymers, 3:1215-1242.
Wise et al. (2009) "Engineered Tropoelastin and Elastin-Based Biomaterials" Advances in Protein Chemistry and Structural Biology, 78:1-24.
Wu et al. (1999) "Glycosaminoglycans Mediate the Coacervation of Human Tropoelastin through Dominant Charge Interactions Involving Lysine Side Chains" Journal of Biological Chemistry, 274(31):21719-21724.
Yanagisawa and Davis (2010) "Unraveling the mechanism of elastic fiber assembly: The roles of short fibulins" Int J Biochem Cell Biol. 42:1084-1093.

\* cited by examiner

ELASTIC HYDROGEL

FIELD OF THE INVENTION

The invention relates to hydrogels, especially hydrogels comprised of cross-linked peptides, and to the use of these hydrogels for repair or restoration of biological tissue.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

Hydrogels have emerged as leading candidates for various tissue engineering applications due to their similarity with the native extracellular matrix (ECM, Peppas et al. (2006)). Among the natural hydrogels, elastin-based biomaterials have shown remarkable properties including elasticity, self-assembly, long-term stability, and biological activity.

Various cross-linking approaches have been used to produce three-dimensional elastin-based hydrogels from recombinant human tropoelastin, α-elastin, and engineered elastin-like polypeptides (Mithieux et al. (2004) and Annabi et al. (2010)). The resultant hydrogels have shown biocompatibility and supported cell growth both in vitro and in vivo. However, non-homogenous cell distribution within the three-dimensional structures of these hydrogels has been an issue (Mithieux et al. (2004)). This has generally arisen from the fact that in a pre-formed gel (i.e. a gel that has been prepared before addition of cells to it) cell distribution is generally a function of cell growth or spreading throughout the gel. Put in other words, distribution of cells throughout a pre-formed gel arises as the cells replicate or move throughout the hydrogel. One problem is that once seeded in a pre-formed gel, many cells have limited capacity for movement, or require significant time to generate sufficient cell number for complete distribution through and complete colonisation of a gel. The end result may be clumping of cells and formation of cell colonies in localised regions of the gel where the cells have been seeded, rather than dispersion or distribution of cells throughout a hydrogel.

It has not been possible to incorporate cells in or on a hydrogel during hydrogel formation. This is because harsh conditions used in the fabrication techniques, such as the use of chemical cross-linkers (Mithieux et al. (2004)), organic solvents (Annabi et al. (2009)) and high pressure (Annabi et al. (2010) and Annabi et al. (2009)), have prevented the possibility of cell incorporation during hydrogel formation. In particular, previous methods have prevented the incorporation of cells evenly in the matrix without damaging cell viability Many applications of hydrogels require the hydrogel to maintain a particular shape or pattern so as to provide the desired end function. For example, it may be necessary for the hydrogel to provide grooves or other cell guiding structures for aligning cells in a desired direction. One problem with many hydrogels is that the shapes or patterns formed on them tend not to persist for sufficient periods of time required for the cells to adopt the required alignment.

In nearly all applications, hydrogels are required to support cell proliferation and spreading. However, many hydrogels limit the capacity for either or both of these cell activities. One further problem of some hydrogels is that they have a structural characteristic that impedes the desired functional characteristic of the particular cell of interest. For example, the hydrogel may have a degree of elasticity which is incompatible with a desired cell contraction, and which therefore masks the desired cell property.

There is therefore a need to develop hydrogels, scaffolds and the like that can be used in tissue engineering applications. Ideally, these scaffolds should be biocompatible (i.e. non-toxic to biological tissue and non-immunogenic), durable, stable, have the desired mechanical properties (for example, strength and elasticity) and allow for the provision of viable cells that are, preferably, distributed more or less evenly throughout and upon the hydrogel, or otherwise distributed in a desired or pre-selected or pre-defined pattern in or on the hydrogel.

SUMMARY OF THE INVENTION

The invention seeks to address, or at least to provide an improvement to, one or more of the above mentioned limitations, needs or problems and, in one aspect, provides a tropoelastin monomer comprising an acrylate group attached to at least one primary amine group of the monomer.

The present invention relates to a tropoelastin comprising an acrylate group attached to at least one amine group of the tropoelastin. In one embodiment, the tropoelastin is a tropoelastin multimer comprised of two or more tropoelastin monomers. In one embodiment, the tropoelastin monomers are cross-linked (e.g. by covalent bonds between amine groups of amino acids present in the tropoelastin monomers).

The present invention also relates to acrylated tropoelastin formed by the process of treating tropoelastin with a compound comprising an acrylate group in conditions for attaching the acrylate group of the compound to an amine group of the tropoelastin.

In one embodiment, the degree of acrylation of the tropoelastin is from about 5% to about 90%, from about 10% to about 80%, from about 15% to about 75%, from about 20% to about 60%, from about 25% to about 55%, or from about 30% to about 50%.

In one embodiment, from about 5% to about 90% of the lysine residues of the tropoelastin are attached to an acrylate group. For example, from about 15% to about 75% or form about 30% to about 50% of the lysine residues of the tropoelastin may be attached to an acrylate group.

The present invention also relates to a composition comprising a tropoelastin comprising an acrylate group attached to at least one amine group of the tropoelastin.

The present invention also relates to a composition comprising an acrylated tropoelastin formed by the process of treating a tropoelastin with a compound comprising an acrylate group in conditions for attaching the acrylate group of the compound to an amine of the tropoelastin.

The present invention also relates to a composition comprising cross-linked tropoelastin, the cross-linked tropoelastin comprising:
  a plurality of tropoelastin monomers or multimers;
  a linker in the form of a compound having an acrylate group, wherein the acrylate group of the compound is attached to an amine group of the tropoelastin for cross-linking the monomers or multimers.

The present invention also relates to a composition comprising cross-linked tropoelastin formed by the process of cross-linking a tropoelastin as defined above.

The present invention also relates to a hydrogel comprising a composition as defined above or a tropoelastin as defined above.

The present invention also relates to a hydrogel as defined above, wherein:
from about 30% to about 50% of the lysine residues of the tropoelastin are attached to an acrylate group; and
the concentration of acrylated tropoelastin in the hydrogel is from about 5 to about 15% (w/v).

The present invention also relates to a process for forming a composition suitable for forming a hydrogel, the process comprising:
providing an aqueous solution comprising tropoelastin as defined above;
subjecting the aqueous solution to conditions for cross-linking the tropoelastin thereby producing the composition.

The present invention also relates to a process for producing a hydrogel comprising:
forming an aqueous solution comprising acrylated tropoelastin and one or more cells;
subjecting the aqueous solution to conditions for cross-linking the acrylated tropoelastin to form a hydrogel having the one or more cells contained in the hydrogel;
thereby forming the hydrogel.

In one embodiment, the aqueous solution comprises acrylated tropoelastin monomers.

The present invention also relates to an acrylated tropoelastin monomer formed by the process of treating a tropoelastin monomer with a compound comprising an acrylate group.

In one embodiment, the degree of acrylation of the tropoelastin monomer is from about 5% to about 90%, from about 10% to about 80%, from about 15% to about 75%, from about 20% to about 60%, from about 25% to about 55%, or from about 30% to about 50%.

The present invention also relates to a composition comprising cross-linked tropoelastin, the cross-linked tropoelastin comprising:
a plurality of tropoelastin monomers;
a linker in the form of an acrylate group for cross-linking the monomers.

The present invention further relates to a composition comprising cross-linked tropoelastin formed by the process of cross-linking an above-described tropoelastin monomer comprising an acrylate group.

The present invention also relates to a process for forming a composition suitable for forming a hydrogel, the process including:
providing an aqueous solution including acrylated tropoelastin monomers;
subjecting the aqueous solution to conditions for cross-linking the acrylated tropoelastin monomers
thereby producing the composition.

In another embodiment there is provided a process for producing a hydrogel having a cell encapsulated therein comprising:
combining acrylated tropoelastin monomers with a cell to form an aqueous solution comprising acrylated tropoelastin monomers and having the cell contained therein;
subjecting the aqueous solution to conditions for cross linking the tropoelastin monomers;
thereby forming a hydrogel having a cell encapsulated therein.

The present invention also relates to a hydro gel comprising a composition as described above, as well as a device, support or scaffold comprising the hydrogel.

In one embodiment, the acrylate is a methacrylate derived from, for example, methacrylate anhydride.

In another embodiment, the tropoelastin is a human tropoelastin.

In other embodiments there are provided methods and uses of the hydrogel, for repairing or restoring biological tissue.

BRIEF DESCRIPTION OF THE DRAWINGS

FIG. 1a, Representative $^1$H NMR spectrum of tropoelastin and TpeMA solutions in $D_2O$ measured at 4° C., as the methacrylation degree increases, the peaks that correspond to methacrylate groups (between 4.9 and 6 ppm) grow in intensity at the expense of the peak correlated to lysine residues in tropoelastin (2.6 ppm), the methacrylation degree of TpeMA (defined as discussed further below) is provided in parentheses. FIG. 1b, Coacervation curves for tropoelastin and TpeMA with different degrees of methacrylation, the coacervation temperature decreased with increase in the methacrylation degree. FIG. 1c, CD spectrum of tropoelastin and TpeMA with various methacrylation degrees. FIG. 1d, % secondary structure, indicating that methacrylation had no significant effect on the secondary structure of tropoelastin.

FIG. 2a, Effect of methacrylation on pore characteristics and equilibrium swelling properties of TpeMA gel, SEM images from the cross-sections of 10% (w/v) TpeMA hydrogels with (ai) 31, (aii) 44 and (aiii) 48% methacrylation degree (scale bars: 50 μm), the structures of the hydrogels became more compact by increasing the methacrylation degree; (aiv) effect of methacrylation degree on the average pore sizes of TpeMA gels determined from the SEM images by using Image) software (n: 100); (av) effect of methacrylation degree on the swelling ratios of the hydrogels. FIG. 2b, Tensile properties and unconfined compressive properties of the fabricated gels, (bi) images from 15% (w/v) TpeMA gel with 31% methacrylation degree before and after stretching; representative strain/stress curves and elastic modulus of hydrogels produced from (bii and biii) 10% (w/v) TpeMA at varying degrees of methacrylation and 10% (w/v) GelMA with 80% methacrylation degree; and (biv and by) various concentrations of TpeMA with 31% methacrylation degree; representative cyclic strain/stress curves and compressive modulus for hydrogels produced from (bvi and bvii) various concentrations of TpeMA with 31% methacrylation degree; and (bviii and bix) 10% (w/v) TpeMA at varying degrees of methacrylation.

FIG. 3a, Characterization of encapsulated 3T3 cell behaviour in TpeMA gels fabricated by using different TpeMA concentrations at various culture times. 3T3 fibroblasts embedded in three dimensional TpeMA gel were stained with calcein-AM (green)/ethidium homodimer (red) Live/Dead assay, Live/Dead images from 3T3 cells encapsulated within (ai) 10 and (aii) 15% (w/v) TpeMA gels on day 7 of culture (scale bar: 100 μm); (aiii) quantification of cell viability by Live/Dead assay using ImageJ software 1, 4 and 7 days after encapsulation (TpeMA with 31% methacrylation was used for hydrogel fabrication). FIG. 3b, Cell viabilities on the surfaces of TpeMA hydrogels; Live/Dead images from the hydrogels seeded by HUVECs after (bi) 1 day, and (bii) 7 days of culture; (biii) quantification of cell viabilities 1, 4 and 7 days after cell seeding (TpeMA gels were produced using 10% (w/v) TpeMA with 31% methacrylation). FIG. 3c, HUVECs adhesion and proliferation on TpeMA surfaces; (ci) SEM images from the top surfaces of TpeMA hydrogels seeded with HUVECs on day 7 of culture (scale bar: 20 µm), indicating that cells readily adhere to the surface of the fabricated hydrogels, the hydrogels were produced using 10% (w/v) TpeMA with 31% methacrylation; (cii) Rhodamine-labelled phalloidin/DAPI staining for F-actin/cell nuclei of TpeMA gels seeded with HUVECs on day 7 of culture (scale bar: 100 µm); (ciii) the cell densities, defined as the number of DAPI stained nuclei per given hydrogel area, increased over the culture time, demonstrating cell proliferation on the surfaces of TpeMA gels. FIG. 3d, Cardiomyocyte attachment and proliferation on TpeMA and GelMA hydrogels as a function of time, (di) Rhodamine-labelled phalloidin/DAPI staining for F-actin/cell nuclei of cardiomyocytes seeded on GelMA (top panel) and TpeMA (bottom panel) gels after 24 h of culture (scale bar: 100 µm); (dii) the cell densities, defined as the number of DAPI stained nuclei per given hydrogel area, demonstrated higher cell attachment on TpeMA gel compared to GelMA at different culture time; (diii) the cell area, defined as the area of a cluster of the cells divided by the number of the cells within the cluster, confirmed higher cell spreading on the surface of TpeMA gel compared to GelMA hydrogel up to day 3 of culture; however, a reduction in cell area was observed on TpeMA gel compared to GelMA at day 8, which can be due to the higher cell proliferation on the surface of TpeMA gel.

FIG. 4a, Representative images from micropatterned gels containing (ai) 20×20 µm, and (aii) 50×50 µm patterns (scale bar: 200 µm). FIG. 4b, Histogram of the relative alignment in 20° increments on day 3 of culture, demonstrates increased cellular alignment with decreasing microchannels width. FIG. 4c; Histogram of the relative alignment obtained at different culture time, shows the highest cell alignment on day 3 of culture. FIG. 4d, Cell alignment on TpeMA and GelMA hydrogels on day 3 of culture, representative F-actin/DAPI stained images with corresponding histograms of (di, dii) patterned TpeMA and (diii, div)=patterned TpeMA; (dv, dvi) patterned GelMA; (dvii, dviii) unpatterned GelMA, demonstrating higher cell alignment in 20° increments on micropatterned TpeMA gel compared to patterned GelMA hydrogel (channel size: 20×20 µm, scale bar: 100 µm). FIG. 4e, Immunostaining staining and expression of cardiomyocyte proteins, hydrogels stained for (ei-eiv) troponin (green)/DAPI (blue) and (ev-eviii) α-sacromeric actinin (green)/connexin-43 (red)/DAPI (blue) on day 8 of culture, patterned TpeMA gels are shown in (ei) and (ev) and unpatterned TpeMA samples in (eii) and (evi), patterned GelMA in (eiii) and (vii), and =patterned GelMA in (eiv) and (eviii) (scale bar: 50 µm).

FIGS. 6a and 6b, Stimulation chamber for applying electrical stimuli to cardiomyocytes cultured on the surfaces of TpeMA gels. Analyses of contractile response to electrical stimulation on day 5 of culture, voltage was gradually increased at (FIG. 6c) 1 Hz and (FIG. 6d) 2 Hz frequencies to induce synchronized beating, the beating became more synchronized by increasing the voltage. FIG. 6e, Excitation, threshold of cardiac tissues on both patterned and =patterned TpeMA gels at various frequencies, demonstrating that the excitation threshold was lower in patterned TpeMA gels compared to unpatterned ones. FIG. 6f, Recording of synchronous beating signal of cardiomyocyte cultured on a patterned TpeMA gel in response to applied external electric field at 0.5, 1, 2 and 3 Hz.

(FIGS. 7b and 7e) 10; and (FIGS. 7c and 7f) 15% (w/v) protein concentrations, exhibiting highly porous structure of hydrogels and the presence of pores both on the top surfaces and cross-sections of TpeMA gels (TpeMA with 31% methacrylation degree was used to fabricate hydrogels), top surfaces are shown in a-c and cross-sections in d-f (scale bars: 100 µm). FIG. 7g, The average pore sizes on the top surfaces and within the cross sections of TpeMA gels with varying polymer concentration, determined from the SEM images by using ImageJ software. FIG. 7h, Effect of protein concentration on the swelling ratios of the hydrogels.

FIG. 8d, SEM images from the top surface of a TpeMA hydrogel seeded with 3T3 on day 7 of culture (scale bar: 10 µm), demonstrating that cells adhere to the surface of the gel. FIG. 8e, Rhodamine-labeled phalloidin/DAPI staining for F-actin/cell nuclei of TpeMA gels seeded with 3T3 on day 7 of culture (scale bar: 100 µm) (TpeMA gels were produced using 10% (w/v) TpeMA with 31% methacrylation).

(FIGS. 11c and 11d) 15% (w/v) TpeMA (patterned gels are shown in FIGS. 11a and 11c and unpatterned in FIGS. 11b and 11d). FIG. 11e Mean percentage of aligned cell nuclei (within 20° of preferred nuclear orientation), demonstrating cell alignment for both TpeMA concentrations.

DETAILED DESCRIPTION OF THE EMBODIMENTS

Figure 1:
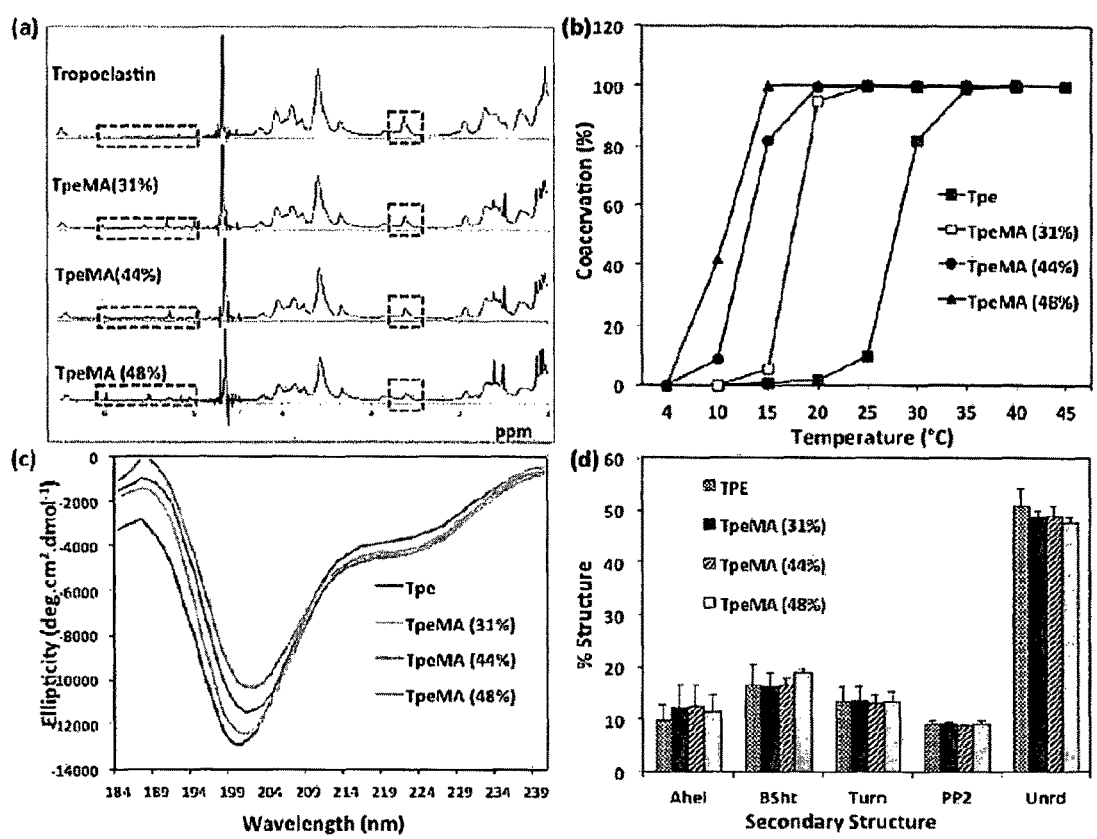
FIGS. 1a-1d show the effect of methacrylation on tropoelastin.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps.

The advantageous properties of the hydrogels of the present invention are discussed throughout the present specification, and in particular, are exhibited in the Examples, which show that hydrogels of the present invention can be made in a simple manner using a simple cross-linking reaction of modified tropoelastins, and that the hydrogels formed possess the required properties of biocompatibility, strength, resilience and cell encapsulation that enable them to be used in tissue engineering applications.

Hydrogels are used as scaffolds for tissue engineering applications because of their biocompatibility and high water content, which resemble the natural tissue microenvironment. However, the scope of their application is often limited by their low mechanical properties and limited extensibility, particularly in the regeneration of elastic tissues where elasticity plays an important functional role. Hydrogels of the present invention (i.e. those comprising acrylated, cross-linked tropoelastin) show remarkable (up to 400%) extensibility. In contrast, most prior art hydrogels rupture easily when stretched. The literature states that elastin has less extensibility because it is cross-linked. Therefore, the literature teaches away from a cross-linking approach with tropoelastin as a way to obtain highly elastic yet durable structures.

The inventors have previously shown that elastin-based hydrogels made from recombinant human tropoelastin, alpha elastin, and combinations of both, are elastic and could support cellular attachment and proliferation (Annabi et al. (2010)). However, non-homogeneous cell distribution within these hydrogels was an issue. By adding cells to a hydrogel precursor prior to the gelling process, cells can be distributed homogeneously throughout the gel. However, as mentioned above, cytotoxic conditions used in the fabrication of elastin-based gels in previous studies (for example the use of chemical cross-linkers, organic solvents and high pressures) have prevented cell encapsulation during hydrogel formation. To the inventor's knowledge, there are no reports in the literature that present the fabrication of highly elastic gels that can be used as substrates for three-dimensional cell containment.

Further, efforts have been made to synthesize synthetic-based elastomers (for example, poly(glycerol-sebacate), PGS) with improved mechanical properties but viable cells cannot be encapsulated within the three-dimensional structures of these stretchable hydrogels due to the method of manufacture. The present work demonstrates, for the first time, that a highly elastic cell-laden protein-based hydrogel can be synthesized through photo-cross-linking of methacrylated human recombinant tropoelastin. This is the first three-dimensional elastic hydrogel that can be photo-cross-linked after exposing to UV light for 35 sec to form a highly stretchable hydrogel network containing viable cells within its three-dimensional structure. Photoreactive elastin-mimetic scaffolds have been fabricated (Nagapudi et al. (2002) and Raphel et al. (2012)) but these synthesized materials cannot be used as hydrated three-dimensional hydrogels for cellular containment and are only used as fibers or two-dimensional films for surface seeding. The present inventors were surprised that the present hydrogels would also allow for cell encapsulation because the literature states that cells are found outside elastin, i.e. elastin does not encapsulate cells in vivo.

As mentioned above, the hydrogels described herein exhibit extensibility up to 400% and can be used for the regeneration of elastic tissue such as cardiovascular tissue. The inventors and others have reported the synthesis of various cell-laden hydrogels by methacrylate functionalization of different polymers such as gelatin and pullulan (Nichol et al. (2010) and Bae et al. (2011)). However, none of these previous hydrogels exhibited elasticity, mechanical stability or the excellent cell-interactive properties of the hydrogels described herein.

In the present work, the inventors have shown that acrylated gelatin hydrogels (similar to those synthesized by Nichol et al. (2010)) degrade very fast and have compressive modulus <30 kPa, elastic modulus of 3.3 kPa and maximum extensibility of ~100%, which are below the values obtained for the hydrogels described herein (compressive modulus of up to 160 kPa, elastic modulus of ~15 kPa and extensibility of up to ~400%). In addition, the micropatterned hydrogels described herein are surprisingly more stable than patterned methacrylated gelatin gels and support heart muscle cell organization. One would not expect elastin to direct muscle growth because muscle cells are not normally in contact with elastin.

The inventors have further shown that cardiomyocytes display better attachment and spreading on the hydrogels of the present invention compared to methacrylated gelatin. Substantial acrylation would be expected to decrease cell attachment to the C-terminal RKRK which is high in lysine (i.e., reacts with acrylate) yet is required for cell attachment (Bax et al. (2009)). Surprisingly cells interacted well even at high acrylation.

The beat frequency of cardiomyocytes was unexpectedly higher on patterned compared to unpatterned hydrogels of the present invention. This effect was not seen on methacrylated gelatin, so it is not possible to predict this behaviour of the hydrogels described herein.

Accordingly, the hydrogels described herein are novel and unique hydrogels. The hydrogels show high elasticity and mechanical stability similar to synthetic elastomers such as polydimethylsiloxane (PDMS) and excellent cell interactive properties similar to/better than other cell-laden natural-based hydrogels such as gelatin, collagen and pullulan.

The term "tropoelastin monomer" as used herein refers to a monomeric protein encoded by the elastin (ELN) genomic sequence (or gene). Tropoelastin monomers (also referred to herein as "tropoelastin") are approximately 70 kDa in size. There are 36 small domains in tropoelastin and each weighs about 2 kDa. Within the exons, there are alternating hydrophobic domains rich in non-polar amino acids such as glycine, valine, proline, alanine and leucine (which domains often occur in repeats of three to six peptides such as GVGVP, GGVP and GVGVAP), and hydrophilic domains rich in lysine and alanine. The hydrophilic domains often consist of stretches of lysine separated by two or three alanine residues such as AAAKAAKAA. Additionally, tropoelastin ends with a hydrophilic carboxy-terminal sequence containing its only two cysteine residues. Tropoelastin does not undergo cleavage and forming the microfibril is achieved by a self-association process termed coacervation.

Tropoelastin aggregates at physiological temperature due to interactions between hydrophobic domains. This process is reversible and thermodynamically controlled. The coacervate is stabilized by cross-linking via lysyl oxidase. The coacervate then becomes insoluble and the process is irreversible. The coacervate then condenses to form a cross-linked structure of four residues, either desmosine or isodesmosine.

In certain embodiments the tropoelastin monomer that is used in the present invention includes both hydrophilic and hydrophobic domains because the hydrophilic domains are important for the acrylation and water-binding aspect (which, in part, contributes to cell viability) and the hydrophobic domains are believed to be important for providing the elasticity that is a feature of the hydrogels of the present invention. It will be appreciated that the nature, number and size of the domains can be varied to obtain tropoelastin monomers having particular properties. Some additional examples of suitable tropoelastin monomers are given below:

```
GGVPGAIPGGVPGGVFYP;

GVGLPGVYP

GVPLGYP

PYTTGKLPYGYGP

GGVAGAAGKAGYP

TYGVGAGGFP

KPLKP

ADAAAAYKAAKA

GAGVKPGKV

GAGVKPGKV

TGAGVKPKA

QIKAPKL

AAAAAAAKAAAK
```
-continued
```
AAAAAAAAAAKAAKYGAAAGLV

EAAAKAAAKAAKYGAR

EAQAAAAAKAAKYGVGT

AAAAAKAAAKAAQFGLV

GGVAAAAKSAAKVAAKAQLRAAAGLGAGI

GALAAAKAAKYGAAV

AAAAAAAKAAAKAA

AAAAKAAKYGAA

CLGKACGRKRK.
```

Other suitable tropoelastin sequences are known in the art and include CAA33627 (*Homo sapiens*), P15502 (*Homo sapiens*), AAA42271 (*Rattus norvegicus*), AAA42272 (*Rattus norvegicus*), AAA42268 (*Rattus norvegicus*), AAA42269 (*Rattus norvegicus*), AAA80155 (*Mus musculus*), AAA49082 (*Gallus gallus*), P04985 (*Bos taurus*), ABF82224 (*Danio rerio*), ABF82222 (*Xenopus tropicalis*) and P11547 (*Ovis aries*). In a preferred embodiment, the tropoelastin monomers for use in the present invention are derived from human tropoelastin. In one embodiment, they have the sequence corresponding to amino acid residues 27-724 of GenBank entry AAC98394. As stated herein, the present invention also includes variants, for example species variants or polymorphic variants.

The tropoelastin monomers for use in the present invention may be obtained from recombinant sources. They can also be extracted from natural sources or synthesised (by, for example, solid-phase synthesis techniques). Tropoelastin monomers are also commercially available.

There are a number of isoforms of tropoelastin and therefore the exact number of amino acids that make up the tropoelastin polypeptide will vary. The term "polypeptide" or "polypeptide chain" refers to a polymer of amino acids, usually linked together by amide bonds. A functionally-active polymer of amino acids is generally referred to as a "protein". The present invention also includes variants of tropoelastin, for example species variants or polymorphic variants. The present invention is intended to cover all functionally active variants of tropoelastin that exhibit the same activity (i.e. cross-linkability by the use of acrylate, and elasticity). This also includes apo- and holo-forms of tropoelastin, post-translationally modified forms, as well as glycosylated or de-glycosylated derivatives. Such functionally active fragments and variants include, for example, those having conservative amino acid substitutions.

The term "functionally active" in relation to a fragment or variant of tropoelastin means the fragment or variant (such as an analogue, derivative or mutant) that is capable of forming a hydrogel, as discussed further below. Such variants include naturally occurring variants and non-naturally occurring variants. Additions, deletions, substitutions and derivatizations of one or more of the amino acids are contemplated so long as the modifications do not result in loss of functional activity of the fragment or variant. A functionally active fragment can be easily determined by shortening the amino acid sequence, for example using an exopeptidase, or by synthesizing amino acid sequences of shorter length, and then testing for hydrogel formation ability such as by the methods illustrated in the examples below.

Where non-natural variations occur, the fragment may be called a peptidomimetic, which are also within the scope of the invention. For example, synthetic amino acids and their analogues may be substituted for one or more of the native amino acids providing hydrogel-forming activity as described further below.

A "peptidomimetic" is a synthetic chemical compound that has substantially the same structure and/or functional characteristics of a tropoelastin for use in the present invention. A peptidomimetic generally contains at least one residue that is not naturally synthesised. Non-natural components of peptidomimetic compounds may be one or more of: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, for example, a beta turn, gamma turn, beta sheet, alpha helix conformation, and the like.

Peptidomimetics can be synthesized using a variety of procedures and methodologies described in the scientific and patent literatures (for example, Gilman et al., al-Obeidi (1998), Hruby (1997), Ostergaard (1997), Ostresh (1996)).

Preferably, the functionally active fragment is about 100 amino acids in length. Generally, the shortest fragment for use in the present invention will be about 10 amino acids in length. Therefore, the fragment may be between about 100 and about 10 amino acids in length. Shorter fragments are advantageous where, for example, the fragments are sought to be made by synthetic techniques because the preparation of long fragments by, for example, solid-phase synthesis, can be difficult to achieve. Fragments are generally synthesised in vitro where very pure products are desired to be obtained. The advantage of longer fragments is that the hydrophobic/hydrophilic nature of the fragment can be more easily fine-tuned, as can its elastic and water-binding properties. Preferably, the functionally active fragment or variant has at least approximately 60% identity to a peptide such as described above, more preferably at least approximately 65%, 66%, 67%, 68%, 69%, 70%, 71%, 72%, 73%, 74%, 75%, 76%, 77%, 78%, 79%, 80%, 81%, 82%, 83%, 84% or 85% identity, even more preferably at least 90% identity, even more preferably at least 95%, 96%, 97%, 98%, 99% or 100% identity. The functionally active fragment or variant may correspond to, or have identity with, a contiguous sequence of amino acids from the tropoelastin, however it is also contemplated that a functionally active fragment corresponds to, or has identity with, sequences of amino acids that are clustered spatially in the three dimensional structure of the tropoelastin.

Such functionally active fragments and variants include, for example, those having conservative amino acid substitutions. Those skilled in the art can determine appropriate parameters for measuring alignment, including any algorithms (non-limiting examples described below) needed to achieve maximal alignment over the full length of the sequences being compared. When amino acid sequences are aligned, the percent amino acid sequence identity of a given amino acid sequence A to, with, or against a given amino acid sequence B (which can alternatively be phrased as a given amino acid sequence A that has or comprises a certain percent amino acid sequence identity to, with, or against a given amino acid sequence B) can be calculated as: percent amino acid sequence identity=(X/Y)×100, where X is the number of amino acid residues scored as identical matches by the sequence alignment program's or algorithm's alignment of A and B, and Y is the total number of amino acid residues in B. If the length of amino acid sequence A is not equal to the length of amino acid sequence B, the percent amino acid sequence identity of A to B will not equal the percent amino acid sequence identity of B to A.

In calculating percent identity, exact matches are counted. The determination of percent identity between two sequences can be accomplished using a mathematical algorithm. A non-limiting example of a mathematical algorithm utilized for the comparison of two sequences is the algorithm of Karlin and Altschul (1990), modified as in Karlin and Altschul (1993). Such an algorithm is incorporated into the BLASTN and BLASTX programs of Altschul et al. (1990). To obtain gapped alignments for comparison purposes, Gapped BLAST (in BLAST 2.0) can be utilized as described in Altschul et al. (1997). Alternatively, PSI-Blast can be used to perform an iterated search that detects distant relationships between molecules. See Altschul et al. (1997) supra. In one preferred embodiment, utilizing BLAST, Gapped BLAST, and PSI-Blast programs, the default parameters of the respective programs (for example, BLASTX and BLASTN) are used. Alignment may also be performed manually by inspection. Another non-limiting example of a mathematical algorithm utilized for the comparison of sequences is the ClustalW algorithm (Higgins et al. (1994)). ClustalW compares sequences and aligns the entirety of the amino acid or DNA sequence, and therefore can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™ or JalView (http://www.jalview.org/). GENEDOC™ allows assessment of amino acid (or DNA) similarity and identity between multiple proteins. Another non-limiting example of a mathematical algorithm utilized for the comparison of sequences is the algorithm of Myers and Miller (*CABIOS* 1988; 4: 11-17). Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). In one preferred embodiment, utilizing the ALIGN program for comparing amino acid sequences, a PAM 120 weight residue table, a gap length penalty of 12, and a gap penalty of 4 is used when assessing percentage identity.

The term "conservative amino acid substitutions" refers to the substitution of an amino acid by another one of the same class, the classes being as follows:
Non-polar: Ala, Val, Leu, Ile, Pro, Met, Phe, Trp
Uncharged polar: Gly, Ser, Thr, Cys, Tyr, Asn, Gln
Acidic: Asp, Glu
Basic: Lys, Arg, His
Other conservative amino acid substitutions may also be made as follows:
Aromatic: Phe, Tyr, His
Proton Donor: Asn, Gln, Lys, Arg, His, Trp
Proton Acceptor: Glu, Asp, Thr, Ser, Tyr, Asn, Gln In the context of the present invention, the use of tropoelastin monomers is important because tropoelastin possesses particular properties such as elasticity, water-binding capabilities and cell-adhesion, which enables the formation of a hydrogel that is particularly strong, elastic and effective at encapsulating and preserving viable cells. In particular, the hydrogel is able to provide, at the tissue repair site, an environment that mimics the natural environment, thereby assisting in tissue repair and re-generation. It is also important that the tropoelastin monomer contains side chains or other functional groups that are exposed to enable, reaction with the acrylate. Examples of suitable side chains include lysine and arginine side chains. These are examples of amino acids that contain primary amine groups. Others include histidine and methionine.

One type of tropoelastin monomer may be used in the present invention, or combinations of different tropoelastin monomers may be used. For example, the combination of tropoelastin monomers can comprise 1, 2, 3, 4, 5, 6, 7, 9, 10, or more, different types of tropoelastin monomers. In another embodiment, at least 2, at least 3, at least 4, at least 5, at least 6, at least 7, at least 8, at least 9, at least 10 or more, different tropoelastin monomers can be used. In another embodiment, 1 or more, 2 or more, 3 or more, 4 or more, 5 or more, 6 or more, 7 or more, 8 or more, 9 or more, or 10 or more different types of tropoelastin monomers, can be used.

In addition, in other embodiments, the tropoelastin monomers are any number or combination of human and/or non-human (e.g. primate, bovine, equine, sheep, goat, pig, dog, cat, or rodent) tropoelastin monomers.

Further, it will be appreciated that varying the ratio and/or identity of each of the tropoelastin monomers present in a combination can generate tropoelastin-based hydrogels with desired elasticity, tensile strength, and shapeability, and that the strength, elasticity, cross-linking potential and other physical and biochemical behavior of tropoelastin polymers can therefore be varied, and possibly controlled, by incorporating various polymorphic forms of tropoelastin into polymeric scaffolds.

In another embodiment, the ratio and/or identity of each of the tropoelastin monomers present in a combination can be varied so as to match the tropoelastin monomers present in the tissue being repaired, replaced, or regenerated.

The present invention also relates to a tropoelastin comprising an acrylate group attached to at least one amine group of the tropoelastin. The tropoelastin may be a tropoelastin multimer comprised of two or more tropoelastin monomers.

As used herein, a "tropoelastin multimer" refers to two or more tropoelastin monomers that have been cross-linked to each other. Preferably, the two or more tropoelastin monomers have been enzymatically cross-linked (e.g. one or more amine groups of one monomer have been linked with one or more amine groups of another monomer by lysyl oxidase). In this embodiment, the tropoelastin multimer may be elastin. However, other cross-linking methods are also contemplated (such as cross-linking with glutaraldehyde, hyaluronic acid, etc).

A "tropoelastin multimer" may contain 2 or more, 3 or more, 4 or more, 5 or more, 6 or more, 7 or more, 8 or more, 9 or more, 10 or more, tropoelastin monomers. The multimer may contain dozens, or even hundreds, of tropoelastin monomers. The tropoelastin multimer may be composed of one type of tropoelastin monomer, or may contain more than one type of tropoelastin monomer. The tropoelastin monomers may be used in any of the ratios and combinations discussed above.

The present invention also relates to an acrylated tropoelastin formed by the process of treating tropoelastin with a compound comprising an acrylate group in conditions for attaching the acrylate group of the compound to an amine group of the tropoelastin.

The use of tropoelastin multimers is particularly advantageous where the acrylated tropoelastin multimers are to be used in an environment/application where fast formation of a hydrogel is desired. The present inventors have found that acrylated tropoelastin multimers, when applied to a tissue repair site that is to be sealed (i.e. where the hydrogel is required to function as a "glue"), form a gel very quickly when they are irradiated with light. Without wishing to be bound by theory, the inventors believe that this fast cross-linking is due to the fact that the tropoelastin is already in a multimeric form, which means that it has already formed a substantial portion of the cross-links that would otherwise need to be formed if tropoelastin monomers only were used. In this way, a biocompatible adhesive can be formed in a very quick manner and stick one tissue to another before the tissue can separate. This is particularly useful in post-surgery applications.

Such "sealant" or "adhesive" compositions should have the appropriate viscosity for application to a site. For example, where it is desired that the adhesive forms in an area that is uneven or that is comprised of a number of tissues or components that are not aligned, it may be more appropriate to use a composition that is more flowable (i.e. not very viscous). Alternatively, where more "grip" at the tissue repair site may be required to prevent the composition from slipping (such as in key-hole surgery applications), a higher viscosity composition will be required.

A person skilled in the art will be aware that the viscosity of the composition can be altered by changing the nature and the concentration of the tropoelastin used, as well as including viscosity-modifying additives (e.g. gelling agents) in the compositions, and will be aware how these factors can be altered to achieve the desired viscosity. A person skilled in the art will also be aware that the properties of the hydrogel formed from acrylated tropoelastin multimers can be changed by varying the concentration of acrylated tropoelastin multimers present in the composition, the degree of acrylation, the degree of cross-linking, and the like, as discussed herein. For example, the degree of acrylation can be varied between 10% to 50% by changing the concentration of methacrylic anhydride from 6 to 30% (v/v) during the acrylation. In addition, the concentration of acrylated tropoelastin can be changed from 5 to 25% (w/v). The degree of cross-linking can also be tuned by changing the UV exposure time from 10 sec to 180 sec.

As also discussed above, the hydrogels of the present invention form by cross-linking tropoelastin monomers or multimers with each other and then contacting the cross-linked tropoelastins with water. In order to effectively cross-link the tropoelastin, the inventors have modified the tropoelastin with acrylate moieties. This modification means that the tropoelastin monomers or multimers are able to bind to each other by photo-cross-linking of acrylated tropoelastin solution, using light (e.g. UV light) and a photoinitiator, to form hydrogels containing the cross-linked tropoelastins.

Accordingly, the hydrogels of the present invention are formed by modifying tropoelastin monomers or multimers with an acrylate (or a mixture of acrylates) and exposing the modified tropoelastin monomers or multimers to conditions for cross-linking the tropoelastins with each other via the acrylate moieties.

The acrylate group may or may not be provided in the form of a compound (such as a polymer) that includes the acrylate group as one component of the compound. Examples of such compounds include polymers including functional components such as those having water-binding activity enabling hydrogel formation (for example, PEG, GAG).

A person skilled in the art will be aware of the types of acrylates that would be suitable modifiers for tropoelastin. The term "acrylate" is used in the broadest sense and, in most cases, refers to derivatives of acrylic acids of formula (I): $R^1CHC(R^2)C(O)OR^3$, wherein $R^1$, $R^2$ and $R^3$ are independently H, $C_1$-$C_{10}$ alkyl, $C_2$-$C_{10}$ alkenyl, $C_2$-$C_{10}$ alkynyl, cycloalkyl, heterocycloalkyl, aryl or heteroaryl, each of which is optionally substituted. In some cases, the term "acrylate" refers to derivatives of formula (II): $R^1CHC(R^2)OR^3$. Further, the backbone of the alkyl, alkenyl or alkynyl can be interspersed with one or more of O, S, or NH. This is known as a "heteroalkyl" group. In some embodiments, $R^1$ can be H, methyl, ethyl or propyl.

Compounds are generally described herein using standard nomenclature. For compounds having asymmetric centres, it will be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z and E forms, with all isomeric forms of the compounds being included in the present invention unless otherwise specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulae provided herein, which have one or more stereogenic centres, have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors, biosynthesis (for example, using modified CYP102 such as CYP BM-3) or by resolution of the racemates, for example, enzymatic resolution or resolution by conventional methods such as crystallization in the presence of a resolving agent, or chromatography, using, for example, a chiral HPLC column.

Certain compounds are described herein using a general formula that includes variables such as $R^1$ and $R^2$. Unless otherwise specified, each variable within such a formula is defined independently of any other variable, and any variable that occurs more than one time in a formula is defined independently at each occurrence. Therefore, for example, if a group is shown to be substituted with 0, 1 or 2 R*, the group may be unsubstituted or substituted with up to two R* groups and R* at each occurrence is selected independently from the definition of R*. Also, combinations of substituents and/or variables are permissible only if such combinations result in stable compounds, i.e., compounds that can be isolated, characterized and tested for biological activity.

The term "alkyl" refers to a saturated, straight-chain or branched hydrocarbon group that contains from 1 to 10 carbon atoms, preferably from 1 to 6, i.e. 1, 2, 3, 4, 5, or 6, carbon atoms. Specific examples of alkyl groups are methyl, ethyl, propyl, iso-propyl, n-butyl, iso-butyl, sec-butyl, tert-butyl, n-pentyl, iso-pentyl, n-hexyl and 2,2-dimethylbutyl.

The term "heteroalkyl" refers to an alkyl group as defined above that contains one or more heteroatoms selected from oxygen, nitrogen and sulphur (especially oxygen and nitrogen). Specific examples of heteroalkyl groups are methoxy, trifluoromethoxy, ethoxy, n-propyloxy, iso-propyloxy, butoxy, tert-butyloxy, methoxymethyl, ethoxymethyl, —$CH_2CH_2OH$, —$CH_2OH$, methoxyethyl, 1-methoxyethyl, 1-ethoxyethyl, 2-methoxyethyl or 2-ethoxyethyl, methylamino, ethylamino, propylamino, iso-propylamino, dimethylamino, diethylamino, iso-propyl-ethylamino, methylamino methyl, ethylamino methyl, di-iso-propylamino ethyl, methylthio, ethylthio, iso-propylthio, enol ether, dimethylamino methyl, dimethylamino ethyl, acetyl, propionyl, butyryloxy, acetyloxy, methoxycarbonyl, ethoxy-carbonyl, propionyloxy, acetylamino, propionylamino, carboxymethyl, carboxyethyl or carboxypropyl, N-ethyl-N-methylcarbamoyl and N-methylcarbamoyl. Further examples of heteroalkyl groups are nitrile, iso-nitrile, cyanate, thiocyanate, iso-cyanate, iso-thiocyanate and alkylnitrile groups.

The term "alkenyl" refers to an at least partially unsaturated, straight-chain or branched hydrocarbon group that contains from 2 to 10 carbon atoms, preferably from 2 to 6, i.e. 2, 3, 4, 5 or 6, carbon atoms. Specific examples of alkenyl groups are ethenyl (vinyl), propenyl (allyl), iso-propenyl, butenyl, ethinyl, propinyl, butinyl, acetylenyl, propargyl, iso-prenyl and hex-2-enyl group. Alkenyl groups may have more than one double bond.

The term "alkynyl" refers to an at least partially unsaturated, straight-chain or branched hydrocarbon group that contains from 2 to 10 carbon atoms, preferably from 2 to 6, i.e. 2, 3, 4, 5 or 6, carbon atoms. Specific examples of alkynyl groups are ethynyl, propynyl, butynyl, acetylenyl and propargyl groups. Alkynyl groups may have more than one triple bond.

The term "cycloalkyl" refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. Specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0] nonyl, tetraline, adamantane (i.e. tricycle[$3.3.1.1^{3,7}$]decane), cyclopentylcyclohexyl and cyclohex-2-enyl.

The term "heterodycloalkyl" refers to a cycloalkyl group as defined above in which one or more (preferably 1, 2 or 3) ring carbon atoms, each independently, have been replaced by an oxygen, nitrogen, silicon, selenium, phosphorus or sulfur atom (preferably by an oxygen, sulfur or nitrogen atom). A heterocycloalkyl group has preferably 1 or 2 rings containing from 3 to 10 (especially 3, 4, 5, 6 or 7) ring atoms (preferably selected from C, O, N and S). Specific examples are piperidyl, prolinyl, imidazolidinyl, piperazinyl, morpholinyl, urotropinyl, pyrrolidinyl, tetra-hydrothiophenyl, tetrahydropyranyl, tetrahydrofuryl and 2-pyrazolinyl group and also lactames, lactones, cyclic imides and cyclic anhydrides.

The term "aryl" refers to an aromatic group that contains one or more rings containing from 6 to 14 ring carbon atoms, preferably from 6 to 10 (especially 6) ring carbon atoms. Examples are phenyl, naphthyl and biphenyl groups.

The term "heteroaryl" refers to an aromatic group that contains one or more rings containing from 5 to 14 ring atoms, preferably from 5 to 10 (especially 5 or 6) ring atoms, and contains one or more (preferably 1, 2, 3 or 4) oxygen, nitrogen, phosphorus or sulfur ring atoms (preferably O, S or N). Examples are pyridyl (for example, 4-pyridyl), imidazolyl (for example, 2-imidazolyl), phenylpyrrolyl (for example, 3-phenylpyrrolyl), thiazolyl, iso-thiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (for example, 3-pyrazolyl) and iso-quinolinyl groups.

The expression "halogen" or "halogen atom" as preferably used herein means fluorine, chlorine, bromine, or iodine.

A "substituent" as used herein, refers to a molecular moiety that is covalently bonded to an atom within a molecule of interest. For example, a "ring substituent" may be a moiety such as a halogen, alkyl group or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated and characterized. When a substituent is oxo, i.e., =O, then two hydrogens on the atom are replaced. An oxo group that is a substituent of an aromatic carbon atom results in a conversion of —CH— to —C(=O)— and a loss of aromaticity. For example a pyridyl group substituted by oxo is a pyridone. Examples of suitable substituents are alkyl, heteroalkyl, halogen (for example, fluorine, chlorine, bromine or iodine atoms), OH, =O, SH, $NH_2$, NHalkyl, =NH, $N_3$ and $NO_2$ groups.

The term "optionally substituted" refers to a group in which one, two, three or more hydrogen atoms have been replaced independently of each other by halogen (for example, fluorine, chlorine, bromine or iodine atoms) or by OH, =O, SH, $NH_2$, NH alkyl, =NH, $N_3$ or $NO_2$ groups. This expression also refers to a group that is substituted by one, two, three or more (preferably unsubstituted) alkyl, alkenyl, alkynyl, heteroalkyl, cycloalkyl, heterocycloalkyl, aryl, heteroaryl groups.

As used herein a wording defining the limits of a range of length such as, for example, "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

In the compounds of formula (I), $R^2$ can be H, methyl, ethyl or propyl. The term "methacrylate" usually refers to a specific acrylate derivative of formula (Ia): $CH_2C(CH_3)C(O)O^-$, i.e., an acrylate of formula (I) when $R^1$ is H and $R^2$ is methyl. Examples of suitable acrylates for use in the present invention are methyl acrylate, ethyl acrylate, 2-chloroethyl vinyl ether, 2-ethylhexyl acrylate, hydroxyethyl methacrylate, butyl acrylate, butyl methacrylate and trimethylolpropane triacrylate.

When the acrylate group is linked with a tropoelastin monomer or multimer, it is of formula (III): $R^1CHC(R^2)C(O)$—, or formula (IV): $R^1CHC(R^2)OR^3$—. Therefore, a methacrylate group linked with a tropoelastin monomer or multimer is of formula (Ma): $CH_2C(CH_3)C(O)$—. An acrylate group can be attached to a tropoelastin monomer or multimer by an ester or amide linkage. Further, the acrylate group can be linked to any position in a tropoelastin monomer or multimer. For example, an acrylate group can be linked to the N-terminus, the C-terminus, and/or at one or more of the sidechains of the amino acids of a tropoelastin monomer or multimer. In some embodiments, the acrylate group is linked to the side-chain amino group of a lysine residue by an amide linkage. Tropoelastin monomers and multimers can be modified with acrylate using any available means. For example, tropoelastin monomers and multimers can be acrylated by the addition of an acrylate anhydride to a tropoelastin solution in buffer, and allowed to react for a sufficient period of time and at an appropriate temperature. A procedure such as this is described in Example 1, and other suitable acrylating procedures are described in Annabi et al. (2009) and Annabi et al. (2010).

The present inventors have also discovered that properties of the hydrogels, of the present invention can be controlled by controlling the degree of tropoelastin acrylation. In order to produce a hydrogel in accordance with the present invention, a person skilled in the art will understand that the acrylate moieties need to be present in the tropoelastin monomer or multimer in proportions that are sufficient to cross-link the modified tropoelastins, such that a hydrogel can be formed in the presence of water.

Generally, the degree of acrylation can be understood based on the premise that one acrylate molecule will form one amide bond with a primary nitrogen-containing sidechain (for example, a lysine side-chain) of a tropoelastin monomer or multimer. Accordingly, the degree of acrylation can be based on the number of available amino groups in the tropoelastin molecules available for modification with acrylate groups.

As used herein, the degree of acrylation is defined as: (the number of acrylated lysines/total lysines in the tropoelastin monomer or multimer)×100. Accordingly, the degree of acrylation can range from about 1% (where, for example, 1 out of every 100 lysine groups is acrylated) to about 100% (i.e., where all available lysine groups are acrylated).

Generally, tropoelastin comprises 35 lysine residues per monomer. For the tropoelastin monomer used in the Examples, suitable degrees of acrylation were found to be about 31%, 44% or 48%. In one embodiment, the degree of acrylation of the tropoelastin monomer is from about 5% to about 90%, from about 10% to about 80%, from about 15% to about 75%, from about 20% to about 60%, from about 25% to about 55%, or from about 30% to about 50%. For example, the degree of acrylation may be about 5%, about 10%, about 15%, about 20%, about 25%, about 30%, about 35%, about 40%, about 45%, about 50%, about 55%, about 60%, about 65%, about 70%, about 75%, about 80%, about 85% or about 90%. The degree of acrylation for multimers that is suitable is the same as that given for monomers.

In one embodiment, from about 5% to about 90% of the lysine residues of the monomer are attached to an acrylate group. For example, from about 15% to about 75% (for example, from about 30% to about 50%) of the lysine residues of the monomer may be attached to an acrylate group. For example, about 5%, about 10%, about 15%, about 20%, about 25%, about 30%, about 35%, about 40%, about 45%, about 50%, about 55%, about 60%, about 65%, about 70%, about 75%, about 80%, about 85% or about 90% of the lysine residues of the monomer are attached to an acrylate group. The percentage of lysine residues attached to an acrylate group that is suitable for multimers is the same as that given for monomers.

For other tropoelastin monomers and multimers, the degree of acrylation required will depend on factors such as the length of the tropoelastin monomer or multimer, the number of lysine residues present in the monomer or multimer, the number and size of hydrophobic regions present in the monomer or multimer, and the concentration of acrylated monomer or multimer in the composition in which cross-linking occurs.

In certain embodiments, a lower degree of acrylation (i.e. lower than 30%) may be useful where a higher concentration of the acrylated tropoelastin will be used to form a hydrogel.

The present invention also relates to a composition comprising a tropoelastin monomer comprising an acrylate group attached to at least one amine group of the monomer. The present invention also relates to a composition comprising an acrylated tropoelastin monomer formed by the process of treating a tropoelastin monomer with a compound comprising an acrylate group in conditions for attaching the acrylate group of the compound to an amine of the tropoelastin monomer.

The present invention also relates to a composition comprising cross-linked tropoelastin, the cross-linked tropoelastin comprising:
  a plurality of tropoelastin monomers;
  a linker in the form of an acrylate group for cross-linking the monomers.

The present invention further relates to a composition comprising cross-linked tropoelastin formed by the process of cross-linking an above-described tropoelastin monomer comprising an acrylate group.

The present invention also relates to a process for forming a composition suitable for forming a hydrogel, the process including:
  providing an aqueous solution including acrylated tropoelastin monomers;
  subjecting the aqueous solution to conditions for cross-linking the acrylated tropoelastin monomers,
  thereby producing the composition.

The present invention also relates to a composition comprising a tropoelastin comprising an acrylate group attached to at least one amine group of the tropoelastin. A composition comprising an acrylated tropoelastin may be formed by the process of treating a tropoelastin with a compound comprising an acrylate group in conditions for attaching the acrylate group of the compound to an amine of the tropoelastin.

The present invention also relates to a composition comprising cross-linked tropoelastin, the cross-linked tropoelastin comprising:
  a plurality of tropoelastin multimers;
  a linker in the form of a compound having an acrylate group, wherein the acrylate group of the compound is attached to an amine group of the tropoelastin for cross-linking the multimers.

The present invention also relates to a composition comprising cross-linked tropoelastin formed by the process of cross-linking a tropoelastin multimer as discussed above.

The term "composition" as used herein may be a solid (e.g. powder) or a liquid composition containing the components mentioned above. In some embodiments, other components, such as one or more pharmaceutically acceptable excipients, one or more therapeutic agents, as well as any of the other additives (swelling agents, extra-cellular matrix proteins, and the like) discussed herein, to assist in the repair and/or restoration of the target tissue (and/or to a method of achieving targeted delivery of therapeutic compounds), will also be included in the compositions of the present invention. A powder composition may be reconstituted or converted to a hydrogel by exposure to an aqueous environment. For example, the powdered composition may be added to a mold, followed by addition of an aqueous solution (such as a buffer or saline solution). The powdered composition may also be provided directly to the tissue repair site, where it will absorb water from the surrounding environment to form a hydrogel at the site, and/or may be provided to the site, followed by addition of an aqueous solution to the composition to form the hydrogel in situ.

The composition may also comprise acrylated tropoelastin and an aqueous solution, which is then cross-linked, either in a mold or in situ, to provide the desired hydrogel.

In general, the amount of cross-linked tropoelastin in the composition of the present invention is an amount that allows for the formation of hydrogels in accordance with the present invention. In some embodiments, the amount of cross-linked tropoelastin in the composition of the present invention ranges between about 1% w/w and about 90% w/w, between about 2% w/w and about 80% w/w, between about 4% w/w and about 70% w/w, between about 5% w/w and about 60% w/w, between about 5% w/w and about 50% w/w, between about 6% w/w and about 40% w/w, between about 7% w/w and about 30% w/w or between about 8% w/w and about 20% w/w. In some embodiments, the amount of cross-linked tropoelastin is about 1% w/w, about 2% w/w, about 3% w/w, about 4% w/w, about 5% w/w, about 6% w/w, about 7% w/w, about 8% w/w, about 9% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w or more. In some embodiments, the amount of cross-linked tropoelastin is approximately 85% w/w. As a general rule, the solidity of the hydrogel increases with higher cross-linked tropoelastin concentrations in the composition.

In general, the amount of acrylated tropoelastin in the composition of the present invention is an amount that allows for the formation of hydrogels in accordance with the present invention. In some embodiments, the amount of acrylated tropoelastin in the composition of the present invention ranges between about 1% w/w and about 90% w/w, between about 2% w/w and about 80% w/w, between about 4% w/w and about 70% w/w, between about 5% w/w and about 60% w/w, between about 5% w/w and about 50% w/w, between about 6% w/w and about 40% w/w, between about 7% w/w and about 30% w/w or between about 8% w/w and about 20% w/w. In some embodiments, the amount of acrylated tropoelastin is about 1% w/w, about 2% w/w, about 3% w/w, about 4% w/w, about 5% w/w, about 6% w/w, about 7% w/w, about 8% w/w, about 9% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w or more. In some embodiments, the amount of acrylated tropoelastin is approximately 85% w/w. As a general rule, the solidity of the hydrogel increases with higher acrylated tropoelastin concentrations in the composition.

In another embodiment, no other polypeptide or protein is used in combination with, or linked to, the tropoelastin monomer. That is, in one embodiment, the composition of the present invention consists of, or consists essentially of, a tropoelastin monomer comprising an acrylate group attached to at least one amine group of the monomer. The present invention also relates to a composition consisting of, or consisting essentially of, an acrylated' tropoelastin monomer formed by the process of treating a tropoelastin monomer with a compound comprising an acrylate group in conditions for attaching the acrylate group of the compound to an amine of the tropoelastin monomer.

The present invention also relates to a composition consisting of, or consisting essentially of, cross-linked tropoelastin, the cross-linked tropoelastin comprising:
a plurality of tropoelastin monomers;
a linker in the form of an acrylate group, wherein the acrylate group of the compound is attached to an amine group of the tropoelastin for cross-linking the monomers.

The present invention therefore also relates to a composition consisting of, or consisting essentially of, cross-linked tropoelastin formed by the process of cross-linking a tropoelastin monomer of the present invention. The present invention therefore also relates to a hydrogel comprising a composition consisting of, or consisting essentially of, cross-linked tropoelastin monomers.

Where tropoelastin is present in the form of a multimer, in one embodiment, no other polypeptide or protein is used in combination with, or linked to, the tropoelastin. That is, in one embodiment, the composition of the present invention consists of, or consists essentially of, tropoelastin comprising an acrylate group attached to at least one amine group of the tropoelastin. In another embodiment, the present invention relates to a composition consisting of, or consisting essentially of, an acrylated tropoelastin formed by the process of treating a tropoelastin with a compound comprising an acrylate group in conditions for attaching the acrylate group of the compound to an amine of the tropoelastin.

The present invention also relates to a composition consisting of, or consisting essentially of, cross-linked tropoelastin, the cross-linked tropoelastin comprising:
a plurality of tropoelastin multimers;
a linker in the form of a compound having an acrylate group, wherein the acrylate group of the compound is attached to an amine group of the tropoelastin for cross-linking the multimers.

The present invention also relates to a composition consisting of, or consisting essentially of, cross-linked tropoelastin formed by the process of cross-linking a tropoelastin as discussed above.

The present invention also relates to a composition consisting of, or consisting essentially of, cross-linked tropoelastin, the cross-linked tropoelastin comprising:
a plurality of tropoelastins;
a linker in the form of a compound having an acrylate group, wherein the acrylate group of the compound is attached to an amine group of the tropoelastin, for cross-linking the tropoelastins.

The present invention also relates to a hydrogel comprising a composition as described above, as well as a device, support or scaffold (such as a graft, stent or implant) comprising the hydrogel. The device, support or scaffold may also include the composition (which is subsequently treated with, for example, an aqueous solution, to form a hydrogel). In one embodiment, the device, scaffold or support may comprise the acrylated tropoelastin, which is subsequently cross-linked and then treated (e.g. exposed to an aqueous environment) to form the hydrogel.

The present invention also relates to a hydrogel comprising a cross-linked network of acrylated tropoelastin. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels are superabsorbent.

Any amount of acrylated tropoelastin can be present in the hydrogel, provided that it is sufficient to form a hydrogel having functional characteristics described herein. For example, depending on the amount of acrylation, the hydrogel can comprise acrylated tropoelastin in the amount of about 1% (w/v) to about 95% (w/v). In some embodiments, the hydrogel can comprise acrylated tropoelastin in an amount of about 5% (w/v) to about 75% (w/v), about 10% (w/v) to about 50% (w/v), about 15% (w/v) to about 40% (w/v) or about 20% (w/v) to about 30% (w/v). In some embodiments, the hydrogel can comprise acrylated tropoelastin in the amount of about 1% (w/v) to about 20% (w/v). In some embodiments, the hydrogel can comprise acrylated tropoelastin in the amount of about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v) or about 15% (w/v). For example, the hydrogel can comprise acrylated tropoelastin in an amount of about 5% (w/v), about 10% (w/v) or about 15% (w/v).

In one embodiment, the invention provides a hydrogel, wherein:
from about 30% to about 50% of the lysine residues of a tropoelastin monomer are attached to an acrylate group; and
the concentration of acrylated tropoelastin monomer in the hydrogel is from about 5 to about 15% (w/v).

In one embodiment, the invention provides a hydrogel, wherein:
from about 30% to about 50% of the lysine residues of a tropoelastin multimer are attached to an acrylate group; and
the concentration of acrylated tropoelastin multimer in the hydrogel is from about 5 to about 15% (w/v).

In another embodiment, the invention provides a hydrogel, wherein:
from about 30% to about 50% of the lysine residues of a tropoelastin are attached to an acrylate group; and
the concentration of acrylated tropoelastin in the hydrogel is from about 5 to about 15% (w/v).

In one embodiment, about 30 to 35% of lysine residues are attached to an acrylate group and the concentration of the acrylated tropoelastin in the hydrogel is 5% or 10% or 15% (w/v).

In one embodiment, about 40 to 45% of lysine residues are attached to an acrylate group and the concentration of the acrylated tropoelastin in the hydrogel is 5% or 10% or 15% (w/v).

In one embodiment, about 45 to 50% of lysine residues are attached to an acrylate group and the concentration of the acrylated tropoelastin in the hydrogel is 5% or 10% or 15% (w/v).

In one embodiment, the hydrogel does not include a protein or polypeptide other than tropoelastin.

As mentioned above, without wishing to be bound by any theory, the degree of cross-linking in the hydrogel can also affect its properties. It will be understood by a person skilled in the art that the majority of acrylated groups will be cross-linked after exposure of the acrylated tropoelastin to UV light but it is unlikely that 100% cross-linking will be achieved. One reason for this is that accessibility to some of the free groups will be more restricted as cross-linking increases. The amount of cross-linking is directly correlated to the acrylation degree (higher acrylation leads to higher cross-linking density) but it is not the only factor that affects cross-linking degree. Other factors include UV exposure time, polymer concentration and photoinitator concentration.

Acrylated tropoelastin monomer or multimer can be cross-linked using any means available to one of skill in the art for polymerizing acrylate groups. The preferred method is to use light-initiated polymerisation (for example, by exposure to UV light). In certain embodiments, the intensity of light ranges from about 500 to about 10,000 $\mu W/cm^2$. In some embodiments, the intensity of light is about 4000, about 5000, about 6000, about 7000, about 8000, or about 9000 $\mu W/cm^2$. In some embodiments, the intensity of the light is about 5 $mW/cm^2$ to about 7.5 $mW/cm^2$. In some embodiments, the intensity of the light is between about 6 and about 7 $mW/cm^2$ (for example, 6.5 or 6.6 $mW/cm^2$). Light can be applied to the acrylated tropoelastin monomer solution for about 10 seconds to about 5 minutes. In certain embodiments, light is applied for about 10 to about 60 seconds. In some embodiments, light is applied for about 10 to about 30 seconds. In some embodiments, light is applied for about 20 to about 40 seconds. In some embodiments, light is applied for about 35 seconds. The light source may allow variation of the wavelength of light and/or the intensity of the light. Useful light sources include, but are not limited to, lamps and fiber optic devices.

Generally, the hydrogels described herein are porous, i.e., the hydrogels have porosity. As used herein, the term "porosity" means the fractional volume (dimension-less) of the composition that is composed of open space, for example, pores or other openings. Therefore, porosity measures void spaces in a material and is a fraction of volume of voids over the total volume, as a percentage between 0 and 100% (or between 0 and 1) (see, for example, Coulson et al. (1978)). Determination of matrix porosity is well known to a skilled artisan, for example, using standardized techniques, such as mercury porosimetry and gas adsorption (such as nitrogen adsorption). Generally, porosity of the hydrogel can range from 0.5 to 0.99, from about 0.75 to about 0.99, or from about 0.8 to about 0.95. Preferably, porosity of the porous material is at least 0.75, more preferably at least 0.8, and most preferably at least 0.9.

The porous hydrogels can have any pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, the hydrogel can be swollen when the hydrogel is hydrated. The sizes of the pores size can then change depending on the water content in the hydrogel. The pores can be filled with a fluid such as water or air. In some embodiments, the pores of the hydrogel can have a pore size distribution ranging from about 50 nm to about 1000 $\mu m$, from about 250 nm to about 500 $\mu m$, from about 500 nm to about 250 $\mu m$, from about 1 $\mu m$ to about 200 $\mu m$, from about 10 $\mu m$ to about 150 $\mu m$, from about 15 $\mu m$ to about 125 $\mu m$, from about 20 $\mu m$ to about 100 $\mu m$, or from about 40 $\mu m$ to about 65 $\mu m$. In some embodiments, the hydrogel can have a pore size of about 10 m, about 11 $\mu m$, about 12 $\mu m$, about 13 $\mu m$, about 14 $\mu m$, about 15 about 16 $\mu m$, about 17 $\mu m$, about 18 $\mu m$, about 19 $\mu m$, about 20 $\mu m$, about 21 $\mu m$, about 22 $\mu m$, about 23, $\mu m$, about 24 $\mu m$, about 25 $\mu m$, about 26 $\mu m$, about 27 $\mu m$, about 28 $\mu m$, about 29 $\mu m$, about 30 $\mu m$, about 31 $\mu m$, about 32 $\mu m$, about 33 $\mu m$, about 34 $\mu m$, about 35 $\mu m$, about 36 $\mu m$, about 37 $\mu m$, about 38 $\mu m$, about 39 $\mu m$, about 40 $\mu m$, about 41 $\mu m$, about 42 $\mu m$, about 43 $\mu m$, about 44 $\mu m$, about 45 $\mu m$, about 46 $\mu m$, about 47 $\mu m$, about 48 $\mu m$, about 49 $\mu m$, about 50 $\mu m$, about 51 $\mu m$, about 52 $\mu m$, about 53 $\mu m$, about 54 $\mu m$, about 55 $\mu m$, about 56 $\mu m$, about 57 $\mu m$, about 58 $\mu m$, about 59 $\mu m$, about 60 $\mu m$, about 61 $\mu m$, about 62 $\mu m$, about 63 $\mu m$, about 64 $\mu m$ or about 65 $\mu m$. In some embodiments, the hydrogel can have a pore size of between 11 and 12 $\mu m$ (for example, 11.7±3.3 $\mu m$), between 17 and 30 $\mu m$ (for example, 23.4±5.8 $\mu m$), or between 40 and 60 $\mu m$ (for example, 51±9 $\mu m$).

It will be understood by a person skilled in the art that pores can exhibit a distribution of sizes around the indicated "size". Unless otherwise stated, the term "size" as used herein refers to the mode of a size distribution of pores, i.e., the value that occurs most frequently in the size distribution.

The pores can be substantially round in cross-section or opening. What is meant by "substantially round" is that the ratio of the lengths of the longest to the shortest perpendicular axes of the pore cross-section is less than or equal to about 1.5. Substantially round does not require a line of symmetry. In some embodiments, the ratio of lengths between the longest and shortest axes of the pore cross-section is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1.

Advantageously, the hydrogels of the present invention are elastic. An "elastic" material is one that returns to a particular shape or conformation after a force such as compression or extension that has been applied to it has been withdrawn. It is also referred to as resiliently compressible and extendible, mechanically durable or pliable material of relatively low hysteresis. This material may be referred to as stretchable, tensile, resilient or capable of recoil. For example, the hydro gels can have an extensibility of about 500%, about 400%, 300%, 200%, or about 100%.

In some embodiments, the hydrogel can have an elastic modulus in the range about $10^{-2}$ kPa to about $10^3$ kPa. As used herein, the term "elastic modulus" refers to an object or substance's tendency to be deformed elastically (i.e., non-permanently) when a force is applied to it. Generally, the elastic modulus of an object is defined as the slope of its stress-strain curve in the elastic deformation region. Specifying how stress and strain are to be measured, including directions, allows for many types of elastic moduli to be defined. Young's modulus (E) describes tensile elasticity, or the tendency of an object to deform along an axis when opposing forces are applied along that axis; it is defined as the ratio of tensile stress to tensile strain. It is Often referred to simply as the elastic modulus. The bulk modulus (K) describes volumetric elasticity, or the tendency of an object to deform in all directions when uniformly loaded in all directions; it is defined as volumetric stress over volumetric strain, and is the inverse of compressibility. The bulk modulus is an extension of Young's modulus to three dimensions. Three other elastic moduli are Poisson's ratio, Lame's first parameter, and P-wave modulus. In some embodiments, the hydrogel can have an elastic modulus in the range from about 1 kPa to about 25 kPa. In some embodiments, the hydrogel can have an elastic modulus of about 5 kPa, about 6 kPa, about 7 kPa, about 8 kPa, about 9 kPa, about 10 kPa, about 11 kPa, about 12 kPa, about 13 kPa, about 14 kPa, about 15 kPa, about 16 kPa, about 17 kPa, about 18 kPa, about 19 kPa, or about 20 kPa. In some embodiments, the hydrogel can have an elastic modulus between about 1 and about 4 kPa (for example, 2.8±0.6 kPa) or between about 13 and about 17 kPa (for example, 14.8±1.9 kPa).

In some embodiments, the hydrogel can have a dynamic modulus of from about 25 kPa to about 250 kPa. As used herein, the term "dynamic modulus" refers to the ratio of stress to strain under vibratory conditions. Dynamic modulus can be calculated from data obtained from either free or forced vibration tests, in shear, compression, or elongation.

Compressive strength is the capacity of a material or structure to withstand axially directed pushing forces. It provides data (or a plot) of force vs deformation for the conditions of the test method. By definition, the compressive strength of a material is that value of uni-axial compressive stress reached when the material fails completely. The compressive strength is usually obtained experimentally by means of a compressive test. The apparatus used for this experiment is the same as that used in a tensile test. However, rather than applying a uni-axial tensile load, a uni-axial compressive load is applied. As can be imagined, the specimen is shortened as well as spread laterally. Compressive strength is often measured on a universal testing machine; these range from very small table-top systems to ones with over 53 MN capacity. Measurements of compressive strength are affected by the specific test method and conditions of measurement.

Compressive strength of the hydrogels can be determined using cyclic loading at a given strain level (for example, 5%, 10%, 15%, 20%, 25%, 30%, 35%, 40%, 45%, 50%, 55%, 60%, 65%, 70% or 75% strain level). The compressive modulus of the hydrogels can range from about 1 kPa to about 500 kPa. In some embodiments, the compressive modulus of the hydrogel can be from about 5 kPa to about 250 kPa, from about 7.5 kPa to about 200 kPa, or from about 10 kPa to about 200 kPa. In some embodiments, the compressive modulus of the hydrogel can be about 5 kPa, about 6 kPa, about 7 kPa, about 7.5 kPa, about 8 kPa, about 9 kPa, about 10 kPa, about 11 kPa, about 12 kPa, about 13 kPa, about 14 kPa, about 15 kPa, about 16 kPa, about 17 kPa, about 18 kPa, about 19 kPa, about 20 kPa, about 21 kPa, about 22 kPa, about 23 kPa, about 24 kPa, about 25 kPa, about 26 kPa, about 27 kPa, about 28 kPa, about 29 kPa, about 30 kPa, about 31 kPa, about 32 kPa, about 33 kPa, about 34 kPa, about 35 kPa, about 36 kPa, about 37 kPa, about 38 kPa, about 39 kPa, about 40 kPa, about 41 kPa, about 42 kPa, about 43 kPa, about 44 kPa, about 45 kPa, about 46 kPa, about 47 kPa, about 48 kPa, about 49 kPa, about 50 kPa, about 60 kPa, about 70 kPa, about 75 kPa, about 80 kPa, about 85 kPa, about 90 kPa, about 95 kPa, about 100 kPa, about 105 kPa, about 110 kPa, about 115 kPa, about 120 kPa, about 125 kPa, about 130 kPa, about 135 kPa, about 140 kPa, about 145 kPa, about 150 kPa, about 155 kPa, about 160 kPa, about 165 kPa, about 170 kPa, or about 175 kPa. In some embodiments, the compressive modulus of the hydrogel can be between about 8 and about 10 kPa (for example, 8.8±0.4 kPa), between about 13 and about 16 kPa (for example, 14.8±1.1 kPa) or between about 150 and about 180 kPa (for example, 159.7±18.8 kPa).

Under compression, the hydrogels can lose energy. Energy loss can range from about 5% to about 50%. In some embodiments, energy loss can be from about 10% to about 40%, from about 20% to about 35% (for example, 23±3.2% or 24.1±7%), or from about 25% to about 30% (for example, 30.5±6.4 or 26.9±2.3). In some embodiments, the energy loss can be about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44% or 45%. In some embodiments, the energy loss can from about 35 to about 45% (for example, 40.5±3.9).

In one embodiment, the strain at break of the hydrogel between about 130 and about 420 kPa. For example, the strain at break may be about 130 kPa, about 140 kPa, about 150 kPa, about 160 kPa, about 170 kPa, about 180 kPa, about 190 kPa, about 200 kPa, about 210 kPa, about 220 kPa, about 230 kPa, about 240 kPa, about 250 kPa, about 260 kPa, about 270 kPa, about 280 kPa, about 290 kPa, about 300 kPa, about 310 kPa, about 320 kPa, about 330 kPa, about 340 kPa, about 350 kPa, about 360 kPa, about 370 kPa, about 380 kPa, about 390 kPa, about 400 kPa, about 410 kPa or about 420 kPa. In some embodiments, the strain at break may be between about 120 and about 150 kPa (for example, 134.9±11.1 kPa), between about 220 and about 325 kPa (for example, 272.7±49.7 kPa), between about 280 and about 380 kPa (for example, 331.7±47.6), between about 335 and about 415 kPa (for example, 375.6 f 38 kPa), or between about 410 and about 415 kPa (for example, 401.9±10.1 kPa). The strain at break test was performed by stretching samples until they broke and determining the strain at breaking point from the strain/stress curves.

The hydrogels described herein are also swellable. The term "swellable" refers to hydrogels that are substantially insoluble in a swelling agent and are capable of absorbing a substantial amount of the swelling agent, thereby increasing in volume when contacted with the swelling agent. As used herein, the term "swelling agent" refers to those compounds or substances which produce at least a degree of swelling. Typically, a swelling agent is an aqueous solution or organic solvent, however the swelling agent can also be a gas. In some embodiments, a swelling agent is water or a physiological solution, for example phosphate buffer saline, or growth media.

In some embodiments, the hydrogel comprises a swelling agent. In some embodiments, the hydrogel can contain over 50% (w/v), over 60% (w/v), over 70% (w/v), over 80% v, over 90% (w/v), over 91% (w/v), over 92% (w/v), over 93% (w/v), over 94% (w/v), over 95% (w/v), over 96% (w/v), over 97% v, over 98% (w/v), over 99% (w/v), or more of the swelling agent.

The term "swelling ratio" is used herein to mean weight of swelling agent in swollen hydrogel per the dried weight of the hydrogel before swelling. For example, the swelling ratio can range from about 1 to about 10 grams of swelling agent per gram of the tropoelastin in the hydrogel. In some embodiments, the swelling ratio can be from about 1 to about 5 grams of swelling agent per gram of the tropoelastin in the hydrogel. In some embodiments, the swelling ratio can be about 1.25, about 1.5, about 1.75, about 2, about 2.25, about 2.5, about 2.75, about 3, about 3.25, about 3.5, about 3.75, about 4, about 4.25, about 4.5, about 4.75 or about 5 grams of swelling agent per gram of tropoelastin in the hydrogel. In some embodiments, the swelling ratio can be 1.2±0.2, 2.3±0.3, or 4.1±0.3 grams of swelling agent per gram of tropoelastin in the hydrogel.

The hydrogels of the present invention also possess a high ultimate strength, which is usually defined as the maximum stress that a material can withstand while being stretched or pulled before the material's cross-section starts to significantly stretch. A person skilled in the art will be aware of suitable methods to test the ultimate strength of a material. The hydrogel of the present invention can have an ultimate strength ranging from about 10 to about 45 kPa (for example, about 12 to about 40 kPa). In one embodiment, the ultimate strength is about 10 kPa, about 11 kPa, about 12 kPa, about 13 kPa, about 14 kPa, about 15 kPa, about 16 kPa, about 17 kPa, about 18 kPa, about 19 kPa, about 20 kPa, about 21 kPa, about 22 kPa, about 23 kPa, about 24 kPa, about 25 kPa, about 26 kPa, about 27 kPa, about 28 kPa, about 29 kPa, about 30 kPa, about 31 kPa, about 32 kPa, about 33 kPa, about 34 kPa, about 35 kPa, about 36 kPa, about 37 kPa, about 38 kPa, about 39 kPa, about 40 kPa, about 41 kPa, about 42 kPa, about 43 kPa, about 44 kPa, or about 45 kPa. In one embodiment, the ultimate strength is 12.5±2.2 kPa, 23.8±7.5 kPa, 27.2±3.4 kPa, 29.4±5.7 kPa or 39.3±2.5 kPa.

The use of grooved substrates has been demonstrated in the literature to induce cell and ECM alignment upon various substrates. These methods have been employed in part as an effort to control tissue development. Most of the material substrates (i.e. titanium, silicone, PDMS and PEO) used in these studies are not readily degraded by the body or are not suitable for use in vivo. Therefore, while possible applications in tissue development have been explored with these substrates, the cultured cells grown upon the substrates cannot be implanted, significantly limiting their practical use. Furthermore, these materials may cause stress induced cell responses that may disrupt normal cell function and tissue development over time.

The hydrogel of the present invention may be a patterned hydrogel (e.g. a micropatterned hydrogel). Micropatterned hydrogels can be prepared using, for example, the method set forth in U.S. Pat. No. 6,423,252. For example, the method comprising contacting pre-polymer solution with a surface of a mold, the mold comprising on at least one surface thereof a three-dimensional negative configuration of a predetermined micropattern to be disposed on and integral with at least one surface of the hydrogel, and polymerizing the polymer in the solution while in contact with the micropatterned surface of the mold, thereby providing a micropatterned hydrogel. Hydrogels prepared this way comprise a predetermined and designed micropattern on at least one surface of the hydrogel, which pattern is effective to facilitate cell alignment, tissue repair, growth or regeneration, or is effective to provide delivery of a protein or a therapeutic agent. The micropattern geometry can be controlled using the molds of the appropriate pattern or size. Further, the micropattern can be characterized for surface morphology by known techniques, such as field emission scanning electron and atomic force microscopy. In some embodiments, the micropattern is designed to induce cell and/or ECM alignment.

In some embodiments, the micropattern is in the forms of grooves or channels. The groove size (width) can range from about 500 nm to about 500 μm. In some embodiments, the groove size can range from about 1 μm to about 250 μm, from about 10 μm to about 100 μm, or from about 20 μm to about 75 μm. In some embodiments, the groove size is about 50 μm or about 20 μm.

The spacing between the grooves can also be optimized for desired use. For example, spacing between the grooves can range from about 500 nm to about 500 μm. In some embodiments, the distance between the grooves can range from about 1 μm to about 250 μm, from about 10 μm to about 100 μm, or from about 20 μm to about 75 μm. In some embodiments, the distance between the grooves is about 50 μm or about 20 μm.

The groove thickness depth can range from about 250 nm to about 500 μm. In some embodiments, groove thickness can range from about 500 nm to about 250 μm, or from about 750 nm to about 1000 nm.

In some embodiments, the hydrogel is in the form of a film. The thickness of the film can range from nanometers to millimeters. For example, film thickness can range from about 1 nm to about 1000 mm. In some embodiments, the film thickness can be from about 1 nm to 1000 nm, from about 1 μm about 1000 μm, from about 1 mm to about 1000 mm. In some embodiments, the film thickness can be from about 500 nm to about 750 μm, from about 750 nm to about 500 μm, from about 1000 nm to about 250 μm, from about 10 μm to about 100 μm, from about 25 μm to about 75 μm. In some embodiments, film thickness ranges from about 10 nm to about 1 mm. In some embodiments, the film thickness can be about 50 μm.

In some embodiments, the hydrogel is a foam. Foams can be made from methods known in the art, including, for example, freeze-drying and gas foaming in which water is the solvent or nitrogen or other gas is the blowing agent, respectively.

In some embodiments, the hydrogel is a scaffold produced using a moulding process (see, for example, WO 03/004254 and WO 03/022319). Using such a process, for example, the pre-polymer solution is placed into a mould, the mould being a negative of the desired shape of the scaffold. The solution is polymerized and removed from the mould.

Hydrogels described herein can be manufactured using any available method. To give but one general example, a polymer precursor solution can be moulded using a stamp. Subsequently, the polymer precursor solution can be cross-linked and/or polymerized to form the hydrogel. The mould can then be removed to generate an array of micromoulded hydrogels that can be harvested into a solution using a simple wash.

Exemplary desired shapes of the hydrogel, include, but are not limited to sheets, tubes, any other three-dimensional shape. Hydrogels formed in the shape of a sheet can be used in the preparation of implants and grafts to provide reparative, replacement, and/or regenerative therapy for dermal tissues, membranes for tooth root coverage procedures, membranous tissues, and the like. Hydro gels formed in the shape of a tube can be used in the preparation of implants and grafts to provide reparative, replacement, and/or regenerative therapy for arteries, veins, ureters, urethras, nerves, long bones, and the like. Hydrogels formed in the shape of any other three-dimensional can be used in the preparation of implants and grafts to provide reparative, replacement, and/or regenerative therapy for organ transplants, bone remodeling or mending, dental implants, or for muscle, tendon, ligament, and cartilage grafts.

A biocompatible hydrogel formed, cast, or molded in the shape of a sheet, can be a flat sheet, or a sheet having curvatures to closely match the contours of the injured, damaged, or diseased tissue or organ being repaired, replaced, or regenerated. The sheets may be of any geometrical shape, including but not limited to squares, rectangles, trapezoids, triangles, circles, ellipses, and the like.

Exemplary areas of the sheets include areas of about 1 $mm^2$ to about 1 $m^2$, about 1 $mm^2$ to about 50 $cm^2$, about 1 $mm^2$ to about 25 $cm^2$, about 1 $mm^2$ to about 10 $cm^2$, about 1 $mm^2$ to about 1 $cm^2$, about 1 $cm^2$ to about 1 $m^2$, about 1 $cm^2$ 1 $cm^2$ to about 500 $cm^2$, 1 $cm^2$ to about 250 $cm^2$, 1 $cm^2$ to about 200 $cm^2$, 1 $cm^2$ to about 150 $cm^2$, to about 100 $cm^2$, about 1 $cm^2$ to about 50 $cm^2$, about 1 $cm^2$ to about 25 $cm^2$, about 1 $cm^2$ to about 10 $cm^2$, about 1 $cm^2$ to about 5 $cm^2$, about 1 $cm^2$ to about 2.5 $cm^2$, about 10 $mm^2$ to about 10 $cm^2$, about 0.1 $cm^2$ to about 10 $cm^2$, about 0.1 $cm^2$ to about 1 $cm^2$, or any intervening range thereof. For example, the range of areas of 1 $cm^2$ to 100 $cm^2$ of an exemplary sheet includes about areas of about 1 cm², about 5 cm², about 10 cm², about 20 cm², about 30 cm², about 40 cm², about 50 cm², about 60 cm², about 70 cm², about 80 cm², about 90 cm², and about 100 cm².

Exemplary degrees of thickness of a hydrogel formed, cast, or molded in the shape of a sheet, include a range of about 0.1 mm to about 10 mm, about 0.25 mm to about 7.5 mm, about 0.5 mm to about 5 mm, about 0.75 mm to about 2.5 mm, about 1 mm to about 2 mm or any intervening range thereof.

In another embodiment, the thickness can be about 0.1 mm, about 0.25 mm, about 0.5 mm, about 0.75 mm, about 1 mm, about 2 mm, about 3 mm; about 4 mm, about 5 mm, about 7.5 mm, or about 10 mm or more.

A hydrogel formed, cast, or molded in the shape of a tube, can have any desired length, diameter, and thickness such that the size of the scaffold is suitable to repair, replace, and/or regenerate an injured, damaged, or diseased tissue or organ. Exemplary lengths of the tube include about 0.5 cm, about 1 cm, about 2.5 cm, about 5 cm, about 10 cm, about 25 cm, about 50 cm, about 100 cm, about 150 cm, about 200 cm, about 250 cm, about 300 cm, about 350 cm, about 400 cm, about 450 cm, about 500 cm, or longer. Exemplary diameters of the tube include about 0 mm (e.g., a solid fiber), 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 11 mm, about 12 mm or more mm in diameter. In a preferred embodiment, a tube of the invention has about 1 mm to about 10 mm diameter.

A hydrogel formed, cast, or molded in the shape of other three-dimensional objects can have any desired volume and/or shape such that the size of the scaffold is suitable to repair, replace, and/or regenerate an injured, damaged, or diseased tissue or organ. As discussed above, the composition of the present invention can also be applied to a wound (for example, post-surgery), in which case the hydrogel formed at the wound site can act as an adhesive to seal the wound and facilate healing.

Exemplary volumes of the three-dimensional shape scaffolds of about 100 mm³ to about 5 m³, about 100 mm³ to about 1000 cm³, about 1 cm³ to about 1000 cm³, about 1 cm³ to about 100 cm³, about 1 cm³ to about 10 cm³, about 10 cm³ to about 1000 m³, about 10 cm³ to about 100 cm³, about 500 cm³ to about 1000 cm³, about 100 mm³ to about 5 cm³, about 100 mm³ to about 2.5 cm³, about 1 cm³ to about 5 cm³, about 1 cm³ to about 2.5 cm³, about 750 cm³ to about 1250 cm³, about 850 cm³ to about 1150 cm³, about 950 cm³ to about 1050 cm³, about 900 cm³ to about 1000 cm³, or any intervening range thereof. For example, the range of volumes of 1 cm³ 3 to 10 cm³ of an exemplary three dimensional shape includes about volumes of about 1 cm³, about 2 cm³, about 3 cm³, about 4 cm³, about 5 cm³, about 6 cm³, about 7 cm³, about 8 cm³, about 9 cm³, and about 10 cm³.

Any method known to one skilled in the art for cross-linking can be used for preparing the hydrogels. Without wishing to be bound by a theory, acrylate groups in the tropoelastin can be polymerized using photo-cross-linking methods. Only one or a combination of two or more photoinitiators can be used. Photoinitiators produce reactive free radical species that initiate the cross-linking and/or polymerization of monomers upon exposure to light. Any photoinitiator can be used in the cross-linking and/or polymerization reaction. Photoinitiated polymerizations and photoinitiators are discussed in detail in Rabek, Mechanisms of Photophysical Processes and Photochemical Reactions in Polymers, New York: Wiley & Sons, 1987; Fouassier, Photoinitiation, Photopolymerization, and Photocuring, Cincinnati, Ohio: Hanser/Gardner; Fisher et al., 2001, Annu. Rev. Mater. Res., 31:171. A photoinitiator can be designed to produce free radicals at any wavelength of light. For example, a photoinitiator can be designed to work using UV light (200-500 nm). The wavelength and intensity that can be used has been mentioned previously above.

In some embodiments, the photoinitiator can be a peroxide (for example, ROOR'), a ketone (for example, RCOR'), an azo compound (i.e. compounds with a —N=N— group), an acylphosphineoxide, a sulfur-containing compound, a quinone. Exemplary photoinitiators include, but are not limited to, acetophenone; anisoin; anthraquinone; anthraquinone-2-sulfonic acid, sodium salt monohydrate; (benzene) tricarbonylchromium; 4-(boc-aminomethyl)phenyl isothiocyanate; benzin; benzoin; benzoin ethyl ether; benzoin isobutyl ether; benzoin methyl ether; benzoic acid; benzophenyl-hydroxycyclohexyl phenyl ketone; 3,3',4,4'-benzophenonetetracarboxylic dianhydride; 4-benzoylbiphenyl; 2-benzyl-2-(dimethylamino)-4'-morpholinobutyrophenone; 4,4'-bis(diefhylamino)benzophenone; 4,4'-bis(dimethylamino)benzophenone; Michler's ketone; camphorquinone; 2-chlorothioxanthen-9-one; 5-dibenzosuberenone; (cumene) cyclopentadienyliron(II) hexafluorophosphate; dibenzosuberenone; 2,2-diefhoxyacetophenone; 4,4'-dihydroxybenzophenone; 2,2-dimethoxy2-phenylacetophenone; 4-(dimethylamino)benzophenone; 4,4'-dimethylbenzyl; 2,5-dimethylbenzophenone; 3,4-dimethylbenzophenone; diphenyl(2,4,6-trimethylbenzoyl)phosphine oxide; 2-hydroxy-2-methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methyl benzophenone; methybenzoylformate; 2-methyl-4'-(methylthio)-2-morpholinopropiophenone; 9,10-phenanthrenequinone; 4'-phenoxyacetophenone; thioxanthen-9-one; triarylsulfonium hexafluoroantimonate salts; triarylsulfonium hexafluorophosphate salts; 3-mercapto-1-propanol; 11-mercapto-1-undecanol; 1-mercapto-2-propanol; 3-mercapto-2-butanol; hydrogen peroxide; benzoyl peroxide; 4,4'-dimethoxybenzoin; 2,2-dimethoxy-2-phenylacetophenone; dibenzoyl disulphides; diphenyldithiocarbonate; 2,2'-azobisisobutyronitrile (AIBN); camphorquinone (CQ); eosin; dimethylaminobenzoate (DMAB); dimethoxy-2-phenyl-acetophenone (DMPA); Quanta-cure ITX photosensitizes (Biddle Sawyer); Irgacure 907 (Ciba Geigy); Irgacure 2959 (CIBA Geigy); Irgacure 651 (Ciba Geigy); Darocur 2959 (Ciba Geigy); ethyl-4-N,N-dimethylaminobenzoate (4EDMAB); 1-[-(4-benzoylphenylsulfanyl)phenyl]-2-methyl-2-(4-methylphenylsulfonyl)propan1-one; 1-hydroxy-cyclohexyl-phenyl-ketone; 2,4,6trimethylbenzoyldiphenylphosphine oxide; diphenyl(2,4,6trimethylbenzoyl)phosphine; 2-ethylhexyl-4 dimethylaminobenzoate; 2-hydroxy-2-methyl-1-phenyl-1-propanone; 65% (oligo[2-hydroxy-2-methyl-1-[4-(1methylvinyl)phenyl]propanone] and 35% propoxylated glyceryl triacrylate; benzil dimethyl ketal; benzophenone; blend of benzophenone and a-hydroxy-cyclohexyl-phenylketone; blend of Esacure KIP150 and Esacure TZT; blend of Esacure KIP150 and Esacure TZT; blend of Esacure KIP150 and TPGDA; blend of phosphine oxide, Esacure KIP150 and Esacure TZT; difunctional a-hydroxy ketone; ethyl 4-(dimethylamino)benzoate; isopropyl thioxanthone; 2-hydroxy-2methyl-phenylpropanone; 2,4,6,-trimethylbenzoyldipheny- 1-phosphine oxide; 2,4,6-trimethyl benzophenone; liquid blend of 4-methylbenzophenone and benzophenone; oligo (2-hydroxy-2-methyl-1-(4(1-methylvinyl)phenyl)pro-panone; oligo(2-hydroxy-2-methyl-1-4(1-methylvinyl)phe-nyl propanone and 2-hydroxy-2-methyl-1-phenyl-1-propanone (monomeric); oligo(2-hydroxy-2-methyl-1-4(1-methylvinyl)phenyl propanone and 2-hydroxy-2-methyl-1-phenyl-1-propanone (polymeric); 4-methylbenzophenone; trimethylbenzophenone and methylbenzophenone; and water emulsion of 2,4,6-trimethylbenzoylphosphine oxide, alpha hydroxyketone, trimethylbenzophenone, and 4-methyl benzophenone. In certain embodiments, the photoinitiator is acetophenone; diphenyl(2,4,6-trimethylbenzoyl)phosphine oxide; 4,4'-dimethoxybenzoin; anthraquinone; anthraqui-none-2-sulfonic acid; benzene-chromium(O) tricarbonyl; 4-(boc-aminomethyl)phenyl isothiocyanate; benzil; ben-zoin; benzoin ethyl ether; benzoin isobutyl ether; benzoin methyl ether; benzophenone; benzoic acid; benzophenone/1 hydroxycyclohexyl phenyl ketone, 50/50 blend; benzophe-none-3,3',4,4'-tetracarboxylic dianhydride; 4-benzoylbiphe-nyl; 2-benzyl-2-(dimethyl amino)-4' morpholinobutyrophe-none; 4,4'-bis(diethylamino) benzophenone; Michler's ketone; (±)-camphorquinone; 2-chlorothioxanthen-9-one; 5-dibenzosuberenone; 2,2-diethoxyacetophenone; 4,4'-dihy-droxybenzophenone; 2,2-dimethoxy-2-phenylacetophe-none; 4-(dimethylamino)benzophenone; 4,4'-dimethylben-zil; 3,4dimethylbenzophenone; diphenyl (2,4,6-trimethylbenzoyl) phosphine oxide/2-hydroxy methylpropiophenone; 4'-ethoxyacetophenone; 2-ethylan-thraquinone; ferrocene; 3'-hydroxyacetophenone; 4'-hy-droxyacetophenone; 3-hydroxybenzophenone; 4-hydroxy-benzophenone; 1-hydroxycyclohexyl phenyl ketone; 2-hydroxy-2-methylpropiophenone; 2-methylbenzophe-none; 3-methylbenzophenone; methyl benzoylformate; 2-methyl-4'-(methylthio)-2-morpholinopropiophenone; 9,10-phenanthrenequinone; 4'-phenoxyacetophenone; thio-xanthen-9-one; triarylsulfonium hexafluorophosphate salts; 3-mercapto-1-propanol; 11-mercapto-1-undecanol; 1-mer-capto-2-propanol; and 3-mercapto-2-butanol, all of which are commercially available from Sigma-Aldrich. In certain embodiments, the free radical initiator is selected from the group consisting of benzophenone, benzyl dimethyl ketal, 2-hydroxy-2-methyl-phenylpropanone; 2,4,6-trimethylben-zoyldiphenyl phosphine oxide; 2,4,6-trimethyl benzophe-none; oligo(2-hydroxy-2-methyl-1 (4-(1-methylvinyl)phe-nyl)propanone and 4-methylbenzophenone. In some embodiments, the photoinitiator is dimethoxy-2-phenyl-ac-etophenone (DMPA), a titanocene, 2-hydroxy-1-(4(hy-droxyethoxy)phenyl)-2-methyl-1-propanone, Igracure. In some embodiments, the initiator is 2-hydroxy-1-(4-(hy-droxyethoxy)phenyl)-2-methyl-1-propanone (Irgacure 2959, CIBA Chemicals).

An initiator of a cationic or anionic cross-linking and/or polymerization process can be used. Exemplary photoini-tiators of cationic cross-linking and/or polymerization include, but are not limited to, titanium tetrachloride, vana-dium tetrachloride, bis(cyclopentadienyl)titanium dichlo-ride, ferrocene, cyclopentadienyl manganese tricarbonyl, manganese decacarbonyl, diazonium salts, diaryliodonium salts (for example, 3,3'-dinitrodiphenyliodonium hexafluo-roarsenate, diphenyliodonium fluoroborate, 4-methoxydi-phenyliodonium fluoroborate) and triarylsulfonium salts.

In general, photoinitiators are utilized at concentrations ranging between approximately 0.005% w/v and 5.0% w/v. For example, photoinitiators can be utilized at concentra-tions of about 0.005% w/v, about 0.01% w/v, about 0.025% w/v, about 0.05% w/v, about 0.075% w/v, about 0.1% w/v, about 0.125% w/v, about 0.25% w/v, about 0.5% w/v, about 0.75% w/v, about 1% w/v, about 1.125% w/v, about 1.25% w/v, about 1.5% w/v, about 1.75% w/v, about 2% w/v, about 2.125% w/v, about 2.25% w/v, about 2.5% w/v, about 2.75% w/v, about 3% w/v, about 3.125% w/v, about 3.25% w/v, about 3.5% w/v, about 3.75% w/v, about 4% w/v, about 4.125% w/v, about 4.25% w/v, about 4.5% w/v, about 4.75% w/v, about 5% w/v or higher, although high concentrations of photoinitiators can be toxic to cells.

Without wishing to be bound by theory, hydrogel char-acteristics or properties can be altered and/or controlled by altering photo-cross-linking conditions. For example, photo-cross-linking utilizing longer wavelengths tends to generate hydrogels with less toxicity. Photo-cross-linking for longer periods of time tends to generate hydrogels with stiffer mechanical properties, although higher doses of UV can be toxic to cells. Photo-cross-linking utilizing higher-power UV light tends to generate hydrogels with higher mechanical stiffnesses and more extensive cross-linking.

Methods other that photo-cross-linking can also be used for preparing the hydrogels. For example, cross-linking can be achieved utilizing chemical cross-linking agents, physical cross-linking methods (for example, repeated cycles of freezing and thawing can induce cross-linking of particular polymers), irradiative cross-linking methods, thermal cross-linking methods, ionic cross-linking methods, and the like.

In some embodiments, the gel can be functionalized with a binding molecule that binds with a molecule (i.e., a target molecule) to be encapsulated within the hydrogel. These binding molecules are also referred to as affinity molecules. The binding molecule can be bound covalently (directly or through a linker) or non-covalently to the matrix. The binding molecule can be selected such that it can bind to any part of the target molecule that is accessible.

As used herein, the term "binding molecule" or "affinity molecule" refers to any molecule that is capable of binding a target molecule. Representative examples of affinity mol-ecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (for example, insulin for the insulin receptor); and biological, chemical or other molecules that have affinity for another molecule, such as biotin and avidin. The binding molecules need not com-prise an entire naturally occurring molecule but may consist of only a portion, fragment or subunit of a naturally or non-naturally occurring molecule, as for example the Fab fragment of an antibody.

Nucleic acid-based binding molecules include aptamers. As used herein, the term "aptamer" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences com-prising nucleotides, ribonucleotides, deoxyribonucleotides, nucleotide analogs, modified nucleotides and nucleotides comprising backbone modifications, branchpoints and non-nucleotide residues, groups or bridges. Methods for select-ing aptamers for binding to a molecule are widely known in the art and easily accessible to one of ordinary skill in the art.

In some embodiments, the binding molecules can be polyclonal and/or monoclonal antibodies and antigen-binding derivatives or fragments thereof. Well-known antigen binding fragments include, for example, single domain antibodies (dAbs, which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings (Klein (1982), Clark, W. R. (1986) and Roitt, I. (1991)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

In some embodiments, the binding molecule binds with a cell. Without wishing to be bound by theory, a molecule that binds with a cell can do so by binding with a cell-surface marker or a cell-surface molecule. These binding molecules that bind with a cell are also referred to as cell binding molecules. In some further embodiments, the binding molecule binds with a cell-surface marker but does not cause initiation of downstream signaling event mediated by that cell-surface marker. Binding molecules specific for cell-surface molecules include, but are not limited to, antibodies or fragments thereof, natural or recombinant ligands, small molecules, nucleic acids and analogues thereof, intrabodies, aptamers, lectins, and other proteins or peptides.

As used herein, a "cell-surface marker" refers to any molecule that is present on the outer surface of a cell. Some molecules that are normally not found on the cell-surface can be engineered by recombinant techniques to be expressed on the surface of a cell. Many naturally occurring cell-surface markers present on mammalian cells are termed "CD" or "cluster of differentiation" molecules. Cell-surface markers often provide antigenic determinants to which antibodies, can bind to.

Accordingly, as defined herein, a "binding molecule specific for a cell-surface marker" refers to any molecule that can selectively react with or bind to that cell-surface marker; but has little or no detectable reactivity to another cell-surface marker or antigen. Without wishing to be bound by theory, affinity molecules specific for cell-surface markers generally recognize unique structural features of the markers. In some embodiments of the aspects described herein, the affinity molecules specific for cell surface markers are polyclonal and/or monoclonal antibodies and antigen-binding derivatives or fragments thereof.

In some embodiments, the cell binding molecule is a ligand that binds to a receptor on the surface of a cell. Such a ligand can be a naturally occurring molecule, a fragment thereof or a synthetic molecule or fragment thereof. In some embodiments, the ligand is a non-natural molecule selected for binding with a target cell. High throughput methods for selecting non-natural cell binding ligands are known in the art and easily available to a person skilled in the art (for example, Anderson et al. (2005); Anderson et al. (2004); Orner et al. (2004); Falsey et al. (2001); Liu et al. (2001); and Taurniare et al. (2006)).

The hydrogel of the present invention may also include cells to assist in repair and/or re-generation of the target tissue. As discussed above, the hydrogels of the present invention are particularly advantageous in that they preserve cells in a viable state. The cell populations can be developmentally mature or restricted, developmentally potent or plastic, or a combination of the foregoing cell types.

The hydrogels of the present invention can be used in devices (such as implants or grafts), which deliver cells to the site where tissue repair/restoration is required. In one embodiment, an implant or graft comprises a hydrogel that can be molded into any suitable form or shape, as discussed above. In one embodiment, a hydrogel, or device containing the hydrogel or a composition for forming a hydrogel, is formed in a subject, in a wound, or in an area of space where new tissue is needed. In some embodiments, one or more cell populations may be mixed with one or more tropoelastin monomers (including different types of tropoelastin monomers) and the device formed in situ.

Therefore, hydrogels, or devices comprising the hydrogels of the present invention, and further comprising one or more populations of cells growing thereon, can accelerate tissue growth and regeneration and participate as a reinforcing material in a newly-constructed, cell-based tissue. Tissues of this type usually lack elastin during adult tissue regeneration. The presence of elastin would more closely resemble the provisional matrix that is created during the development of tissues in vivo.

Sheet-like hydrogels, or devices comprising the hydrogels, provide reparative, replacement, and/or regenerative therapy for dermal tissues, membranes for tooth root coverage procedures, membranous tissues, flat bones (e.g., skull, breast-bone) and the like. Tubular hydrogels, or tubular devices comprising the hydrogels, provide reparative, restorative, replacement, and/or regenerative therapy for arteries, veins, ureters, urethras, nerves, long bones (e.g., femur, fibula, tibia, humerus, radius, ulna, metacarpals, metatarsals, etc.) and the like. Other three-dimensional hydrogels, or devices comprising the hydrogels, provide reparative, restorative, replacement, and/or regenerative therapy for organ transplants (e.g., liver, lung, skin, heart, pancreas, etc.), bone remodelling or mending of all types of bones, dental implants, or for muscle, tendon, ligament, and cartilage grafts.

The physical properties of the tropoelastin can be modulated to create hydrogels of specific strengths, elasticity, and density. Therefore, in certain embodiments, hydrogels, or devices comprising hydrogels, and further comprising one or more populations of cells growing thereon, are stable in vivo and will remain in a patient's body for up to 1, 2, 3, 4, 5, 10, 15 or more years.

In general, cells to be used in accordance with the present invention are any types of cells. The cells should be viable when encapsulated within the hydrogels of the present invention. In some embodiments, cells that can be encapsulated within hydrogels in accordance with the present invention include, but are not limited to, mammalian cells (for example human cells, primate cells, mammalian cells, rodent cells, etc), avian cells, fish cells, insect cells, plant cells, fungal cells, bacterial cells, and hybrid cells. In some embodiments, exemplary cells that can be encapsulated within hydrogels include stem cells, totipotent cells, pluripotent cells, and/or embryonic stem cells. In some embodiments, exemplary cells that can be encapsulated within hydrogels in accordance with the present invention include, but are not limited to, primary cells and/or cell lines from any tissue. For example, cardiomyocytes, myocytes, hepatocytes, keratinocytes, melanocytes, neurons, astrocytes, embryonic stem cells, adult stem cells, hematopoietic stem cells, hematopoietic cells (for example monocytes, neutrophils, macrophages, etc), ameloblasts, fibroblasts, chondrocytes, osteoblasts, osteoclasts, neurons, sperm cells, egg cells, liver cells, epithelial cells from lung, epithelial cells from gut, epithelial cells from intestine, liver, epithelial cells from skin, etc, and/or hybrids thereof, may be encapsulated within hydrogels in accordance with the present invention.

Exemplary mammalian cells that can be encapsulated within hydrogels in accordance with the present invention include, but are not limited to, human umbilical vein endothelial cells (HUVEC), Chinese hamster ovary (CHO) cells, HeLa cells, Madin-Darby canine kidney (MDCK) cells, baby hamster kidney (BHK cells), NS0 cells, MCF-7 cells, MDA-MB-438 cells, U87 cells, A172 cells, HL60 cells, A549 cells, SP10 cells, DOX cells, DG44 cells, HEK 293 cells, SHSY5Y, Jurkat cells, BCP-1 cells, COS cells, Vero cells, GH3 cells, 9L cells, 3T3 cells, MC3T3 cells, C3H-10T½ cells, NIH-3T3 cells, and C6/36 cells.

As also mentioned above, the hydrogel of the present invention is particularly advantageous in that it provides a tissue regeneration/repair system in which cells are evenly distributed throughout the hydrogel. Even distribution can help provide more uniform tissue-like hydrogels that provide a more uniform environment for encapsulated cells. In some embodiments, the hydrogel contains different cell types.

In some embodiments, the conditions under which cells are encapsulated within hydrogels are altered in order to maximize cell viability. In some embodiments, for example, cell viability increases with lower acrylate concentrations. In some embodiments, cells located at the periphery of a hydrogel tend to have decreased viability relative to cells that are fully-encapsulated within the hydrogel. In some embodiments, conditions (for example pH, ionic strength, nutrient availability, temperature, oxygen availability, osmolarity, etc) of the surrounding environment may need to be regulated and/or altered to maximize cell viability.

Cell viability can be measured by monitoring one of many indicators of cell viability. In some embodiments, indicators of cell viability include, but are not limited to, intracellular esterase activity, plasma membrane integrity, metabolic activity, gene expression, and protein expression. To give but one example, when cells are exposed to a fluorogenic esterase substrate (for example calcein AM), live cells fluoresce green as a result of intracellular esterase activity that hydrolyzes the esterase substrate to a green fluorescent product. To give another example, when cells are exposed to a fluorescent nucleic acid stain (for example ethidium homodimer-1), dead cells fluoresce red because their plasma membranes are compromised and, therefore, permeable to the high-affinity nucleic acid stain.

In general, the percent of cells in the hydrogel is a percent that allows for the formation of hydrogels in accordance with the present invention. In some embodiments, the percent of cells that is suitable for forming hydrogels in accordance with the present invention ranges between about 0.1% w/w and about 80% w/w, between about 1.0% w/w and about 50% w/w, between about 1.0% w/w and about 40% w/w, between about 1.0% w/w and about 30% w/w, between about 1.0% w/w and about 20% w/w, between about 1.0% w/w and about 10% w/w, between about 5.0% w/w and about 20% w/w, or between about 5.0% w/w and about 10% w/w. In some embodiments, the percent of cells in a composition that is suitable for forming hydrogels in accordance with the present invention is approximately 5% w/w. In some embodiments, the concentration of cells in a precursor solution that is suitable for forming hydrogels in accordance with the invention ranges between about $1 \times 10^5$ cells/mL and $1 \times 10^8$ cells/mL or between about $1 \times 10^6$ cells/mL and $1 \times 10^7$ cells/mL. In some embodiments, a single hydrogel comprises a population of identical cells and/or cell types. In some embodiments, a single hydrogel comprises a population of cells and/or cell types that are not identical. In some embodiments, a single hydrogel may comprise at least two different types of cells. In some embodiments, a single hydrogel may comprise 3, 4, 5, 10, or more types of cells.

Any of a variety of cell culture media, including complex media and/or serum-free culture media, that are capable of supporting growth of the one or more cell types or cell lines may be used to grow and/or maintain cells. Typically, a cell culture medium contains a buffer, salts, energy source, amino acids (for example, natural amino acids, non-natural amino acids, etc), vitamins, and/or trace elements. Cell culture media may optionally contain a variety of other ingredients, including but not limited to, carbon sources (for example, natural sugars, non-natural sugars, etc), cofactors, lipids, sugars, nucleosides, animal-derived components, hydrolysates, hormones, growth factors, surfactants, indicators, minerals, activators of specific enzymes, activators inhibitors of specific enzymes, enzymes, organics, and/or small molecule metabolites. Cell culture media suitable for use in accordance with the present invention are commercially available from a variety of sources, for example, ATCC (Manassas, Va.). In certain embodiments, one or more of the following media are used to grow cells: RPMI-1640 Medium, Dulbecco's Modified Eagle's Medium, Minimum Essential Medium Eagle, F-12K Medium, Iscove's Modified Dulbecco's Medium.

A person skilled in the art will recognize that the cells listed herein represent an exemplary, not comprehensive, list of cells that can be encapsulated within a precursor solution (and, therefore, eventually in a hydrogel) in accordance with the present invention.

Hydrogels described herein can additionally include one or more additives. Additives can be resolving (biodegradable) polymers, mannitol, starch sugar, inosite, sorbitol, glucose, lactose, saccharose, sodium chloride, calcium chloride, amino acids, magnesium chloride, citric acid, acetic acid, hydroxyl-butanedioic acid, phosphoric acid, glucuronic acid, gluconic acid, poly-sorbitol, sodium acetate, sodium citrate, sodium phosphate, zinc stearate, aluminium stearate, magnesium stearate, sodium carbonate, sodium bicarbonate, sodium hydroxide, polyvinylpyrolidones, polyethylene glycols, carboxymethyl celluloses, methyl celluloses, starch, micro-particles, nano-particles, aprotinin, Factor XIII, or their mixtures. Without wishing to be bound by a theory, one or more additives in the gel can alter (for example reduce or increase) the rate of gel degradation.

A hydrogel described herein can be combined with another material, for example a biomaterial, to form a composite material. The term "biomaterial" as used herein refers in general to biocompatible naturally occurring materials. Exemplary biomaterials include, but are not limited to, biopolymers, sponges, silk, decellularized tissues, and gelatin. The term "biopolymer" as used herein refers to either a naturally occurring polymer, or a synthetic polymer that is compatible with a biological system or that mimics naturally occurring polymers. Exemplary biopolymers include, but are not limited to, oligosaccharides, polysaccharides such as glycosaminoglycans, peptides, proteins, oligonucleotides, nucleic acids, polyketides, peptoids, hydrogels, poly(glycols) such as poly(ethylene glycol), collage, silk, and poly-lactates.

The hydrogel of the present invention may also include other components such as pharmaceutically-acceptable excipients and biologically active agents (for example drugs, vitamins and minerals), to assist in repair and/or re-generation of the target tissue, and/or to provide a method of achieving targeted delivery of biologically active compounds. In some embodiments, the hydrogels comprise cells that natively express, or that are genetically modified to express, a particular extracellular material, cytokine, and/or growth factor to promote or facilitate the repair, restoration, regeneration, or replacement of a tissue or organ.

Any biologically active agent known to a person skilled in the art to be of benefit in the diagnosis, treatment or prevention of a disease is contemplated as a therapeutic agent in the context of the present invention. Therapeutic agents include hormones, growth factors, enzymes, DNA, plasmid DNA, RNA, siRNA, viruses, proteins, lipids, pro-inflammatory molecules, antibodies, antibiotics, anti-inflammatory agents, anti-sense nucleotides and transforming nucleic acids or combinations thereof. Any of the therapeutic agents can be combined to the extent such combination is biologically compatible.

Suitable growth factors and cytokines include, but are not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeitins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, flt3-ligand, and tumor necrosis factor α (TNFα). Other examples are described in Dijke et al. (1989); Mulder et al. (1998); Ziegler et al. (1997). Suitable hormones include, but are not limited to, antimullerian hormone (or mullerian inhibiting factor or hormone), adiponectin, adrenocorticotropic hormone (or corticotropin), angiotensinogen and angiotensin, antidiuretic hormone (or vasopressin, arginine vasopressin), atrial-natriuretic peptide (or atriopeptin), calcitonin, cholecystokinin, corticotropin-releasing hormone, erythropoietin, follicle-stimulating hormone, gastrin, ghrelin, glucagon, gonadotropin-releasing hormone, growth hormone-releasing hormone, human chorionic gonadotropin, human placental lactogen, growth hormone, insulin-like growth factor 1, insulin-like growth factor (or somatomedin), leptin, luteinizing hormone, melanocyte stimulating hormone MSH, orexin, oxytocin, parathyroid hormone, prolactin, relaxin, secretin, somatostatin, thrombopoietin, thyroid-stimulating hormone (or thyrotropin), and thyrotropin-releasing hormone.

Exemplary pharmaceutically active compounds (for example, therapeutic agents) include, but are not limited to, those found in Harrison et al., Physicians Desk Reference, Pharmacological Basis of Therapeutics (1990), United States Pharmacopeia, current edition of Goodman and Oilman's *The Pharmacological Basis of Therapeutics*; and current edition of *The Merck Index*.

In another embodiment, the hydrogel comprises a population of multipotent or pluripotent stem cells, and hormones, growth factors, cytokines, morphogens (e.g., retinoic acid etc), extracellular matrix materials (e.g., fibronectin, laminin, collagen, etc.) or other materials (e.g., DNA, viruses, other cell types, etc.) that facilitate the differentiation of the cell population along a particular developmental pathway once the hydrogel has been implanted in the patient. Alternatively, or in addition, the cells may be differentiated in vitro during cell culturing with the hydrogel.

The bioactive agent can be covalently linked to the gel through a linker. The linker can be a cleavable linker or non-cleavable linker, depending on the application. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In many cases, the intended nature of the conjugation or coupling interaction, or the desired biological effect, will determine the choice of linker group.

Pharmaceutically-acceptable excipients include any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Gennaro (2006) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the hydrogel, its use is contemplated to be within the scope of this invention.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as colouring agents, coating agents, sweetening, flavouring, and perfuming agents can be present in the composition, according to the judgment of the formulator. General considerations in the formulation and/or manufacture of pharmaceutical agents may be found, for example, in Gennaro (2006).

The amount of cross-linked tropoelastin and biologically active agent present in the hydrogel will necessarily depend upon the particular drug and the condition to be treated. A person skilled in the art will be aware of appropriate agents and amounts to use to treat the condition.

A therapeutically effective amount of a hydrogel of the present invention may be delivered to a patient and/or organism prior to, simultaneously with, and/or after diagnosis with a disease, disorder, and/or condition. In some embodiments, a therapeutically-effective amount of a hydrogel of the present invention is delivered to a patient and/or organism prior to, simultaneously with, and/or after onset of symptoms of a disease, disorder, and/or condition.

The term "therapeutically-effective amount", as used herein, refers to an amount of the hydrogel of the present invention that is sufficient to treat, alleviate, ameliorate, relieve, delay onset of, inhibit progression of, reduce severity of, and/or reduce incidence of one or more symptoms or features of the disease, disorder, and/or condition.

Hydrogels described herein can be used for tissue engineering applications. In some embodiments, tissue engineering aims to replace, repair, and/or regenerate tissue and/or organ function or to create artificial tissues and organs for transplantation. In general, scaffolds used in tissue engineering (for example hydrogel scaffolds) mimic the natural ECM and provide support for cell adhesion, migration, and proliferation. Ideally, they allow for differentiated function, new tissue generation, and its three dimensional organization. Desired characteristics of hydrogel scaffolds include physical parameters such as mechanical strength and degradability, while biological properties include biocompatibility and the ability to provide a biologically relevant microenvironment. Biodegradable hydrogels are advantageous because after tissue is grown, the resulting structures are made entirely or almost entirely from biological components.

In some embodiments, hydrogels described herein can be used for many tissue-engineering applications, including growth of bone, cartilage, vascular tissues, cardiac tissues, endocrine glands, liver, renal tissue, lymph nodes, pancreas, and other tissues. In some embodiments, hydrogels can be used to deliver signals to cells, act as support structures for cell growth and function, and provide space filling.

In some embodiments, tissue engineering can be utilized to provide a potential method of generating a sufficient supply of cardiac tissues for transplantation. The hydrogels of the present invention have been found to be particularly useful for cardiac tissue engineering because they have the required mechanical and biological properties that facilitate cardiomyocyte attachment and growth, promote cellular alignment and elongation, and have the flexibility and capacity for repeated contraction. Existing tissue engineering approaches that involve culturing cells on porous three-dimensional scaffolds do not provide appropriate architecture and function of engineered tissues, making them unsuitable for engineering of complex organs such as the heart. For example, in contrast to native myocardium, which comprises elongated cells fused as oriented myofibrils that form contractile fibers, cells within three-dimensional scaffolds generate tissues with randomly oriented cell alignments. This lack of the proper orientation provides a technical obstacle in generating functional cardiac cells. In addition, the relative orientation of cardiac fibers cannot be organized relative to each other. Therefore, the present invention provides methods of producing cell-laden hydrogels in which proper microscale tissue properties (for example alignment of cells and the three dimensional orientation of cardiac fibers) are engineered.

In one embodiment, a hydrogel, or a device comprising the hydrogel, is provided to repair, restore, replace or regenerate cardiac tissue. The hydrogel, implant or graft can comprise one or more populations of cells. Exemplary cell populations used in a hydrogel or a device to repair, replace, restore or regenerate cardiac tissue comprise smooth muscle cells, cardiomyocytes, fibroblasts, mesenchymal stem cells, bone marrow stem cells, and the like.

In one embodiment, the device is a tissue-engineered construct. The tissue engineered construct may be a cardiac tissue construct (such as a film). In one embodiment, the film has a thickness of about 50 µm, and is micropatterned in the form of grooves having a groove depth of about 50 µm, distance between the grooves of about 50 µm, and wherein cardiomyocytes are seeded on surface of the grooves. In another embodiment, the tissue-engineered construct is a film having a thickness of about 50 µm, wherein the film is micropatterned in the form of grooves having a groove depth of about 20 µm, distance between the grooves of about 20 µm, and wherein cardiomyocytes are seeded on surface of the grooves.

In some embodiments, hydrogels to be used for tissue engineering applications can be formed in situ, enabling the polymer to conform to the shape of the implantation site. In situ hydrogel formation can be accomplished using methods to achieve cross-linking that can be performed remotely (for example photo-cross-linking, temperature-based cross-linking, etc.). In such embodiments, a precursor solution comprising cells and at least one polymeric component can be delivered to a target site by injection, for example. After delivery, light of an appropriate wavelength and duration can be applied to the precursor solution, resulting in cross-linking of the polymeric matrix and in situ formation of a cell-laden hydrogel that is tailored to the shape of the target site. This is particularly useful in wound-healing applications (as discussed above) and particular types of tissue that may benefit from in situ hydrogel formation include odontic tissue, periodontic tissue, pancreatic tissue, neural tissue, cardiac tissue, bone marrow, muscle tissue, bone tissue, skin tissue, liver tissue, hair follicles, vascular tissue, adipose tissue, lung tissue, retinal tissue, corneal tissue, and kidney tissue.

In some embodiments, the hydrogels can be used to construct complex delivery devices capable of precisely defined release profiles. This could be achieved through combining drugs or drug delivery devices (e.g. nanoparticles or microparticles) with the hydrogels described herein and using these to construct more complex drug delivery systems. To give but one example, hydrogels described herein can additionally comprise a therapeutic agent to be delivered (for example a small molecule, nucleic acid, protein, lipid, and/or carbohydrate drug). Such hydrogels can be useful for delivering a drug to a site that has been targeted for tissue regeneration. For example, a hydrogel comprising osteoinductive cells which is administered to a subject for purposes of regenerating new bone can additionally comprise one, or more bone morphogenetic proteins (BMPs) which, upon their release, can help further stimulate the growth of new bone.

In some embodiments, hydrogels to be utilized for drug delivery can be altered in ways that result in enhanced residence times, sustained drug delivery, and/or targeted drug delivery. Hydrogel properties, such as permeability (for example, sustained-release applications), enviro-responsive nature (for example, pulsatile-release applications), surface functionality (for example, PEG coatings for stealth release), biodegradability (for example, bioresorbable applications), and surface biorecognition sites (for example, targeted release and bioadhesion applications), can be altered and/or optimized for controlled drug-delivery applications. For example, by controlling polymer chain length, polymer composition, and/or polymer concentration, it is possible to control the density and degree of cross-linking within a hydrogel. Control over the density and degree of cross-linking provides, among other things, control over sustained-release properties of the resulting hydrogel.

In some embodiments, enzymes can be encapsulated within the hydrogels to create drug delivery systems that are responsive to biological analytes.

In some embodiments, hydrogels described herein can be utilized for in vitro tissue culture applications. In certain embodiments, hydrogels described can be utilized to develop assays that are useful for drug discovery and biological studies (for example assemble arrays of well-defined constructs for high-throughput drug screening). For example, the presence of feeder cells (for example endothelial cells or fibroblasts) in the presence of functional cells (for example hepatocytes) can be used to increase the maintenance of the functional cell type. Therefore, it is possible to generate three-dimensional structures that mimic the native structure of functional organs that can be subsequently used for drug discovery and/or diagnostics assays.

In some embodiments, the hydrogels described herein can be utilized for toxicity assays that can test the toxicity of a test substance (for example utilizing hydrogels in which liver cells have been encapsulated).

In some embodiments, the hydrogels described herein can be used to encapsulate cells within hydrogels in order to protect the cells from the immune system upon implantation into a subject. Therefore, the hydrogel can act as a barrier that prevents immune cells and/or antibodies from destroying the cells contained within the hydrogel.

In some embodiments, the hydrogels described herein can be used to make various structures, such as microfluidic channels. In this approach, the walls of the microchannels can be made from hydrogel assemblies instead of from more commonly-used materials such as glass and PDMS. Microfluidic channels made from hydrogel assemblies could be useful for many purposes, for example, in applications where it is desirable for the walls of the microfluidic channel to be porous.

In some embodiments, the hydrogels described herein can be used for diagnostic applications. To give but one example, cell laden hydrogels can be used for generating tissue-like hydrogels and/or hydrogel assemblies that can be used in assays that test for the presence of one or more particular microbes. For example, if a microbe (for example bacteria, viruses, fungi, etc) was known to specifically bind to a particular tissue, then tissue-like hydrogels could be fabricated that would test for the presence of the microbe in the sample.

The hydrogels described herein can be used in tissue engineering and repair. As used herein, the term "repair" refers to any correction, reinforcement, reconditioning, remedy, making up for, making sound, renewal, mending, patching, or the like that restores function. Accordingly, the term "repair" can also mean to correct, to reinforce, to recondition, to remedy, to make up for, to make sound, to renew, to mend, to patch or to otherwise restore function.

By "treatment," "prevention," or "amelioration" is meant delaying or preventing the onset, reversing, alleviating, ameliorating, inhibiting, slowing down or stopping the progression, aggravation, deterioration, or the progression of severity of a condition associated with a disease or disorder.

The hydrogels of the present invention may be administered using any amount and any route of administration effective for treatment. The exact amount required will vary from subject to subject, depending on the species, age, and general condition of the subject, the severity of the infection, the particular hydrogel, its mode of administration, its mode of activity, and the like.

In one embodiment, the hydrogels of the present invention, as well as devices comprising the compositions or hydrogels of the present invention, are used for treating wounds. Exemplary wounds that can be treated by the compositions or hydrogels described herein include blast injuries suffered during combat such as blunt trauma, shrapnel wounds and burns; burns, cuts (superficial and deep, such as those made during surgery), scrapes, abrasions, gashes and punctures.

After a wound has been cleaned and disinfected, it is closed to promote healing and reduce the risk of infection. The most frequently used closures are sutures and staples. These devices have the advantages of excellent tensile strength, a low dehiscence rate and rapid and simple application. However, the disadvantages are requiring removal and leaving scars on the tissue. Sutures and staples cannot be used to completely close wounds that have gaps in their proximate edges and do not seal the wound nor promote wound healing.

Recently, adhesives such as cyanoacrylate glues and fibrin biological adhesives have been introduced to close traumatic injuries and surgical incisions. N-butyl-1,2-cyanoacrylate (Histoacryl) and 2-octyl-cyanoacrylate (Dermabond) are widely used to close surface wounds and incisions. These adhesives cure rapidly upon contact with water, provide excellent tensile strength (30.6 N) and are sloughed off during the healing process. Tooth enamel bonded with cyanoacrylate has a shear bond strength of up to 7 MPa.

However, the contraindications for their use are inadequate hemostasis, areas of the skin under high tension, such as over the joints, or proximity to moist areas, which reduces tensile strength. Because cyanoacrylate adhesives are toxic and release formaldehyde during their breakdown by the body, they are not recommended for closing deep incisions or wounds. Infected or heavily contaminated wounds should not be closed with these adhesives.

Fibrin sealants include fibrinogen and thrombin as separate components. When these two proteins are mixed, the fibrinogen is cleaved and a fibrin clot forms, sealing and closing the wound. Additional components such as human factor XIII and aprotinin are often included in the preparations to increase the tensile strength of the clot and reduce fibrinolysis. However, fibrin sealants can be limited in their application as wound adhesives by their relatively low tensile strength (30 kPa). In addition, fibrin sealants do not have adequate tensile strength to close skin injuries. In some instances, adverse immunologic reactions are observed with repeated use of fibrin preparations that contain bovine blood products such as aprotinin.

Acrylated tropoelastin can be polymerized in vivo. Therefore, acrylated tropoelastin can be applied to the edges of a wound and polymerized in vivo on the surface or within the edges of a wound, physically closing and sealing the wound. During polymerization, tropoelastin-based scaffolds, as described elsewhere herein, are conducive to cell attachment and growth, and can promote the wound healing process. Therefore, in addition to performing as a strong wound adhesive and sealant, tropoelastin-based hydrogels may also contribute to accelerated wound healing by attracting regenerative cells into a supporting scaffold that self-assembles during fibrillogenesis. Tropelastin itself can participate as a reinforcing material in a newly forming scar. In one embodiment, a composition of the present invention comprising one or more cell populations or a hydrogel of the present invention comprising one or more cell populations (or a graft comprising the hydrogel of the present invention and one or more cell populations) is placed onto, or grafted into, a wound of a subject to repair, replace, or regenerate the wounded tissue.

Without wishing to be bound by any particular theory, the hydrogel provides a regenerative phase that continues for days, weeks, or months, and further provides an increased rate of epithelial cell growth that helps repair the wound with new tissue. Hydrogels used in particular embodiments of the present invention provide more rapid wound healing, more perfect reconstruction of the damaged parts of the wound, and minimize wound contraction.

In a particular embodiment, a wound of a subject is treated by providing a composition or a hydrogel of the present invention, or a graft comprising the hydrogel of the present invention. The hydrogel or graft can be molded into any form. In one embodiment, the hydrogel or graft is cast as a sheet, with a thickness that matches that of the wounded area. In another particular embodiment, the hydrogel or graft is cast directly in the wound.

In another embodiment, the composition contains, or the hydrogel is seeded with, one or more cell populations. In a related embodiment, the cell populations comprise fibroblasts, keratinocytes, and other cell types that can promote wound healing and tissues regeneration (e.g., stem cells). In certain embodiments, the composition, hydrogel or graft comprises growth factors, co-polymers, and a distribution of tropoelastin similar to the wounded tissue. Without wishing to be bound by any particular theory, it is contemplated that providing a hydrogel or graft comprising a tropoelastin polypeptide profile similar to the wounded tissue will result in a repaired wound whose tissue is indistinguishable from normal tissue, aesthetically and functionally.

In another embodiment, the composition and hydrogel described herein is used in regenerative medicine for osteopathic applications, including, but not limited to craniofacial, odontic, and periodontic applications. In one embodiment, compositions, hydrogels, and implants and grafts comprising the hydrogels, are provided for use in reconstruction and regeneration of oral and craniofacial tissues.

In particular embodiments, a composition or hydrogel comprises one or more tropoelastin monomers or multimers, and human collagen. The resulting hydrogels are engineered for the desired surface topography, porosity, strength and elasticity. As mentioned above, in some embodiments, the composition or hydrogel does not contain proteins or polypeptides other than tropoelastin.

In one embodiment, the hydro gel is cast in the form of a sheet and can be used as a regenerative membrane in various clinical applications, e.g., guided tissue regeneration (GTR) or root coverage procedures. In one embodiment, the hydrogel is cast as a sheet and seeded with periodontal ligament cells (PDL) forming an implant or graft that is suitable for use in a root coverage procedure. Once the implant has formed, a surgeon engrafts the implant in a root coverage procedure using methods known to a person skilled in the art.

In another embodiment, the hydrogel is cast in a three-dimensional shape for use as a bone filling material. Virtually any shape can be achieved because the pre-cross-linked composition is in a shapeable form. Once placed into a mold or into the desired area, the composition can be "hardened" by cross-linking. In addition, the hydrogel can support unique clinical applications in periodontal medicine for guided bone regeneration (GBR) procedures and eliminate the need for a bone filler and a membrane to contain the bone graft.

In a particular embodiment, the hydrogel, or an implant comprising the hydrogel, is molded into a desired shape, and comprises one or more populations of cells.

In a certain embodiment, the one or more cell populations comprise bone marrow stem cells, mesenchymal stem cells, or pre-osteoblast cells to facilitate tissue or bone regeneration. Additionally, the osteogenic potential of the hydrogel/implant can be used as a sole therapy or in combination with currently available commercial bone filler products or primary autologous bone harvests. A person skilled in the art will recognize that any type of bones can be repaired, replace, or regenerated using the foregoing techniques.

As noted above, in particular embodiments, hydrogels are cast into the form of tubes. The dimensions, elasticity, and strength of the tubular hydrogels can be engineered to be useful as arteries, veins, ducts, ureters, urethras, and virtually any other tubular structure in the body wherein reparative, replacement, or regenerative therapy is desired or required.

In one embodiment, a hydrogel, or an implant or graft comprising the hydrogel, is provided to repair, restore, replace or regenerate a vessel within the peripheral vascular system or cardiac vasculature. The hydrogel, implant or graft can comprise one or more populations of cells. Exemplary cell populations used in an implant or graft to repair, replace or regenerate a vessel within the vascular system comprise smooth muscle cells, fibroblasts, mesenchymal stem cells, bone marrow stem cells, and the like.

As discussed above, one significant advantage of the invention is the development of hydrogels with unique properties, e.g., tensile strength, elasticity, and flexibility/stiffness, generated by combining 2, 3, 4, 5, 6, 7, 8, 9, 10 or more individual tropoelastin isoforms, themselves having unique properties. Such unique hydrogels can be tailored for use at locations in the body where their unique properties are the most advantageous. For example, the strongest fibers can be used to repair muscles, the most elastic fibers can be used to construct bladders and other flexible organs (e.g. blood vessels and cardiac tissues), and the stiffest fibers can be used in cartilage repair.

In particular embodiments, the vessel being repaired, restored, replaced, or regenerated is selected from the group consisting of: veins, venules, capillaries, arterioles, and arteries. In other embodiments, the vessel being repaired, restored, replaced, or regenerated is selected from the group consisting of: coronary vessels, vessels in the brain, or any other vessel that has been damaged and/or injured and is in need of repair, restoration, replacement, or regeneration.

The present invention also relates to a method of repairing and/or restoring biological tissue, the method comprising administration of a therapeutically effective amount of a hydrogel of the present invention to a subject in need thereof.

The present invention also relates to the use of a therapeutically effective amount of a hydrogel of the present invention, for repairing and/or restoring biological tissue.

In one embodiment, the invention provides a hydrogel of the present invention, when used in a method of repairing and/or restoring biological tissue.

The present invention also relates to the use of a therapeutically effective amount of a hydrogel of the present invention, for the repair and/or restoration of biological, tissue. The invention also includes use of this hydrogel for the manufacture of a medicament for the repair and/or restoration of biological tissue.

It will be appreciated that, in these embodiments, the composition of the present invention can be used as an alternative to the hydrogel, provided that it is then treated appropriately (by, for example, exposure to water) to form a hydrogel. It will also be appreciated that the methods and uses can involve acrylated tropoelastin of the present invention, which can then be cross-linked and exposed to water to form the hydrogels of the present invention.

The present invention also relates to a method of repairing and/or restoring biological tissue comprising the steps of
  identifying a subject having tissue injury; and
  administering to the subject a therapeutically effective amount of the hydrogel of the present invention, administering to the subject an amount of the composition of the present invention to form a therapeutically effective amount of the hydrogel, followed by treating the composition to form the hydrogel, or administering to the subject an amount of acrylated tropoelastin of the present invention to form a therapeutically effective amount of the hydrogel, followed by treating the acrylated tropoelastin to cross-link the acrylated tropoelastin and form the hydrogel.

The present invention also relates to a method of accelerating repair and/or restoration of biological tissue comprising administering to a subject in need thereof:

a therapeutically effective amount of the hydrogel of the present invention, the composition of the present invention in an amount to form a therapeutically effective amount of the hydrogel, followed by treating the composition to form the hydrogel, or an amount of acrylated tropoelastin of the present invention to form a therapeutically effective amount of the hydrogel, followed by treating the acrylated tropoelastin to cross-link the acrylated tropoelastin and form the hydrogel.

In one embodiment, the biological tissue is cardiac tissue.

Compositions and hydrogels of the present invention are typically formulated in dosage unit form for ease of administration and uniformity of dosage. It will be understood, however, that the total daily usage of the hydrogels and/or hydrogel assemblies of the present invention will be decided by the attending physician within the scope of sound medical judgment.

The specific therapeutically effective dose level for any particular subject or organism will depend upon a variety of factors including the disorder being treated and the severity of the disorder; the activity of the specific active ingredient employed; the specific polymer and/or cells employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The hydrogels of the present invention may be administered by any route. In some embodiments, the hydrogels of the present invention are administered by a variety of routes, including direct administration to an affected site. For example, hydrogels may be administered locally near a site which is in need of tissue regeneration. Local administration may be achieved via injection of the cooled hydrogel directly to a site in need of tissue regrowth and/or repair.

In certain embodiments, the hydrogels of the present invention may be administered such that encapsulated cells and/or therapeutic agents to be delivered are released at concentrations ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered, for example, three times a day, two times a day, once a day, every other day, every third day, every week, every two weeks, every three weeks, or every four weeks. In certain embodiments, the desired dosage may be delivered using multiple administrations (for example, two, three, four, five, six, seven, eight, nine, ten, eleven, twelve, thirteen, fourteen, or more administrations).

In some embodiments, the present invention encompasses "therapeutic cocktails" comprising the hydrogels of the present invention. In some embodiments, hydrogels comprise a single cell type and, optionally, a therapeutic agent. In some embodiments, hydrogels comprise multiple different cell types and, optionally, a therapeutic agent.

It will be appreciated that cell-laden hydrogels in accordance with the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, a hydrogel comprising a certain cell type to be used to promote tissue growth may be administered concurrently with another therapeutic agent used to stimulate growth of the same tissue), or they may achieve different effects (for example, control of any adverse effects, such as inflammation, infection, etc).

The invention provides a variety of kits comprising one or more of the hydrogels and/or compositions of the present invention. For example, the invention provides a kit comprising a hydrogel and/or composition and instructions for use. A kit may comprise multiple different hydrogels and/or compositions. A kit may optionally comprise modified tropoelastins, cross-linked modified tropoelastins, biologically-active compounds, and the like. A kit may comprise any of a number of additional components or reagents in any combination. All of the various combinations are not set forth explicitly but each combination is included in the scope of the invention. A few exemplary kits that are provided in accordance with the present invention are described in the following paragraphs.

According to certain embodiments of the invention, a kit may include, for example, (i) a composition comprising modified tropoelastin; and (ii) instructions for cross-linking and forming a hydrogel from the composition.

A kit may also include, for example, (i) a composition comprising cross-linked modified tropoelastin; and (ii) instructions for forming a hydrogel from the composition.

Kits may further include other materials desirable from a commercial and user standpoint, including other buffers, diluents, filters, needles, and syringes.

Kits typically include instructions for use of the hydrogels of the present invention. Instructions may, for example, comprise protocols and/or describe conditions for production of hydrogels, administration of hydrogels to a subject in need thereof, production of hydrogel assemblies, etc. Kits will generally include one or more vessels or containers so that some or all of the individual components and reagents may be separately housed. Kits may also include a means for enclosing individual containers in relatively close confinement for commercial sale, for example, a plastic box, in which instructions, packaging materials such as styrofoam, etc, may be enclosed.

The kit or "article of manufacture" may comprise a container and a label or package insert on or associated with the container. Suitable containers include, for example, bottles, vials, syringes, blister packs, etc. The containers may be formed from a variety of materials such as glass or plastic. The container holds the hydrogel or composition which is effective for treating the condition and may have a sterile access port (for example the container may be an intravenous solution bag or a vial having a stopper pierceable by a hypodermic injection needle). The label or package insert indicates that the hydrogel or composition is used for treating the condition of choice. In one embodiment, the label or package insert includes instructions for use and indicates that the therapeutic composition can be used to repair or regenerate tissue.

The present invention will now be more fully described with reference to the accompanying examples and drawings. It should be understood, however, that the description following is illustrative only and should not be taken in any way as a restriction on the generality of the invention described above.

EXAMPLES

Synthesis of Modified Tropoelastin

Modified tropoelastin (TpeMA) was synthesized using recombinant human tropoelastin and methacrylic anhydride, as follows.

Tropoelastin isoform SHELD26A (Synthetic Human Elastin without domain 26A) corresponding to amino acid residues 27-724 of GenBank entry AAC98394 was purified from bacteria on a multi-gram scale as described in Wu et al. (1999).

Tropoelastin was methacrylated by the addition of methacrylate anhydride (MA, Sigma) to a 10% (w/v) tropoelastin solution in phosphate buffered saline (PBS; Invitrogen) and reacted for 12 h at 4° C. The solution was then diluted and dialyzed (Slide-A-Lyzer MINI Dialysis Device, 3.5K MWCO) against distilled water at 4° C. for 48 h and lyophilized to yield TpeMA. Various concentrations of MA (for example, 8, 15, 20% (v/v)) were used to modify the degree of methacrylation. $^1$H NMR analysis (FIG. 1a) was used to calculate the methacrylation degree of TpeMA. The effect of methacrylation on the coacervation behavior and secondary structure of tropoelastin was investigated using UV spectrophotometry and circular dichroism (CD) analysis, respectively. TpeMA polymers with methacrylation degrees of 31%, 44% and 48% were produced with 8% (v/v), 15% (v/v), and 20% (v/v) methacrylic anhydride, respectively. The synthesized TpeMA solutions were lyophilized and used in the remainder of the experiments.

The effect of methacrylation on the coacervation and secondary structure of tropoelastin was investigated. Coacervation of tropoelastin is an inverse temperature transition process, which plays a critical role in elastin fiber formation. The process of coacervation is mainly due to the intermolecular hydrophobic association of tropoelastin molecules. Methacrylation caused a reduction in the coacervation temperature of tropoelastin (FIG. 1b) due to the increased hydrophobicity of the protein molecules as a result of acrylate modification. Circular dichroism (CD) spectra of tropoelastin and methacrylated tropoelastin were characterized by an intense negative band at 200 nm, indicating a large proportion of disorder in the polypeptides, and a shoulder centered at 222 nm, demonstrating the presence of α-helical structure (FIG. 1c). Quantification of secondary structure indicated that methacrylation of tropoelastin had no effect on protein secondary structure (FIG. 1d).

Hydrogel Fabrication and Characterizations

TpeMA macromers with different methacrylation degrees were used to fabricate photo-cross-linked TpeMA hydrogels. To prepare the hydrogels, various concentrations of TpeMA (for example, 5, 10, 15% (w/v)) were prepared in PBS solution containing 0.5% (w/v) 2-hydroxy-1-(4-(hydroxyethoxy)phenyl)-2-methyl-1-propanone (Irgacure 2959, CIBA Chemicals) at 4° C. Ten μl of the solution was then pipetted between two glass coverslips separated by a 150 μm spacer and exposed to 6.9 mW/cm$^2$ UV light (360-480 nm) for 35 sec to form photo-cross-linked TpeMA gel. Characteristics of fabricated hydrogels including average pore size, swelling ratio, and mechanical properties were tailored by varying the methacrylation degree and concentration of the TpeMA solution. Methacrylated gelatin (GelMA) hydrogels were prepared by using 10% (w/v) GelMA with 80% methacrylation degree as described in Nichol et al. (2010) and used as control in this study.

Figure 2:
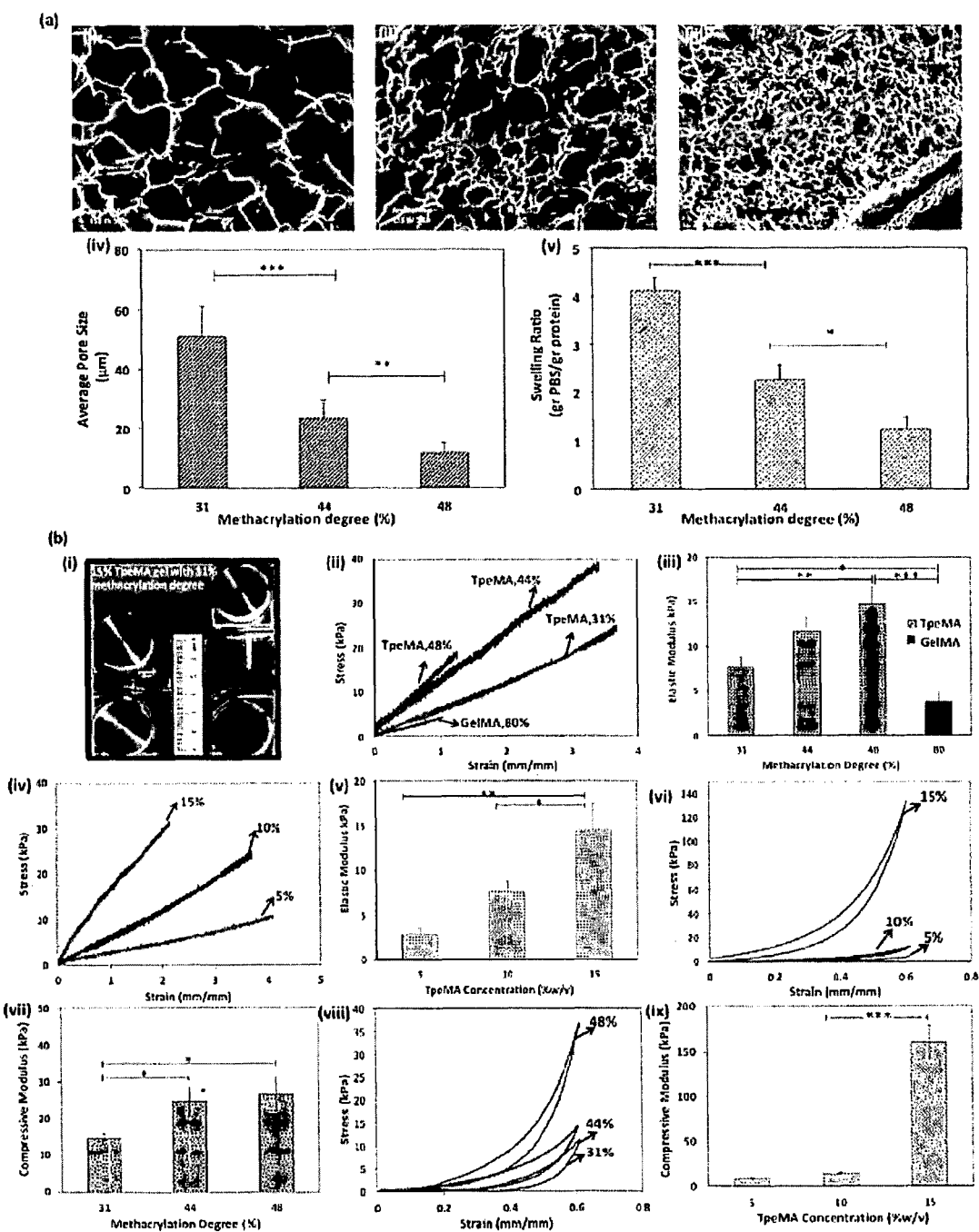
FIGS. 2a and 2b show the physical properties of TpeMA gels.
Figure 7:
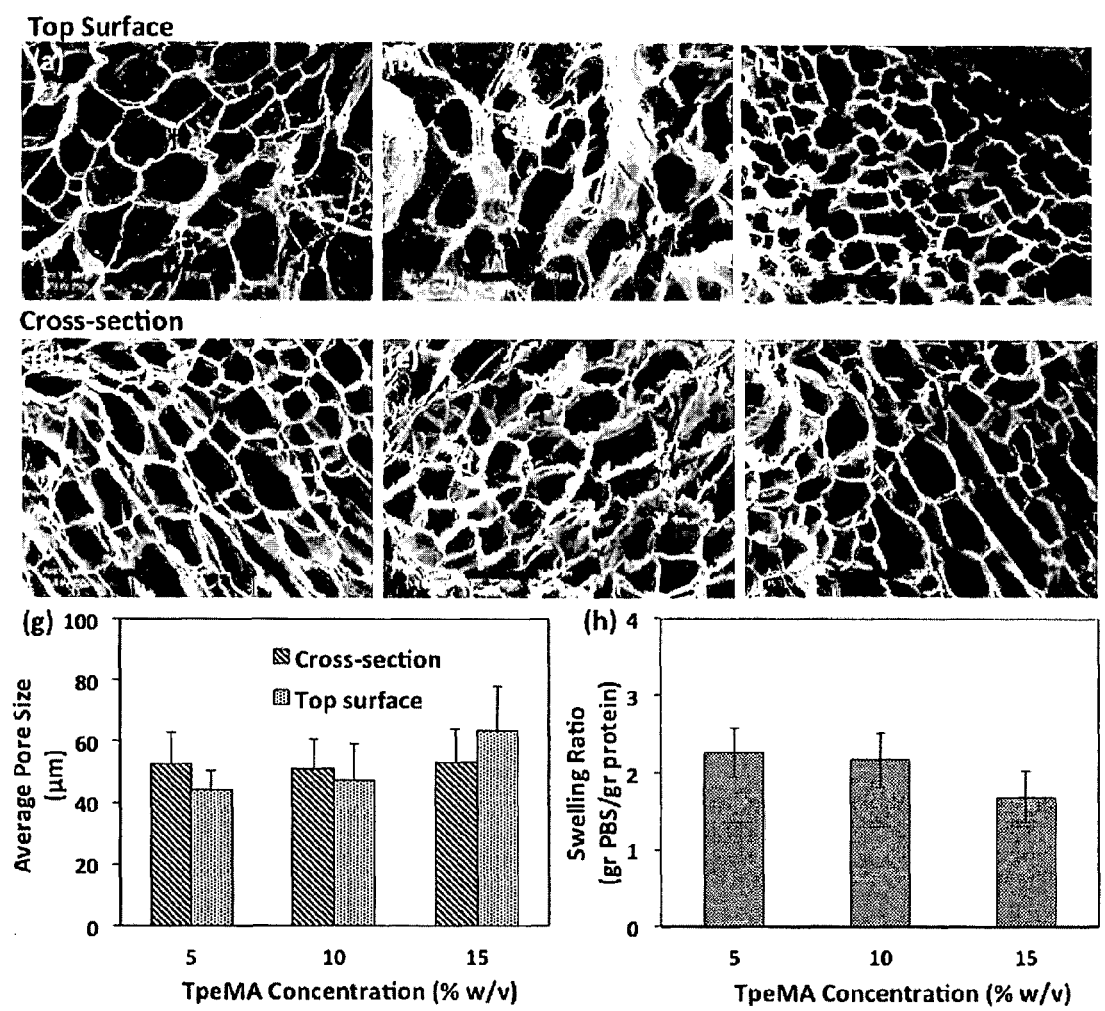
FIGS. 7a-7h show the effect of TpeMA concentration on pore characteristics and swelling behaviors of TpeMA gels. SEM images of TpeMA hydrogels produced by using (FIGS. 7a and 7d) 5.

The average pore size of 10% (w/v) TpeMA gels significantly decreased from 51±9 μm to 23.4±5.8 μm and 11.7±3.3 μm as the methacrylation degree was increased from 31% to 44% and 48%, respectively (FIGS. 2aii-iv) (P<**). Swelling ratios of TpeMA hydrogels decreased from 4.1±0.3 to 2.3±0.3 and 1.2±0.2 g liquid/g protein as the methacrylation degree was increased from 31% to 44% and 48%, respectively (FIG. 2v). Protein concentration had no significant effect on the swelling ratios and pore architectures of the hydrogels (FIG. 7). All TpeMA gels produced using various concentrations of TpeMA (5, 10, 15% (w/v)) with 31% methacrylation degree contained large pores (44-63.5 μm) both on the surfaces and within the cross-sections of the gels, with potential to facilitate nutrient and oxygen diffusion as well as removal of metabolic waste in three dimensional constructs.

The mechanical characteristics of TpeMA gel were analysed by tensile and unconfined cyclic compression tests. The fabricated hydrogels were highly elastic with extensibility up to 400%, elastic modulus between 2.8±0.6 kPa and 14.8±1.9 kPa and ultimate strength ranging from 12.5±2.2 kPa to 39.3±2.5 kPa depending on the methacrylation degree and concentration of TpeMA (FIGS. 2bi-iv, Table 1). TpeMA gels exhibited higher elastic modulus and extensibility compared to other photo-cross-linkable hydrogels such as 10% (w/v) methacrylated gelatin (GelMA) gel with 80% methacrylation degree (elastic modulus: 3.3±0.7 kPa, extensibility: 101%). The unique elastic properties of this photo-cross-linkable TpeMA gel make it a suitable protein-based matrix for the engineering of elastic tissues such as blood vessel, skin, lung, and cardiac where the presence of elastin in their structures plays an important role in their mechanical functionality.

The compressive properties of fabricated hydrogels were also evaluated by applying cyclic compression on the gels (FIGS. 2vi-ix). Gels were able to deform reversibly following 8 cycles of loading and unloading at 60% strain level. The hydrogels displayed energy losses of ~24.1-30.5% depending on TpeMA concentrations, which is comparable to the energy loss of purified native elastin reported to be 23±10% (Bellingham et al. (2003)). The compressive modulus of the hydrogels increased from 8.8±0.4 to 14.8±1.1 and 159.7±18.8 kPa when the TpeMA concentrations was increased from 5 to 10 and 15% (w/v), respectively. TpeMA gels exhibited higher compressive modulus compared to the values reported for various photo-cross-linkable hydrogels and elastin-based gels produced using different cross-linking approaches (Table 2).

TABLE 1

| Methacrylation degree (%) | TpeMA Concentration (% w/v) | Compressive Modulus (KPa) | Energy Loss (%) | Elastic Modulus (KPa) | Stress at Break (KPa) | Strain at Break (%) |
|---|---|---|---|---|---|---|
| 31 | 5  | 8.8 ± 0.4   | 24.1 ± 7   | 2.8 ± 0.6  | 12.5 ± 2.2 | 401.9 ± 10.1 |
| 31 | 10 | 14.8 ± 1.1  | 23 ± 3.2   | 7.6 ± 1.19 | 29.4 ± 5.7 | 375.6 ± 38 |
| 31 | 15 | 159.7 ± 18.8| 30.5 ± 6.4 | 14.5 ± 2.8 | 27.2 ± 3.4 | 272.7 ± 49.7 |
| 44 | 10 | 24.6 ± 4    | 26.9 ± 2.3 | 11.8 ± 1.5 | 39.3 ± 2.5 | 331.7 ± 47.6 |
| 48 | 10 | 26.6 ± 4.3  | 40.5 ± 3.9 | 14.8 ± 1.9 | 23.8 ± 7.5 | 134.9 ± 11.1 |

TABLE 2

| Polymer Networks | Crosslinking Method | Compressive Modulus (KPa) | Ref[a] |
|---|---|---|---|
| TpeMA | Photocrosslinking | 8.8-159.7 | Present study |
| Tpe/α-elastin | GA crosslinking under $CO_2$ | 4.9-11.8 | [13] |
| Tpe |  | 5.8 |  |
| α-elastin | GA crosslinking under $CO_2$ | 1.9 | [24] |
|  | HMDI crosslinking under $CO_2$ | 7 | [5] |
| GelMA | Photocrosslinking | 3-30 | [22] |
| PulMA | Photocrosslinking | 3.6-82.8 | [23] |
| GelMA/PEG | Photocrosslinking | 10-75 | [25] |
| GelMA/silk fibroin | Photocrosslinking | 4-73 | [26] |

Abbreviations:
Tpe: tropoelastin,
GA: glutaraldehyde,
HMDI; hexamethylene diisocyanate,
GelMA: gelatin methacrylate,
PulMA: pullulan methacrylate,
PEG: Poly(ethylene glycol)
[a]Some data estimated from graph.

[13] Annabi, N., Mithieux, S. M., Weiss, A. S. & Dehghani, F. Cross-linked open-pore elastic hydrogels based on tropoelastin, elastin and high pressure $CO_2$. *Biomaterials*. 2010; 31: 1655-65.
[24] Annabi, N., Mithieux, S. M., weiss, A. S. & Dehghani, F. Development and Characterisation of a Novel Elastin Hydrogel. *Mater Res Soc Symp Proc* 2009.
[5] Annabi, N., Mithieux, S. M., Boughton, E. A., Ruys, A. J., Weiss, A. S. & Dehghani F. Synthesis of highly porous crosslinked elastin hydrogels and their interaction with fibroblasts in vitro. *Biomaterials*. 2009; 30: 4550-7.
[22] Nichol, J. W., Koshy, S. T., Bae, H., Hwang, C. M., Yamanlar, S. & Khademhosseini, A. Cell-laden microengineered gelatin methacrylate hydrogels. *Biomaterials*. 31: 5536-44.
[23] Bae, H., Ahari, A. F., Shin, H., Nichol, J. W., Hutson, C. B., Masaeli, M., et al. Cell-laden microengineered pullulan methacrylate hydrogels promote cell proliferation and 3D cluster formation. *Soft Matter*. 2011; 7: 1903-11.

Hydrogel Patterning

Figure 10:
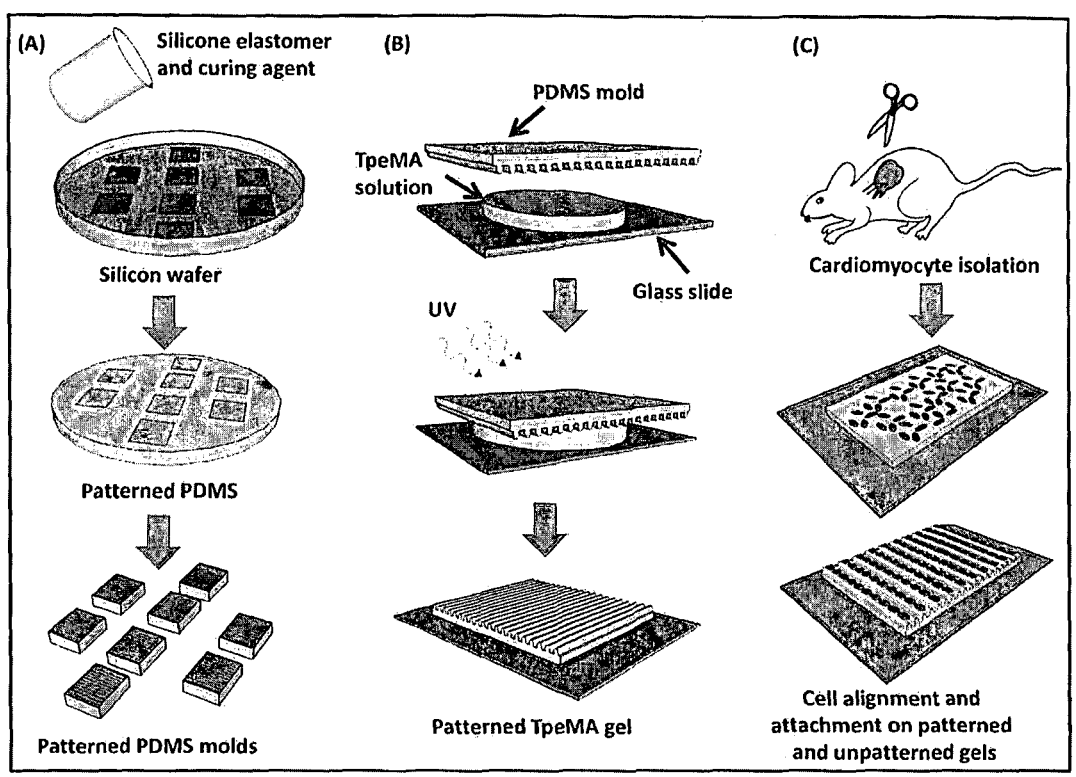
FIG. 10 is a schematic diagram for the fabrication of micropatterned gels using micromoulding process for cardiomyocyte alignment. (a) microchannels with varying geometries (for example channel size and spacing) were developed on a silicon wafer, and the master was covered with a layer of PDMS prepolymer. After curing for 1 h at 80° C., the PDMS mould was removed and cut into small moulds (1 cm×1 cm); (b) the mould was then placed on a glass slide containing 10 µl TpeMA and photoinitiator solution and was exposed to UV light for 35 sec to cross-link the hydrogel, the PDMS mould was removed from the gel after soaking in PBS for 5 min to generate micropatterned TpeMA gel; (c) the hydrogel containing microchannels was seeded with cardiomyocyte isolated from neonatal rat to align cells within the channels, an unpatterned TpeMA gel was used as control.

A micro-moulding technique was used to generate patterns on the surface of hydrogels. Micropatterned polydimethylsiloxane (PDMS)-based membranes 1 mm in thickness and with two different channel geometries (channel size× spacing: 20×20 μm, and 50×50 μm) were formed by using negative photoresist Epon SUB. The two different channel geometries were used to study the effect of channel size on cardiomyocyte alignment. The resultant PDMS moulds were then used to pattern the TpeMA and GelMA substrates (FIG. 10). The patterned hydrogels were created on TMSPMA coated glass slides to covalently bond the hydrogels to the glass slides and avoid hydrogel detachment from the slide during culture. To transfer the PDSM pattern to the surface of TpeMA gel, the surface of PDMS mould was first treated with plasma to create a hydrophilic surface and to facilitate the penetration of prepolymer solution among the channels. Upon cross-linking with UV light (the optimum UV exposure time was found to be 35 sec for TpeMA gel and 10 sec for GelMA hydrogels), the gels were soaked in PBS solution to facilitate PDMS mould detachment and preserve patterned architecture. The resulting hydrogels containing microchannels were soaked in culture media at 37° C. for 16 h prior to seeding with neonatal rat cardiomyocytes. Unpatterned gels were formed by using planar PDMS membranes instead of micropattenred PDMS moulds and used as controls.

Various concentrations of TpeMA including 5, 10 and 15% (w/v) with 31% methacrylation degree were tested to form micropatterned TpeMA-based substrates. No patterns were generated when 5% (w/v) prepolymer solution was used. However, micropatterned gels with high pattern fidelity were fabricated by using 10% (w/v) and 15% (w/v) protein solutions. Patterned GelMA gels were also fabricated by using 10% (w/v) prepolymer solution and used as controls.

Figure 4:
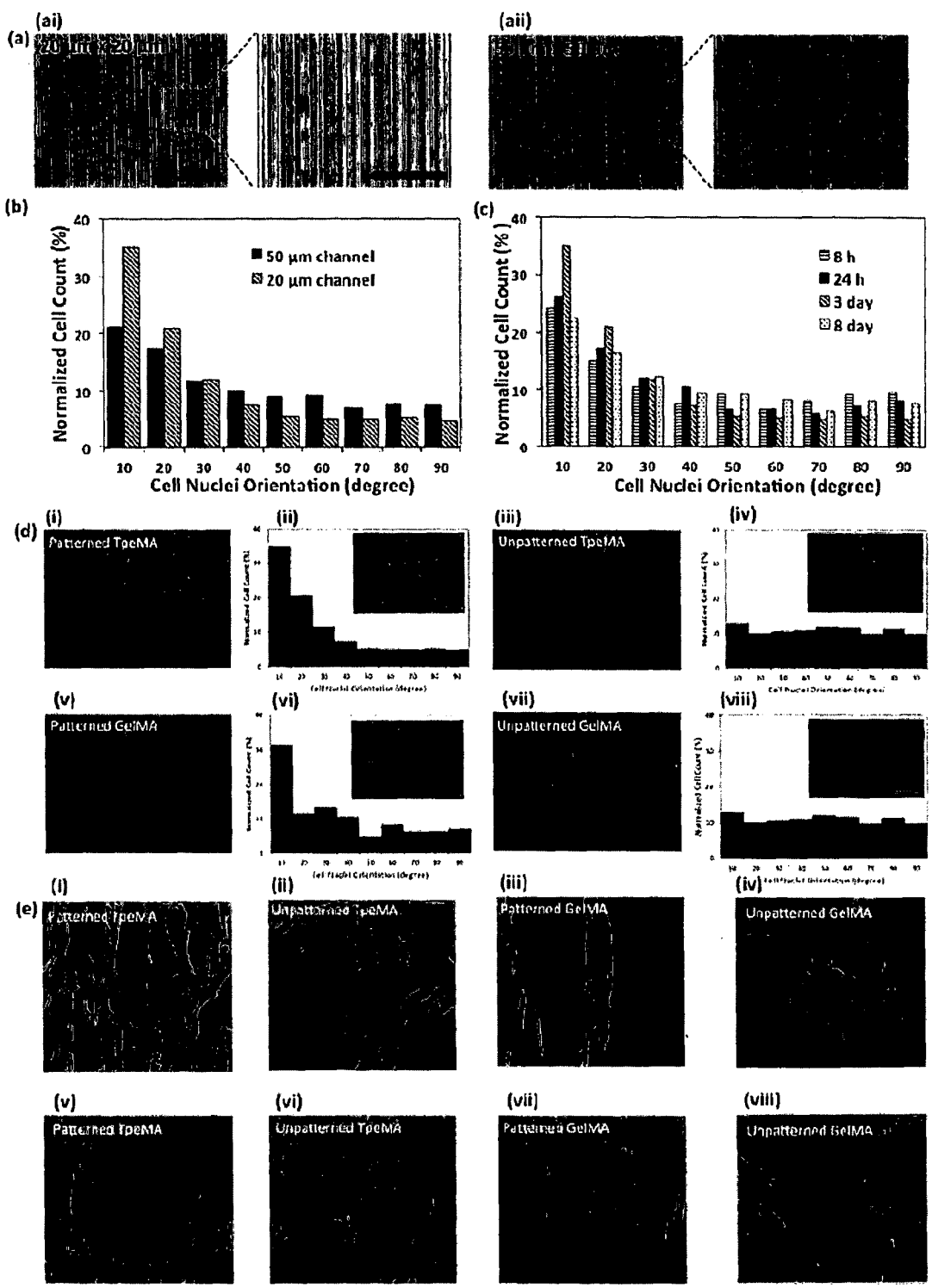
FIGS. 4a-4e show cardiomyocyte elongation and alignment on the surface of micropatterned gels.

FIGS. 4ai-ii show the patterns generated in this experiment on the surfaces of TpeMA gels, with resolution in the order of μm. It was found that the micropatterns created on the surface of TpeMA gels remained stable (without changing the microchannel width size and spacing) during cell culture (14 days). However, pattern deformation was observed in micropatterned GelMA gels after 7 days of culture due to the degradation of GelMA hydrogels over time.

With regard to cellular alignment and elongation, this was characterized on all substrates by phalliodin/DAPI staining. CMs seeded on patterned substrates oriented with an elongated morphology typical of differentiated CMs along the direction of patterns. However, for cells cultivated on unpatterned surfaces actin cytoskeletons were random with the overlapping of filaments in multiple directions. Differences were also observed in the shape and orientation of actin filaments as a function of channel size and culture time. Actin filaments were more aligned and elongated on the patterned surfaces with 20×20 μm channel width and spacing compared to those with larger channel dimensions (50×50 nm). In addition, it was found that the culture duration could affect the organization of actin cytoskeleton. Actin filament alignment was observable at early time point of 8 h post-seeding and reached the highest level of orientation on day 3 of culture. At longer culture times (day 8), the actin filaments were overlapped on the surfaces of the gels and their orientations decreased.

Quantitative assessment of cellular alignment as a function of channel size and culture was performed using DAPI-stained images and NIH Image) software as described in (Aubin et al. (2010), Charest et al. (2007) and Brammer et al. (2009)). Increasing the channel width from 20 μm to 50 μm significantly decreased cellular alignment from 56±4.8% to 38±2.9%, respectively (p<0.001) (FIG. 4b). Cardiomyocytes aligned and elongated along the channel within 20×20 μm micropatterned TpeMA gels and formed tissue constructs mimicking the structure of native rat heart.

Cellular alignment quantitative assessment indicated that culture time also affected alignment of the cells on the surface of TpeMA gels. As shown in FIG. 4c, 39±5% cell nuclei alignment was observed only 8 h after seeding. The cellular alignment significantly increased to 43±6% and 57±3% on day 1 and 3 of culture (p<0.001). However, a 1.5-fold decrease was observed in cellular alignment after 8 days of culture (38±3%), indicating the highest cellular alignment on day 3 of culture.

Figure 11:
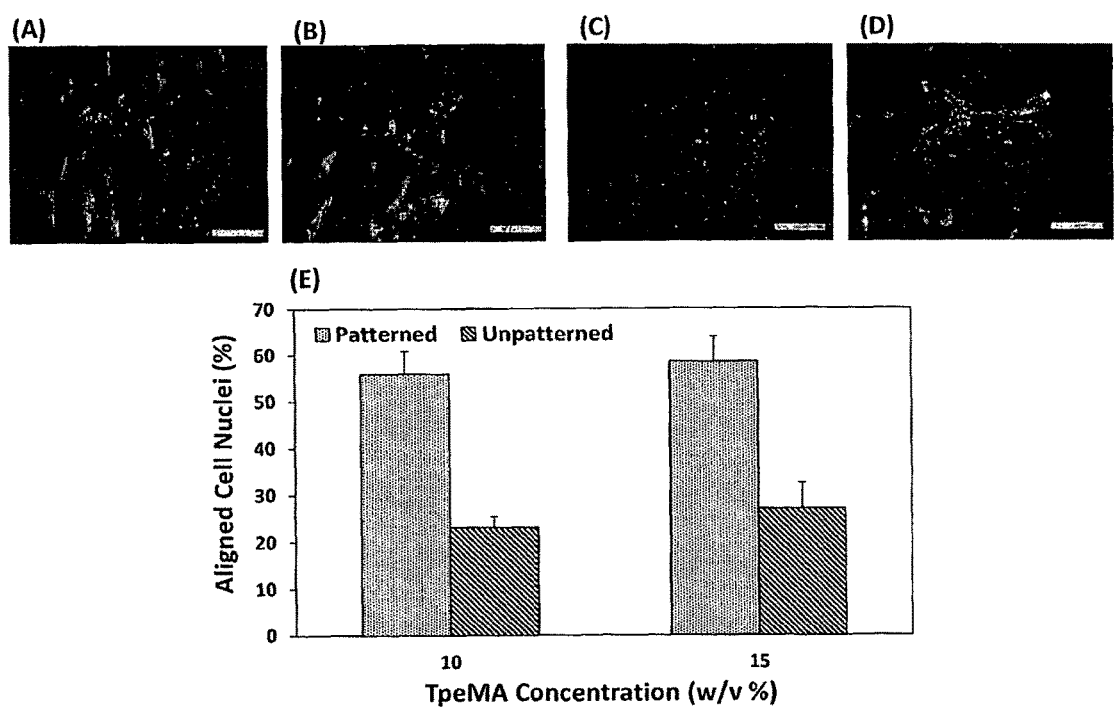
FIGS. 11a-11e show the effect of TpeMA concentration on cardiomyocyte elongation and alignment. Representative F-actin/DAPI stained images of cardiomyocyte seeded on TpeMA gels produced by using (FIGS. 11a and 11b) 10% (w/v) TpeMA.

The optimized channel width (20 μm) and culture time (day 3) for alignment analysis was used to compare the nuclei orientation on patterned and unpatterned TpelMA and GelMA gels (FIGS. 4*di-viii*). There was a significant difference in cell alignment between patterned and unpatterned gels (p<0.001). For example, in patterned TpeMA gel with 20-μm channel widths, 56 t 4.8% of the cells were aligned which is approximately 2.5-fold higher than the unpatterned sample (23±2.3%). Similar results were also obtained for patterned and unpatterned GelMA substrates. Micropatterned TpeMA gels exhibited significantly higher cellular orientation compared to GelMA gels (p<0.001). More attached and elongated cells on the surface of TpeMA were produced by using 15% (w/v) prepolymer solution compared to 10% (w/v) micropatterned hydrogels (FIG. 11). The surface of 15% (w/v) TpeMA gel was covered by a thick layer of CMs aligned in the direction of microchannels. In addition, increasing the TpeMA concentration had no significant effect on cellular alignment on patterned TpeMA gel. These data demonstrates that the hydrogel of the present invention is tolerant of variation of TpeMA concentration.

Cell Encapsulation (3D Culture)

NIH 3T3 fibroblast cells were used as a model cell for cell encapsulation. The cells were trypsinized and resuspended in TpeMA solution containing 0.5% (w/v) photoinitiator at a concentration of $5\times10^6$ cells/ml. Cell-laden TpeMA gels were fabricated as previously described following exposure to 6.9 mW/cm$^2$ UV light (360-480 nm) for 35 s on TMSPMA treated glass. The glass slides containing gels were washed three times with PBS and incubated for 5 days in 3T3 medium under standard culture conditions. Cell viability was determined by using a Live/Dead assay (Invitrogen, USA) according to the manufacturer's instructions.

Figure 3:
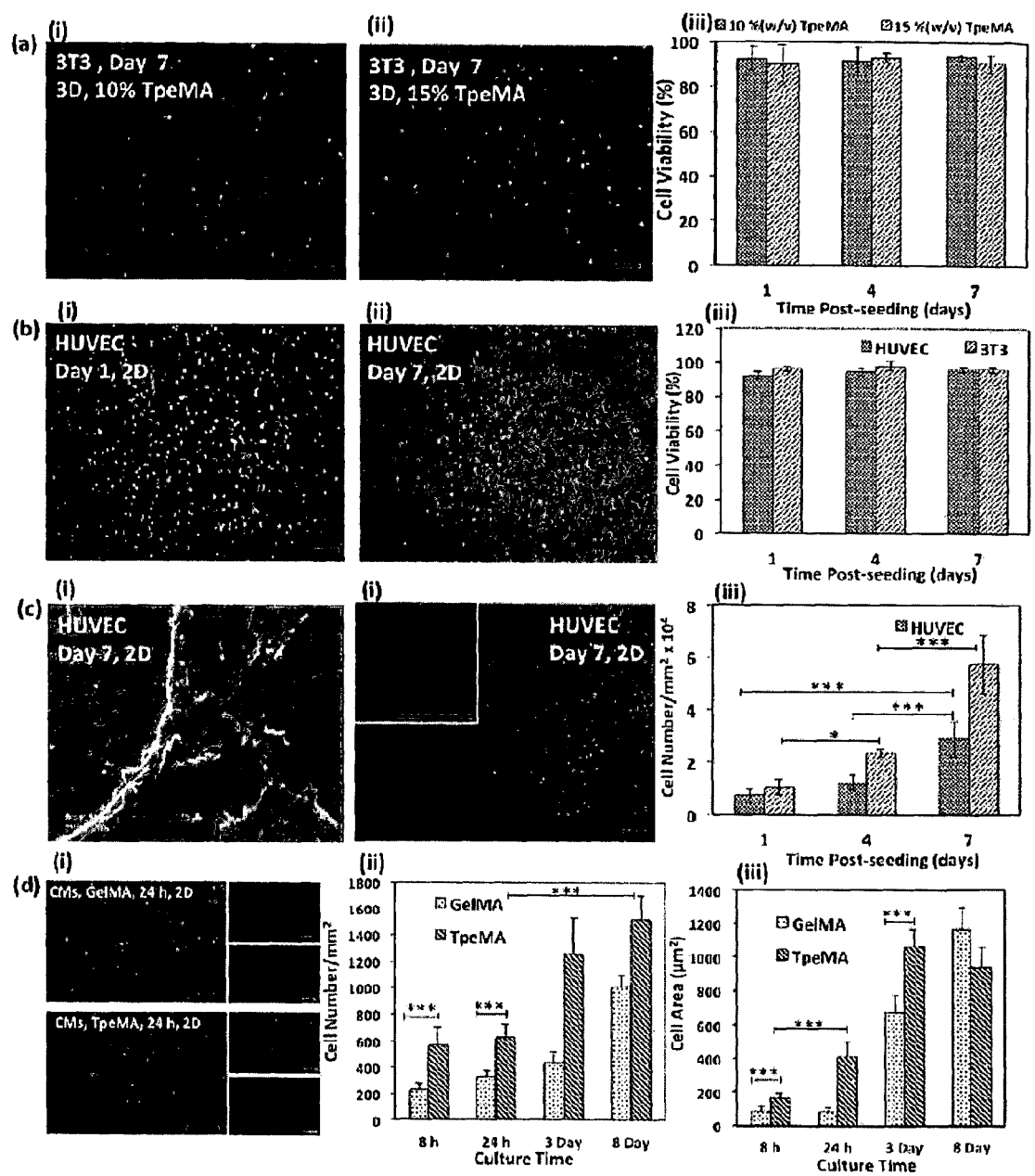
FIGS. 3a-3d show the two- and three-dimensional in vitro studies.

The viability of 3T3 fibroblasts encapsulated within the 3D structure of 5, 10 and 15% (w/v) TpeMA hydrogels was determined using Live/Dead assay. 3T3 cells encapsulated within all TpeMA gels remained viable throughout the 7-day culture period, demonstrating the suitability of TpeMA gels with varying physical properties for 3D cell encapsulation (FIG. 3*a*).

Surface Seeding (2D Culture)

Three different cell lines were used for surface seeding—HUVEC, NIH 3T3 fibroblasts, and neonatal rat ventricular cardiomyocytes. Cardiomyocytes were isolated from 2-day-old neonatal Sprague Dawley rats according to a protocol approved by the Institute's Committee on Animal Care. For cell adhesion and proliferation studies, TpeMA hydrogel films with 150 μm thickness were prepared in a similar manner to that used for the fabrication of cell-laden gels on TMSPMA glass slides. The slides containing TpeMA gels were seeded with cells ($2\times10^5$ cells/scaffold for HUVEC and 3T3 fibroblasts, $4\times10^5$ cells/scaffold for cardiomyocytes) and incubated for 8 days. Media was changed every 2 day.

The cell-seeded scaffolds were fixed at different culture times (for example 8 h, 24 h, 3 days, and 8 days) and stained with rhodamine-phalloidin (Alexa-Fluor 594; Invitrogen) and 4',6-diamidino-2-phenylindole (DAPI; Sigma) to visualize F-actin filaments and cell nuclei, respectively. Cell proliferation on the surfaces of gels was assessed by quantifying the cell densities, defined as the number of DAPI stained nuclei per given hydrogel area, over the culture time. Rhodamine-phalloidin staining was also used to characterize the cell spreading on the surfaces of hydrogels over the culture time. The cellular alignment on the patterned hydrogels was quantified by measuring the nuclei orientation angles using ImageJ software as described in Aubin et al. (2010). Alignment analysis was performed at different culture times for the gels with varying channel geometries. The expression of cardiomyocyte marker proteins on the gels was assessed by immunostaining for troponin-I, connexin 43, and sarcomeric α-actinin on day 8 of culture following previously established protocols.

Figure 8:
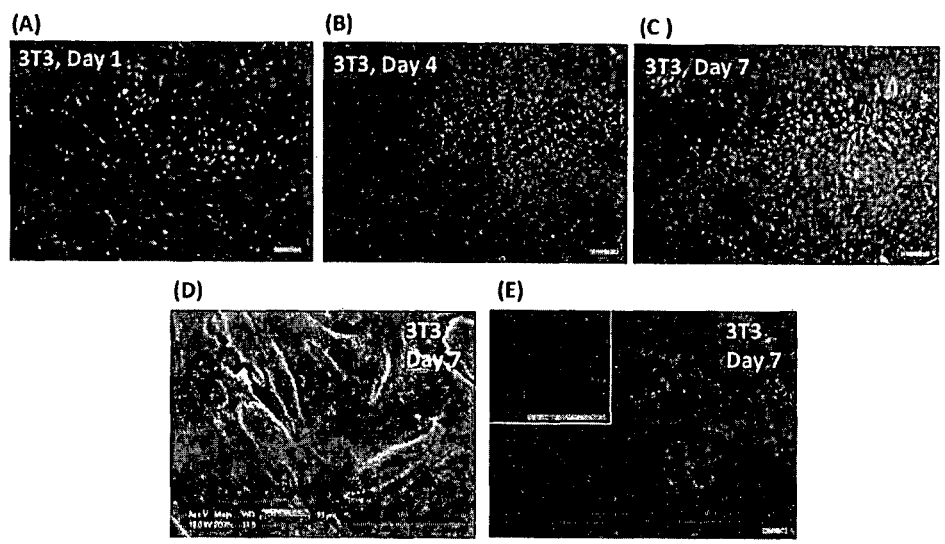
FIGS. 8a-8e show the viability, attachment, and spreading of 3T3 fibroblast cells on TpeMA surfaces. Live/Dead images from the hydrogels seeded by 3T3 after (FIG. 8a) 1 day, (FIG. 8b) 3 days, and (FIG. 8c) 7 days of culture.

In addition, the capacity for fabricated TpeMA hydrogels to support cell viability, adhesion, proliferation, and spreading was examined by culturing three different cell types, 3T3 fibroblasts, human umbilical vein endothelial cells (HUVEC) and neonatal rat cardiomyocytes (CMs), on the surfaces of TpeMA hydrogels. Cell viability experiments demonstrated excellent cell viabilities (>92%) for 10% TpeMA gels seeded with fibroblasts or HUVECs over a 7-day culture (FIGS. 3*bi-iii*, FIGS. 8*a-b*). The fibroblasts (FIG. 8*d*) and HUVECs (FIG. 3*ci*) adhered and formed monolayers on the surfaces of TpeMA hydrogel as shown by SEM images. The cells were well spread as indicated by staining of cell F-actin filaments and nuclei with rhodamine-phalloidin/DAPI on day 7 (FIG. 3*cii*, FIG. 8*e*).

Capacity to support cell proliferation on TpeMA gel surfaces was demonstrated through the presence of an increasing number of DAPI stained nuclei per given hydrogel area over the culture time (FIG. 3*ciii*). These results emphasize the excellent cell interactive properties of fabricated TpeMA gels and suggest the use of these highly elastic materials in cardiovascular tissue engineering applications where matrix elasticity plays an important role in maintaining cell viability and tissue function. For this purpose, the interaction of neonatal rat CMs with the TpeMA gels was evaluated and compared to methacrylated gelatin (GelMA) hydrogels. GelMA has previously been shown to be an attractive hydrogel for creating micropatterned tissue constructs (Aubin et al. (2010) and Nichol et al. (2010)). Cardiomyocyte attachment, proliferation and spreading on TpeMA and GelMA hydrogels were analyzed after 8 h, 24 h, 3 days and 8 days of culture using nuclei and F-actin staining (FIG. 3*d*). After 8 hours of culture a 2.5 fold higher number of cells had adhered to the surface of TpeMA gel (564±133 cells/mm$^2$) compared to GelMA (225±47 cells/mm$^2$) (FIG. 3*dii*). Although both hydrogels supported cell proliferation as demonstrated by an increasing number of nuclei over the 8 day culture, proliferation rates were higher on TpeMA gels compared to GelMA samples (p<***).

Figure 9:
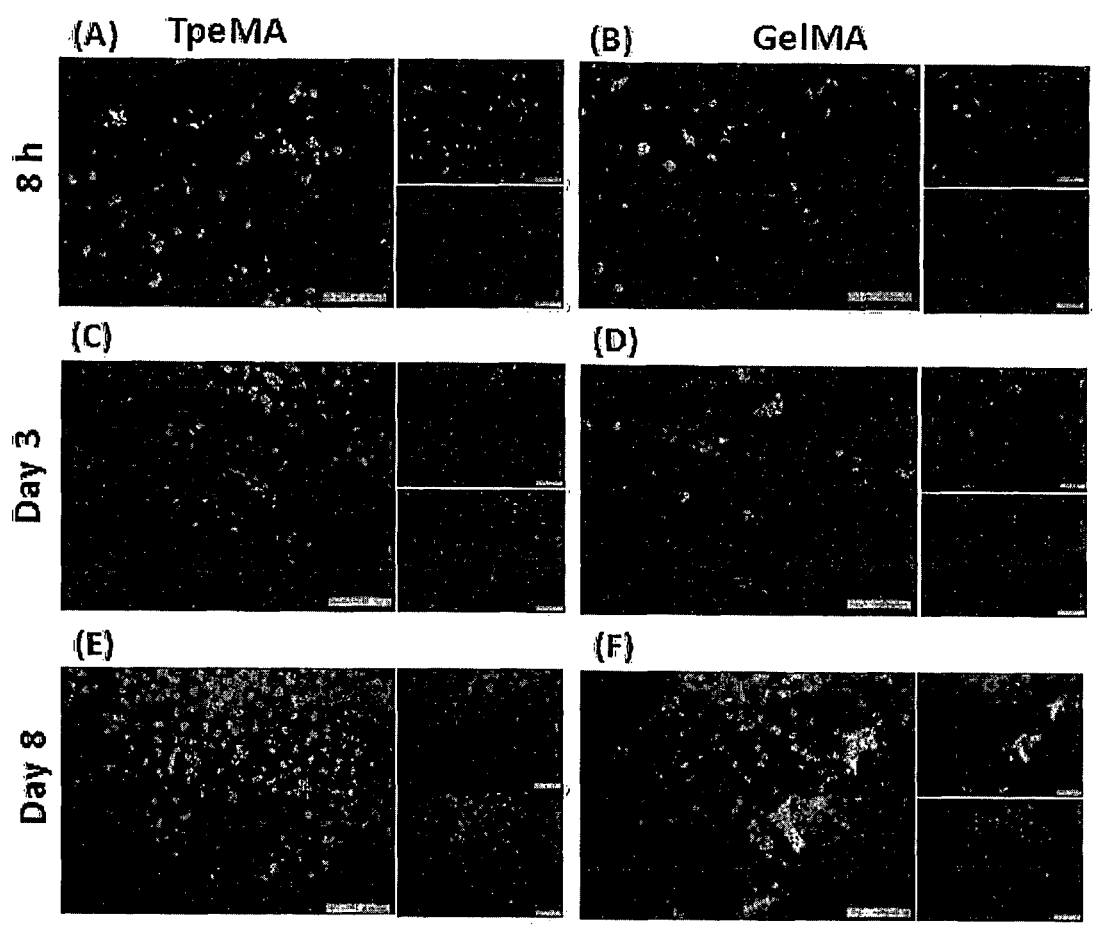
FIGS. 9a-9f show cell attachment and proliferation on TpeMA and GelMA hydrogels as a function of time. Rhodamine-labeled phalloidin/DAPI staining for F-actin/cell nuclei of TpeMA and GelMA gels seeded with cardiomyocyte after (FIGS. 9a and 9b) 8 h, (FIGS. 9c and 9d) 3 days, and (FIGS. 9e and 9f) 8 days culture, demonstrating higher cell attachment and spreading on TpeMA gel compared to GelMA at different culture times.

Cell spreading of cardiomyocytes on the surface of TpeMA gels had begun as early as 8 h after seeding and reached a maximum by Day 3 of culture. In contrast cells seeded onto GelMA hydrogels maintained rounded morphology with little spreading by day 3 of culture (FIG. 9). The calculated cell area of 416 μm$^2$, on TpeMA gel was five times higher than GelMA samples (82 μm$^2$) after 24 h of culture (FIG. 3*diii*). Similar results were obtained for day 3 of culture with the formation of a confluent layer of elongated CMs on TpeMA gels and clusters of cells in different regions of GelMA gels (FIG. 9*c-d*). The maximum cell spread area was 1065±99 μm$^2$ on TpeMA (day 3) and 1166±134 μm$^2$ on GelMA (Day 8). The elastic modulus of rat cardiomyocytes was reported to be 30 kPa (Feinberg et al. (2007)), which is closer to the elastic modulus of TpeMA gels (~15 kPa) compared to GelMA (~3.8 kPa).

Immunohistochemical Analysis

Immunohistochemistry was performed on day 8 of culture to evaluate the presence of cardiac differentiation markers on hydrogels through staining for sarcomeric α-actinin, troponin I, and connexin-43. Troponin I is an intracellular contractile protein which is responsible for muscle calcium binding and contraction and connexion-43 is involved in cell-cell electrical and metabolic coupling. The expression of troponin I on the surface of TpeMA hydrogels was significantly higher compared to GelMA gels; pervasive well-developed contractile apparatus were detected on the TpeMA substrates (FIGS. 4ei-ii) while the cardiomyocytes arranged in smaller aggregates on GelMA gels (FIGS. 4eiii-iv). Immunohistochemical staining of sarcomeric α-actinin indicated that cardiomyocytes seeded on TpeMA gels developed an elongated well-defined, cross-striated sarcomeric structure (FIGS. 4ev-vii), similar to those of native adult rat ventricular myocardium. Cross-striations characteristics for mature cardiomyocytes were also defected in GelMA gels but these gels had scattered and poorly organized sarcomeres compared to TpeMA samples (FIGS. 4evii-viii). Staining of connexion-43 also showed differences in the distribution pattern of gap junction protein between TpeMA and GelMA gels. In GelMA gels, connexion-43 was sparse and diffuse throughout the cell clusters; however, patches of connexion-43 staining were observed in different regions of TpeMA gel, demonstrating the presence of well-developed intercalated disk and gap junctions between myocytes. The higher level of cell junctions on cell-seeded TpeMA gels may improve cell-cell coupling and enhance overall contractile properties of engineered tissue constructs, which can lead to synchronous beating of the sample. The effect cardiomyocytes patterning on expression of cardiomyocytes proteins was also investigated. It was found that the patterning of cardiomyocytes elevated the levels of cardiac troponin I elongation and alignment on surfaces of both TpeMA and GelMA gels (FIGS. 4ei-iii). In addition, well-aligned registers of sarcomeres were developed on the patterned hydrogels (FIGS. 4ev-vii).

In native heart tissue, the cell's nuclei are surrounded by connective tissues and a large number of gap junctions are presented on the lateral surfaces of the cardiomyocytes for chemical linking and electrical coupling of the cells (Barr et al. (2005)). The well-developed networks of gap junctions and sarcomeres on TpeMA samples resemble the structures of native myocardium. Overall, these results indicate that cardiomyocytes in GelMA samples expressed lower level of cardiac markers compared to TpeMA gels. This is in agreement with previous studies indicating that ECM proteins are necessary to promote cardiomyocytes spreading and maturation due to their ability to provide appropriate ECM cues for cardiomyocytes (LaNasa & Bryant (2009) and Boateng et al. (2005)).

Assessment of Contractile Properties of Cardiomyocytes Seeded on Gel

The contractile properties of the cells, seeded on both TpeMA and GelMA hydrogels, were assessed by using movies taken with a video camera (Sony XCD-X710) attached to a microscope (Nikon, Eclipse TE 200U, Japan) at 10× magnification over 14 days of culture. The microscope was equipped with a temperature controller to maintain the samples at 37° C. during video recording. The video sequences were digitized at a rate of 15 frames per second. To quantify the beating frequency (number of beat/min), videos were taken from 3 selected spots of at least 3 individual samples were analyzed with a custom-written Matlab code for each gel type (TpeMA and GelMA). In addition, the effect of patterning on the spontaneous contractions of cardiomyocytes was determined by using unpatterned TpeMA and GelMA gels as controls.

Cardiomyocyte Contractile Response by Applying Electrical Stimulation

Figure 6:
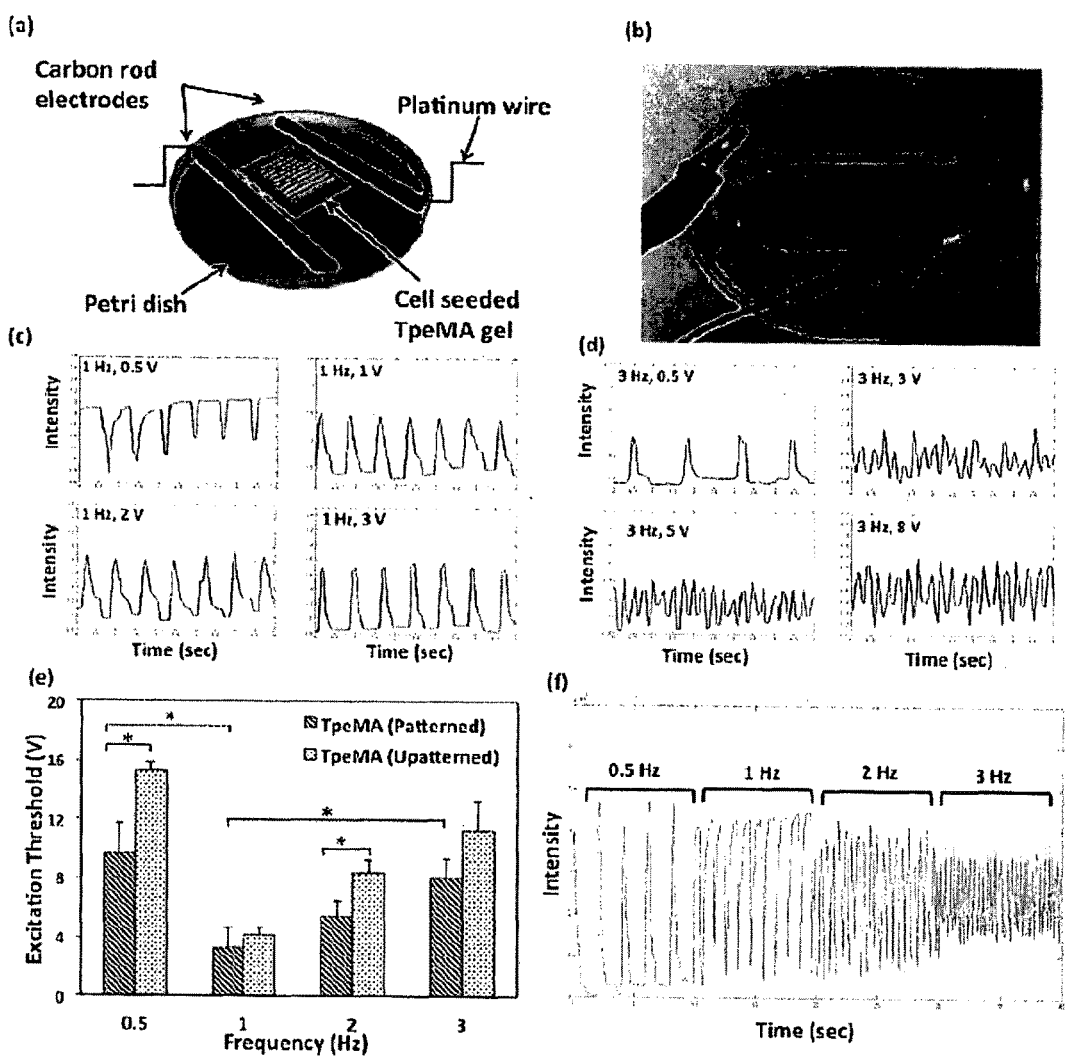
FIGS. 6a-6f show the electrical stimulation on cell-seeded TpeMA gels.

The response of cardiomycocytes to electrical stimulation was assessed by using a modified carbon electrode system to apply a pulsatile electrical signal to cardiomyocytes seeded on gels. The electrical stimulation chamber consists of a Petri dish and two carbon rod electrodes and was built according to the protocol described in Tandon et al. (2009). Briefly, two carbon rod electrodes spaced 2 cm apart were placed in a petri dish and fixed in place with silicon adhesive. Two platinum wires were attached on opposite sides of the electrodes by threading through holes drilled into the electrodes and the connections were covered by silicon adhesive (FIGS. 6a and b). Prior to use, the electrical stimulation chamber was washed with 70% ethanol. Electrical stimulation was applied to cardiomyocytes on both patterned and unpatterned hydrogels on day 8 of culture.

To deliver an electrical signal, the engineered construct containing cells was placed in between the two parallel carbon rod electrodes. The chamber was then filled with 30 ml culture media to cover the engineered construct and both electrodes. The electrical pulse generator applied biphasic square waveforms with 50 s pulses delivered at various frequencies including 0.5, 1, 2, 3 Hz. The excitation threshold, minimum voltage required to induce synchronous beating, at different frequencies (for example 0.5, 1, 2, 3 Hz) was also determined by varying the stimulating voltage from 3 to 15 V at each frequency.

Figure 5:
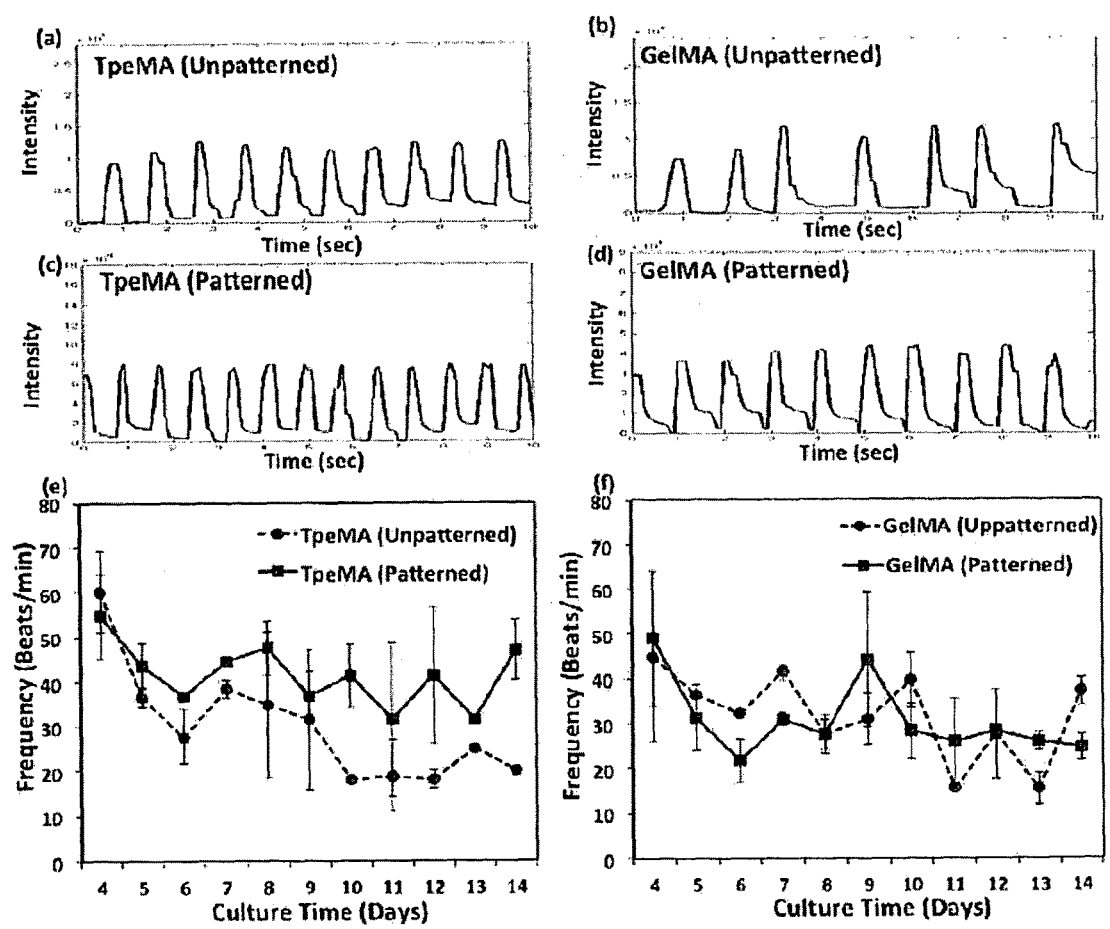
FIGS. 5a-5f show the beating characterization of cardiomyocyte seeded on hydrogels. Beating behaviour of cardiomyocyte-seeded (FIGS. 5a and 5c) TpeMA and (FIGS. 5b and 5d) GelMA gels on day 7 of culture, unpatterned samples are shown in a, b and patterned ones in c, d. Spontaneous beating frequency of cardiomyocyte seeded on TpeMA (FIG. 5e) and GelMA (FIG. 5f) gels over 14 days of culture.

The beating frequency of the heart can range from 0.05 to 20 Hz. In this study, cardiomyocytes seeded on both patterned and unpatterned TpeMA gels were capable of synchronous contractions. As few as 3 days after seeding, spontaneous beating was observed in both patterned and unpatterned TpeMA gels (FIGS. 5a and c). In contrast, cardiomyocytes seeded on unpatterned GelMA hydrogels were not beating in synchrony (FIG. 5b). Surface patterning of GelMA gels improved the spontaneous contraction (FIG. 5d). On micropatterned GelMA gels the contractions became stronger and more synchronized. The frequency of beating (number of beats/min), quantified between day 4 and 14 of culture, varied between 18-60 beats/min for TpeMA gels depending on the surface topography of the gel and culture duration (FIG. 5e). For the unpatterned TpeMA gel, the beating frequency significantly decreased from 60±9 beats/min on day 4 to 18 beats/min on day 10 of culture with no significant changes after that up to day 14 ($p<-0.001***$). However, for patterned gel, the beating frequency did not decrease significantly across the culture time and synchronized beating was observed for all the constructs during the culture. This demonstrated that surface patterning of TpeMA gels maintained the contractile activities of the cells up to 14 days in culture at which point the experiment was terminated. However, patterning of GelMA hydrogel had no significant influence on the beating rate of cardiomyocytes over the culture time (FIG. 5f). Generally, the beating frequency of cardiomyocytes was higher on TpeMA gel compared to GelMA (for example 48±6 beats/min compared to 27±4 beats/min on day 8 of culture), demonstrating the capability of fabricated elastic TpeMA gel to support expansion-contraction of cells during beating. On this basis, we predict that due to its high elasticity and resilience, the TpeMA substrate would contract during systole (contraction) and return to its original shape during diastole (relaxation) through synchronous contraction of cardiomyocytes.

The developed TpeMA materials in this study improved contractile properties of cardiomyocytes making it advantageous over GelMA and other biomaterials (for example, hyaluronic acid, Matrigel) for cardiac tissue engineering applications.

The effect of cellular alignment on the excitation threshold of cardiomyocytess was also investigated (FIG. 6e). The excitation threshold was found to be lower in micropatterned constructs compared to unpatterned gels. For example, at applied frequency of 2 Hz, the excitation threshold was approximately 1.6-fold higher in unpatterned TpeMA gel compared to patterned ones (P<−0.05*). The synchronous beating signal of the engineered TpeMA-based tissue constructs in response to applied external electrical field at frequency ranging from 0.05 Hz to 3 Hz (FIG. 6f) was also recorded. It was found that increasing the frequency reduced the beating intensity.

Statistical Analysis

Data were compared using one-way ANOVA followed by Bonferroni's post-hoc test (GraphPad Prism 5.02, GraphPad Software) software. Error bars represent the mean±standard deviation (SD) of measurements.

$^1$H NMR Spectra.

$^1$H NMR spectra of tropoelastin and TpeMA solutions in $D_2O$ (1% (w/v)) were obtained on a Varian Inova-500 NMR spectrometer and used to calculate methacrylation degree. NMR was performed at 4° C. to prevent coacervation of TpeMA solutions during analysis. The degree of methacrylation was calculated using the peak values between 4.9 and 6 ppm from methacrylate groups and the peak at 2.6 ppm from lysine residues in tropoelastin and defined as the number of methacrylated lysines divided by the total number of lysines.

UV Spectrophotometry.

The coacervation behaviors of 1% (w/v) tropoelastin and TpeMA solutions in PBS were assayed by monitoring turbidity through light scattering (300 nm) using a spectrophotometer (Shimaudzu UV-1601). The turbidity of each solution was assayed for 10 min at temperatures ranging from 4° C. to 45° C. The temperature was controlled by connecting the cuvette holder to a recirculating water bath. To investigate the effect of methacrylation degree on coacervation behavior, TpeMA macromers with varying methacrylation degrees were used. Following each measurement, the solutions were cooled to 4° C. for 10 min. At each temperature, the maximum variation in turbidity was recorded and expressed as a percentage of maximum turbidity for each TpeMA solution to create a series of coacervation curves.

Circular Dichroism.

Tropoelastin and TpeMA samples were dissolved in water at a concentration of 0.015% (w/v) and monitored using 0.1 cm quartz cuvettes in a Jasco J-815 CD spectrometer. Five spectral accumulations were obtained for each sample. Spectra were measured from 184 to 240 nm at 20° C. Data were expressed in terms of the mean residue ellipticity (deg $cm^2$ $dmol^{-1}$). Secondary structure analysis of the CD spectra was performed with the CONTIN, SELCON3 and CDSSTR programs through the CDPro software package using reference set SP43 as described, for example, in Sreerama & Woody (2000).

Swelling Ratio.

The swelling behaviour of TpeMA hydrogels were evaluated at 37° C. in PBS using previously reported procedures as described in Annabi et al. (2009) and Annabi et al. (2010). To prepare TpeMA hydrogels for swelling ratio measurements, 40 µL TpeMA solution was first injected into a custom-made PDMS mould (diameter: 5 mm and depth: 1 mm). A glass coverslip was placed on the mould before exposing to UV light for 180 sec. Samples were then collected from the mould and detached from the slide after soaking in PBS for 5 min. To calculate the swelling ratio, the gels were lyophilised and the dry weights were recorded. The samples were then incubated in PBS for 24 h after which the excess liquid was removed from the swollen gels and the samples were reweighed. The swelling ratio was then calculated as the ratio of mass increase to the mass of dry samples. The effect of methacrylation degree and TpeMA concentrations on the swelling ratio was investigated. At least 4 samples were tested for each condition.

Scanning Electron Microscopy (SEM).

SEM analysis was used to determine the pore characteristics of the fabricated TpeMA hydrogels and also to examine cell growth on the surfaces of hydrogels. SEM images of TpeMA gels were obtained by using a FEI/Philips XL30 FEG SEM (15 KV). Lyophilised samples were mounted on aluminium stubs and gold coated prior to SEM analysis. The effects of methacrylation degree and polymer concentrations on the pore characteristics of TpeMA hydrogels were examined. The average pore size of fabricated TpeMA gels were calculated using image J software. For pore size measurement, at least 100 pores were measured based on 3 images from each of 3 samples per condition.

Mechanical Characterizations.

Compressive and tensile properties of TpeMA gels were assessed using an Instron (model 5542) mechanical tester with a 10 N load cell. For the compression test, TpeMA gels were prepared as described previously for swelling ratio measurement. The hydrogels were swelled for 4 h in PBS prior to mechanical testing. A digital caliper was to use to measure the thickness (1±0.2 mm) and diameter (5±0.3 mm) of each hydrogel. Cyclic uniaxial compression tests in an unconfined state were then performed using a cross speed of 30 µm/s and a 60% strain level according to the procedure described in Annabi et al. (2010) and Annabi et al. (2009). Briefly, the hydrogels were cyclically preconditioned for seven cycles after which they were subjected to another loading and unloading and the compression (mm) and load (N) were recorded at the 8th cycle using Bluehill software. The tangent slope of the linear region of the stress-strain curve for the 8th cycle was reported as the compressive modulus. The energy loss for the 8th cycle was also calculated based on the area between the loading and unloading curves. The effects of methacrylation degree and TpeMA concentrations on the compressive properties of TpeMA gels were determined by using various concentrations of TpeMA solutions (5, 10, 15% (w/v)) with varying methacrylation degrees (31%, 44% and 48%). At least five samples were tested for each condition.

For tensile test, samples with 20±0.3 mm in length, 4±0.3 mm in width, and 1±0.1 mm in thickness were prepared following the procedure described previously for hydrogel fabrication. The gels were swelled for 4 h in PBS and then mounted onto the mechanical tester. The tensile grips were covered by fine sand paper to eliminate slippage. The test was performed at 1 mm/min strain rate until failure. The tensile properties of samples including elastic modulus (the tangent slope of the stress-strain curve), ultimate stress (stress at failure), and maximum strain or extensibility (strain level at failure) were reported. The effect of methacrylation degree and TpeMA concentration on tensile properties of hydrogels were investigated. At least five gels were tested per conditions.

Hydrogel Patterning.

Silicon wafers were spin coated with negative photoresist Epon SU8 and exposed to ultraviolet light through a mask with 20 µm and 50 µm thick parallel lines, and 20 µm and 50 µm thick spacings between lines (referred to as 20×20 and 50×50 µm) to generate micropatterns on the silicon master. The master wafers were then used to directly pattern polydimethylsiloxane (PDMS)-based membranes by pouring a mixture of silicon elastomer and curing agent (Sylgard 184 kit, Dow Corning) onto the wafer and curing at 80° C. for 1 h. The resulting PDMS mold containing microchannels, with specified channel size and spacing, was peeled off from the wafer and cut into smaller rectangular pieces (1 cm×1 cm) before surface modification through plasma treatment for 30 sec. The resulting PDMS molds were used to pattern the TpeMA and GelMA substrates (FIG. 10a).

TpeMA and GelMA prepolymer solutions with 10% (w/v) were used to create micropatterned hydrogels. To generate microchannels on the surface of hydrogels, 10 µl of the prepolymer solution containing 0.5% (v/v) photoinitiator was first injected onto a TMSPMA coated glass slide. A micropattenred PDMS mold was then placed on the top of the prepolymer solution and the whole assembly was exposed to UV light for 35 sec (for TpeMA) or 10 sec (for GelMA) to UV cross-link the hydrogels. The PDMS mold was peeled off from the sample after soaking in PBS for 5 min to generate micropatterned gels (FIG. 10b). The resultant hydrogels containing microchannels were soaked in culture media at 37° C. for 16 h prior to seeding with neonatal rat cardiomyocytes (CMs). Unpatterned gels were formed by using planar PDMS membrane instead of micropatterned PDMS mold and used as control.

Cell Culture and Isolation.

Immortalized green fluorescent protein (GFP)-expressing human umbilical vein endothelial cells (HUVEC; ATCC), NIH 3T3 fibroblasts, and neonatal rat ventricular cardiomyocytes were used in this study. HUVECs were cultured in a 5% $CO_2$ humidified incubator at 37° C. in endothelial basal medium (EBM-2; Lonza) supplemented with endothelial growth BulletKit (Lonza) and 100 units/ml penicillin-streptomycin (Gibco, USA). 3T3 fibroblast cells were maintained in Dulbecco's modified eagle medium (DMEM; Invitrogen) modified with 10% fetal bovine serum (FBS) and 100 units/ml penicillin-streptomycin. Cells were passaged approximately 2 times per week and media was changed every 2 days.

Cardiomyocytes were isolated from 2-day-old neonatal Sprague Dawley rats according to the protocol approved by the Institute's Committee on Animal Care. Briefly, Sprague-Dawley neonatal pups were transferred into a clean cage and narcosis was induced using compressed $CO_2$ gas. The pups were quickly decapitated with scissors after disinfecting the neck and sternum area with 70% ethanol. The thorax was then opened following a straight line along the sternum to excise the heart from the pup. The isolated hearts were placed in Hank's Balanced Salt Solution (HBSS) buffer before removing the atria and blood vessels. Each heart was quartered and incubated in a 0.06% (w/v) solution of trypsin in HBSS at 4° C. for 16 h on a shaker to digest the tissues. The trypsin digestion was then stopped by adding culture media followed by shaking for 5 min at 37° C. The tissues were subjected to a series of digestions in 0.1% (w/v) collagenase type II solution in HBSS (10 min shaking at 37° C. for each digestion). The supernatant for the first digestion was discarded, and the cell suspensions from the subsequent two to three digestions were collected and centrifuged at 1000 rpm for 5 min after which the cells were resuspended in DMEM supplemented with 10% FBS and 2 mM L-glutamine. The cell suspension was transferred to a T-175 flask and pre-plated for 1 h period to enrich for cardiomyocytes (i.e. attached cells were cardiac fibroblasts and unattached ones were cardiomyocytes) and then used for seeding. Each hydrogel was then seeded with $4 \times 10^5$ cells in a 24 well plate immediately after pre-plating and cultured in DMEM media containing 10% FBS, 1% L-Glutamine (Gibco, USA), and 100 units/ml penicillin-streptomycin for up to 14 days.

Cell Viability.

Cell viability was determined by using a Live/Dead assay Kit (Invitrogen, USA) according to the manufacturer's instructions. To perform cell viability assay, the cells were stained with 0.5 µl/ml calcein AM and 2 ethidium homodimer-1 (EthD-1) in PBS. Two hundred µl calcein AM/(EthD-1) solution was added to each well of a 24 well plate containing hydrogels. The well plate was then incubated at 37° C. for 20 min after which the live (green) and dead (red) cells were observed by using an inverted fluorescence microscope (Nikon TE 2000-U, Nikon instruments Inc., USA). The number of live and dead cells was counted by ImageJ software using at least 4 images from different areas of 3 gels for each condition. Cell viability was then calculated based on the number of live cells divided by the total cell number.

Cell Adhesion, Proliferation and Spreading.

Rhodamine-phalloidin (Alexa-Fluor 594; Invitrogen) and 4',6-diamidino-2-phenylindole (DAPI; Sigma) staining was used to quantify the cellular attachment, proliferation, and spreading on the surfaces of fabricated hydrogels. For DAPI staining, the cell-seeded scaffolds were first fixed in 4% paraformaldehyde (Sigma) solution in PBS for 30 min. The samples were then incubated in a 0.1% (v/v)) DAPI solution in PBS for 10 min at 37° C. to stain the cell nuclei. The stained samples were then washed twice with PBS before visualizing with an inverted fluorescence microscope. ImageJ software was used to count the DAPI stained nuclei and assess the proliferation of the cells on the surfaces of gels at various culture times. Rhodamine-phalloidin staining was used to characterize cell spreading on the surfaces of hydrogels. To stain F-actin filaments of the cell, the cell-seeded gels were fixed in 4% paraformaldehyde for 30 min. The cells were then permeabilized in a 0.1% (w/v) Triton X-100 solution in PBS for 20 min and blocked in 1% (w/v) bovine serum albumin (BSA) for 1 h. The samples were then incubated in a solution of 1:40 ratio of Alexa Fluor-594 phalloidin in 0.1% BSA for 45 min at room temperature to stain the actin cytoskeleton. Cell spreading was determined by measuring the cell area adhered to the surfaces of the gels using fluorescence images. To quantify cell spreading, the area of a cluster of the cells was measured by using ImageJ software and divided by the number of the cell nuclei within the cluster to obtain the average area of a single cell. Three images from three individual samples for each sample type (TpeMA and GelMA) were analysed.

Cell Alignment.

The images from DAPI stained nuclei were used to quantify the nuclear alignment as described previously in Aubin et al. (2010). Built-in functions of NIH ImageJ software were used to measure the nuclei orientation angles, which were defined as the orientation of the major elliptic axis of separate nuclei with respect to the horizontal axis. The nucleus alignment angles were then normalized with respect to the mean alignment of all nuclei within each sample. The normalized alignment angles were grouped in 10 degree increments and all cell nuclei within less than 20 degrees were considered as aligned cells. For both hydrogel types (TpeMA, GelMA), the nuclei alignment in patterned and unpatterned samples was compared. The effects of channel width and spacing as well as culture time on cellular alignment were investigated by using micropatterned gels with varying channel geometries (channel size×spacing: 20µ×20µ, and 50µ×50µ and performing alignment analysis at different post-seeding time (8 h, 24 h, 3 days, and 8 days).

For alignment quantification, at least three images from three samples were used for each condition.

Immunostaining for Cardiac Markers.

The expression of cardiomyocyte proteins on the gels was assessed by immunostaining for troponin-I, connexin-43, and sarcomeric α-actinin on day 8 of culture following previously established protocols as described in Tandon et al. (2009). To immunostain the samples, the cells were fixed in 4% paraformaldehyde for 30 min at room temperature, washed with PBS, permeabilized in a 0.1% (w/v) Triton X-100 solution in PBS for 20 min, and blocked in 10% (v/v) goat serum in PBS for 1 h. The cell-seeded gels were then incubated with primary antibodies (rabbit-anti-connexin 43, mouse-anti-troponin, and mouse-anti-sarcomeric α-actinin) diluted 1:200 ratio in 10% (v/v) goat serum for 16 h at 4° C., with subsequent rinsing, with PBS. The samples were then incubated at room temperature for 2 h with secondary antibodies (Alexa Fluor 488 goat-anti-mouse for troponin-I and sarcomeric α-actinin, and Alexa Fluor 594 goat-anti-rabbit for connexin-43) diluted in 10% (v/v) goat serum (1:200 ratio). After several washes with PBS, the samples were counterstained with DAPI for 10 min at 37° C. The stained samples were imaged using an inverted laser scanning confocal microscope (Leica SP5 XMP, Germany) after washing 4 times with PBS.

As can be seen from the discussion presented herein and the Examples, the novel hydrogels of the present invention possess several advantages compared to other elastin derived hydrogels and synthetic elastomers. First, hydrogels of the present invention can be formed within 35 sec in a variety of shapes and sizes, which is shorter than the time required to chemically cross-link elastin-based hydrogels (24 h) (Mithieux et al. (2004)). Second, the photo-cross-linking of the gels in aqueous solution eliminates the use of toxic cross-linkers (Mithieux et al. (2004) and Annabi et al. (2010)) and organic solvents (Annabi et al. (2009)) during the hydrogel synthesis, which may affect the cell viability. Third, the potential to directly encapsulate cells within the hydrogels through photo-cross-linking allows for cell distribution throughout the matrix, thereby overcoming the problems associated with minimal cell penetration into three dimensional matrices due to the presence of low levels of porosity and small pore sizes (Mithieux et al. (2004) and Annabi, Mithieux et al. (2009)). Fourth, unlike other synthetic elastomers such as polyurethane (Miyagawa et al. (2011)), the use of biodegradable TpeMA gel will not cause cytotoxicity after degradation within the body, as the gels are formed from a human protein. Fifth, TpeMA has increased stability compared to some biodegradable elastomers such as polyglycolic acid (PGS) (Giraud et al. (2007)), which can provide adequate structural support until the new tissues form. Sixth, the presence of the full tropoelastin amino acid sequence including the cell-interactive C-terminus (when used) will impart cell-interactive functions to the TpeMA gels by providing integrin-based cell-binding sites.

It will be understood that the invention disclosed and defined in this specification extends to all alternative combinations of two or more of the individual features mentioned or evident from the text or drawings. All of these different combinations constitute various alternative aspects of the invention.

REFERENCES

Peppas, N. A., et al. Hydrogels in biology and medicine: from molecular principles to bionanotechnology. *Adv Mat* 18, 1345-1360 (2006).

Mithieux, S. M., Rasko, J. E. J. & Weiss, A. S. Synthetic elastin hydrogels derived from massive elastic assemblies of self-organized human protein monomers. *Biomaterials* 25, 4921-4927 (2004).

Annabi, N., Mithieux, S. M., Weiss, A. S. & Dehghani, F. Cross-linked open-pore elastic hydrogels based on tropoelastin, elastin and high pressure $CO_2$. *Biomaterials* 31, 1655-1665 (2010).

Annabi, N. et al. Synthesis of highly porous cross-linked elastin hydrogels and their interaction with fibroblasts in vitro. *Biomaterials* 30, 4550-4557 (2009).

Annabi, N., Mithieux, S. M., Weiss, A. S. & Dehghani; F. The fabrication of elastin-based hydrogels using high pressure $CO_2$. *Biomaterials* 30, 1-7 (2009).

Gennaro, A. R., *Remington: The Science and Practice of Pharmacy*, 21st ed. (2006), Lippincott Williams & Wilkins.

Wu, W. J. et al. Glycosaminoglycans mediate the coacervation of human tropoelastin through dominant charge interactions involving lysine side chains. *J Biol Chem* 274, 21719-21724 (1999).

Bellingham, C. M. et al. Recombinant human elastin polypeptides self-assemble into biomaterials with elastin-like properties. *Biopolymers* 70, 445-455 (2003).

Miyagawa, S., Roth, M., Saito, A., Sawa, Y. & Kostin, S. Tissue-Engineered Cardiac Constructs for Cardiac Repair. *Ann Thorac Surg* 91, 320-329 (2011).

Giraud, M., Armbruster, C., Carrel, T. & Tevaearai, H. Current state of the art in myocardial tissue engineering *Tissue Eng* 13, 1825-1836 (2007).

McDevitt, T., Woodhouse, K., Hauschka, S., Murry, C. & Stayton, P. Spatially organized layers of cardiomyocytes on biodegradable polyurethane films for myocardial repair *J Biomed Mater Res A* 66, 586-595 (2003).

Nichol, J. W. et al. Cell-laden microengineered gelatin methacrylate hydrogels. *Biomaterials* 31, 5536-5544 (2010).

Aubin, H. et al. Directed 3D cell alignment and elongation in microengineered hydrogels. *Biomaterials* 31, 6941-6950 (2010).

Charest, J. L., Garcia, A. J. & King, W. P. Myoblast alignment and differentiation on cell culture substrates with microscale topography and model chemistries. *Biomaterials* 28, 2202-2210 (2007).

Brammer, K. S. et al. Improved bone-forming functionality on diameter-controlled TiO(2) nanotube surface. *Acta Biomater* 5, 3215-3223 (2009).

Feinberg, A. W. et al. Muscular thin films for building actuators and powering devices. *Science* 317, 1366-1370 (2007).

Tandon, N. et al. Electrical stimulation systems for cardiac tissue engineering. *Nature protocols* 4, 155-173 (2009).

Baar, K. et al. Self-organization of rat cardiac cells into contractile 3-D cardiac tissue. *Faseb J* 19, 275-277 (2005).

LaNasa, S. M. & Bryant, S. J. Influence of ECM proteins and their analogs on cells cultured on 2-D hydrogels for cardiac muscle tissue engineering. *Acta Biomater* 5, 2929-2938 (2009).

Boateng, S. Y. et al. RGD and YIGSR synthetic peptides facilitate cellular adhesion identical to that of laminin and fibronectin but alter the physiology of neonatal cardiac myocytes. *Am J Physiol Cell Physiol* 288, C30-38 (2005).

Nagapudi et al. *Macromolecules*, 35, 1730-1737 (2002).

Raphel et al. *J Mater Chem* 22, 19429 (2012).

Bae et al. *Soft Matter* 7, 1903-1911 (2011).

Bax et al. *J Bio Chem* 284, 28616-28623 (2009).

Organic Syntheses Collective Volumes, Gilman et al. (eds) John Wiley & Sons, Inc., NY al-Obeidi *Mol Biotechnol* 9, 205-223 (1998).
Hruby *Curr Opin Chem Biol* 1, 114-119 (1997).
Ostergaard *Mol Divers* 3, 17-27 (1997).
Ostresh *Methods Enzymol* 267, 220-234 (1997).
Karlin and Altschul *Proc Natl Acad Sci USA* 87, 2264 (1990).
Karlin and Altschul *Proc Natl Acad Sci USA* 90, 5873-5877 (1993).
Altschul et al. *J Mol Biol* 215, 403 (1990).
Altschul et al. *Nucleic Acids Res* 25, 3389 (1997).
Higgins et al. *Nucleic Acids Res* 22, 4673-4680 (1994).
Coulson, J. M. et al. *Chemical Engineering*, volume 2, $3^{rd}$ Edition, Pergamon Press, page 126 (1978).
Anderson, et al. Biomaterial microarrays: rapid, microscale screening of polymer-cell interaction. *Biomaterials* (2005) 26:4892-4897.
Anderson, et al. Nanoliter-scale synthesis of arrayed biomaterials and application to human embryonic stem cells. *Nature Biotechnology* (2004) 22:863-866.
Orner et al. Arrays for the combinatorial exploration of cell adhesion. *Journal of the American Chemical Society* (2004) 126:10808-10809.
Falsey et al. Peptide and small molecule microarray for high throughput cell adhesion and functional assays. *Bioconjugate Chemistry* (2001) 12:346-353.
Liu et al. *Biomacromolecules* (2001) 2(2): 362-368.
Taurniare et al. *Chem. Comm.* (2006): 2118-2120.
Dijke et al. "Growth Factors for Wound Healing", Bio/Technology, 7:793-798 (1989).
Mulder G D, Haberer P A, Jeter K F, eds. Clinicians' Pocket Guide to Chronic Wound Repair. 4th ed. Springhouse, Pa.: Springhouse Corporation (1998).
Ziegler T. R., Pierce, G. F., and Herndon, D. N. International Symposium on Growth Factors and Wound Healing: Basic Science & Potential Clinical Applications (Boston, 1995, Serono Symposia USA), Publisher: Springer Verlag (1997).
*Harrison's Principles of Internal Medicine*, $13^{th}$ Edition, Eds. T. R. Harrison et al. McGraw-Hill N.Y.
Physicians Desk Reference, $50^{th}$ Edition, Oradell New Jersey, Medical Economics Co (1997).
Pharmacological Basis of Therapeutics, $8^{th}$ Edition, Goodman and Gilman (1990).
United States Pharmacopeia, The National Formulary, USP XII NF XVII (1990).
Sreerama, N. & Woody, R. W. *Anal Biochem* 287, 252-260 (2000).
Klein (1982) *Immunology*, John Wiley, New York, N.Y.
Clark, W. R. (1986) *The Experimental Foundations of Modern Immunology*, Wiley & Sons, Inc., New York
Roitt, I. (1991) *Essential Immunology* (7th Ed.) Blackwell Scientific Publications, Oxford.

The invention claimed is:

1. A hydrogel comprising an acrylated tropoelastin, wherein at least one amine group of the tropoelastin is attached to an acrylate group.

2. A hydrogel comprising an acrylated tropoelastin formed by the process of treating a tropoelastin with a compound comprising an acrylate group in conditions for attaching the acrylate group of the compound to an amine of the tropoelastin.

3. A hydrogel comprising a cross-linked tropoelastin, the cross-linked tropoelastin comprising:
    a plurality of tropoelastin monomers or multimers; and
    a linker in the form of a compound having an acrylate group, wherein the acrylate group of the compound is attached to an amine group of the tropoelastin for cross-linking the monomers or multimers.

4. A hydrogel comprising an acrylated tropoelastin, wherein about 30% to about 50% of the lysine residues of the tropoelastin are attached to an acrylate group.

5. A tissue-engineered construct comprising a hydrogel of claim 1.

6. A tissue-engineered construct comprising a hydrogel of claim 2.

7. A tissue-engineered construct comprising a hydrogel of claim 3.

8. A tissue-engineered construct comprising a hydrogel of claim 4.

9. A device, support or scaffold comprising a hydrogel according to claim 1.

10. A device, support or scaffold comprising a hydrogel according to claim 2.

11. A device, support or scaffold comprising a hydrogel according to claim 3.

12. A device, support or scaffold comprising a hydrogel according to claim 4.

\* \* \* \* \*